US009617218B2

(12) United States Patent
Witschi et al.

(10) Patent No.: US 9,617,218 B2
(45) Date of Patent: *Apr. 11, 2017

(54) CRYSTALLINE FORMS OF A PROLYL HYDROXYLASE INHIBITOR

(71) Applicant: FIBROGEN, INC., San Francisco, CA (US)

(72) Inventors: Claudia Witschi, San Francisco, CA (US); Jung Min Park, San Francisco, CA (US); Michael D. Thompson, Redwood City, CA (US); Michael John Martinelli, San Francisco, CA (US); David A. Yeowell, Chapel Hill, NC (US); Michael P. Arend, Foster City, CA (US)

(73) Assignee: FibroGen, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/805,345

(22) Filed: Jul. 21, 2015

(65) Prior Publication Data

US 2015/0322015 A1 Nov. 12, 2015

Related U.S. Application Data

(63) Continuation of application No. 13/942,443, filed on Jul. 15, 2013, now Pat. No. 9,115,085.

(60) Provisional application No. 61/768,297, filed on Feb. 22, 2013, provisional application No. 61/672,191, filed on Jul. 16, 2012, provisional application No. 61/832,566, filed on Jun. 7, 2013.

(51) Int. Cl.
*C07D 217/26* (2006.01)
*A61K 31/47* (2006.01)

(52) U.S. Cl.
CPC ............ *C07D 217/26* (2013.01); *A61K 31/47* (2013.01)

(58) Field of Classification Search
None
See application file for complete search history.

(56) References Cited

U.S. PATENT DOCUMENTS

| | | | |
|---|---|---|---|
| 3,989,704 A | 11/1976 | Houlihan et al. |
| 4,036,964 A | 7/1977 | Buckle et al. |
| 4,260,611 A | 4/1981 | Bartmann et al. |
| 4,559,403 A | 12/1985 | Bruderer et al. |
| 4,584,379 A | 4/1986 | Wagner |
| 4,673,682 A | 6/1987 | Konz et al. |
| 4,822,800 A | 4/1989 | Falotico et al. |
| 4,952,588 A | 8/1990 | Glamkowski et al. |
| 4,966,906 A | 10/1990 | Glamkowski et al. |
| 5,620,995 A | 4/1997 | Weidmann et al. |
| 5,658,933 A | 8/1997 | Weidmann et al. |
| 5,719,164 A | 2/1998 | Weidmann et al. |
| 5,726,305 A | 3/1998 | Weidmann et al. |
| 6,093,730 A | 7/2000 | Weidmann et al. |
| 6,319,931 B1 | 11/2001 | Kroemer et al. |
| 6,358,973 B1 | 3/2002 | Napoletano et al. |
| 6,358,976 B1 | 3/2002 | Wityak et al. |
| 6,369,053 B1 | 4/2002 | Yuan et al. |
| 6,762,318 B2 | 7/2004 | Kodra et al. |
| 6,777,425 B2 | 8/2004 | Burli et al. |
| 6,903,114 B2 | 6/2005 | Backstrom et al. |
| 7,208,601 B2 | 4/2007 | Mjalli et al. |
| 7,323,475 B2 | 1/2008 | Arend et al. |
| 7,618,940 B2 | 11/2009 | Fourney et al. |
| 7,629,357 B2 | 12/2009 | Arend et al. |
| 7,696,223 B2 | 4/2010 | Deng et al. |
| 7,863,292 B2 | 1/2011 | Arend et al. |
| 7,928,120 B2 | 4/2011 | Arend et al. |
| 8,017,625 B2 | 9/2011 | Arend et al. |
| 8,124,582 B2 | 2/2012 | Guenzler-Pukall et al. |
| 8,217,043 B2 | 7/2012 | Deng et al. |
| 8,269,008 B2 | 9/2012 | Arend et al. |
| 8,278,325 B2 | 10/2012 | Arend et al. |
| 8,324,405 B2 | 12/2012 | Ho et al. |
| 8,703,795 B2 | 4/2014 | Turtle et al. |
| 8,759,373 B2 | 6/2014 | Arend et al. |
| 8,765,956 B2 | 7/2014 | Arend et al. |
| 8,883,823 B2 | 11/2014 | Witschi et al. |
| 8,916,585 B2 | 12/2014 | Arend et al. |
| 8,921,389 B2 | 12/2014 | Ng et al. |
| 8,952,160 B2 | 2/2015 | Zhou et al. |
| 9,115,085 B2 | 8/2015 | Witschi et al. |
| 9,340,511 B2 | 5/2016 | Thompson et al. |
| 2003/0153503 A1 | 8/2003 | Klaus et al. |
| 2003/0176317 A1 | 9/2003 | Guenzler-Pukall et al. |
| 2004/0204356 A1 | 10/2004 | Guenzler-Pukall et al. |

(Continued)

FOREIGN PATENT DOCUMENTS

CA 2134866 5/1995
EP 0650960 5/1995

(Continued)

OTHER PUBLICATIONS

Bruick et al., A Conserved Family of Proly-4-Hydroxylases That Modify HIF, *Science*, vol. 294, pp. 1337-1340, (2001).
Cunliffe et al., Novel Inhibitors of Prolyl 4-Hydroxylase 3 Inhibition by the Substrate Analogue N-Oxaloglycine and Its Derivatives, *J. Med. Chem.*, vol. 35, pp. 2652-2658, (1992).
Duro et al., Sintesi Ed Attivita Farmacologica D1 Ammmino-E Dialchilamminoalchilammidi-D1 Derivati Della 3-Carbossi-4-Fenilisochinolina, *Ed. Sc.*, vol. 36, pp. 400-411, (1980) (Abstract in English).
Franklin et al., Approaches to the Design of Anti-Fibrotic Drugs, *Biochem. Soc. Trans.*, 19(4):812-815, (1991).
Guo et al., Selective Protection of 2',2'-Difluorodeoxycytidine (Gemcitabine), *J. Org. Chem.*, vol. 64, pp. 8319-8322, (1999).
International Search Report with Written Opinion for PCT/US2004/017773, dated Oct. 13, 2004.
International Search Report with Written Opinion for PCT/US2013/050539, dated Jul. 2, 2014.

(Continued)

*Primary Examiner* — Zinna Northington Davis
(74) *Attorney, Agent, or Firm* — FibroGen, Inc.; Leanne C. Price

(57) ABSTRACT

The present disclosure relates to crystalline solid forms of [(4-hydroxy-1-methyl-7-phenoxy-isoquinoline-3-carbonyl)-amino]-acetic acid, the process of preparing the forms, and pharmaceutical compositions and methods of use thereof.

6 Claims, 37 Drawing Sheets

(56) References Cited

U.S. PATENT DOCUMENTS

| | | |
|---|---|---|
| 2004/0235082 A1 | 11/2004 | Fourney et al. |
| 2004/0254215 A1 | 12/2004 | Arend et al. |
| 2005/0020487 A1 | 1/2005 | Klaus et al. |
| 2006/0178316 A1 | 8/2006 | Klaus et al. |
| 2006/0178317 A1 | 8/2006 | Klaus et al. |
| 2006/0183695 A1 | 8/2006 | Klaus et al. |
| 2006/0199836 A1 | 9/2006 | Turtle et al. |
| 2006/0251638 A1 | 11/2006 | Guenzler-Pukall et al. |
| 2006/0258660 A1 | 11/2006 | Guenzler-Pukall et al. |
| 2006/0258702 A1 | 11/2006 | Guenzler-Pukall et al. |
| 2006/0270699 A1 | 11/2006 | Guenzler-Pukall et al. |
| 2006/0276477 A1 | 12/2006 | Klaus et al. |
| 2007/0004627 A1 | 1/2007 | Seeley et al. |
| 2007/0155784 A1 | 7/2007 | Arend et al. |
| 2007/0292433 A1 | 12/2007 | Seeley et al. |
| 2007/0293575 A1 | 12/2007 | Seeley et al. |
| 2010/0047367 A1 | 2/2010 | Deng et al. |
| 2010/0303928 A1 | 12/2010 | Arend et al. |
| 2010/0330199 A1 | 12/2010 | Zhou et al. |
| 2010/0331400 A1 | 12/2010 | Ho et al. |
| 2011/0212959 A1 | 9/2011 | Arend et al. |
| 2011/0305776 A1 | 12/2011 | Ho et al. |
| 2012/0149712 A1 | 6/2012 | Klaus et al. |
| 2013/0178417 A1 | 7/2013 | Arend et al. |
| 2014/0024676 A1 | 1/2014 | Witschi et al. |
| 2014/0343094 A1 | 11/2014 | Arend et al. |
| 2015/0031696 A1 | 1/2015 | Arend et al. |
| 2015/0038528 A1 | 2/2015 | Ho et al. |
| 2015/0038529 A1 | 2/2015 | Witschi et al. |

FOREIGN PATENT DOCUMENTS

| | | |
|---|---|---|
| EP | 0650961 | 5/1995 |
| EP | 0911340 | 4/1999 |
| JP | A-H07-224039 | 8/1995 |
| JP | A-H07-228571 | 8/1995 |
| JP | A-H11302257 | 11/1999 |
| JP | 2005-524612 | 8/2005 |
| JP | 2006-514113 | 4/2006 |
| JP | 2006-137763 | 6/2006 |
| JP | 2006-527199 | 11/2006 |
| WO | WO 96/18616 | 6/1996 |
| WO | WO 01/58892 | 8/2001 |
| WO | WO 02/070510 | 9/2002 |
| WO | WO 02/074249 | 9/2002 |
| WO | WO 02/074981 | 9/2002 |
| WO | WO 02/100832 | 12/2002 |
| WO | WO 02/101073 | 12/2002 |
| WO | WO 03/053997 | 7/2003 |
| WO | WO 2004/052285 | 6/2004 |
| WO | WO 2004/108121 | 12/2004 |
| WO | WO 2004/108681 | 12/2004 |
| WO | WO 2005/007192 | 1/2005 |
| WO | WO 2005/009962 | 2/2005 |
| WO | WO 2005/011696 | 2/2005 |
| WO | WO 2005/014533 | 2/2005 |
| WO | WO-2007/097929 A1 | 8/2007 |
| WO | WO-2010/056767 A1 | 5/2010 |
| WO | WO-2012/097331 A1 | 7/2012 |
| WO | WO 2013/013609 | 1/2013 |
| WO | WO 2014/014834 | 1/2014 |
| WO | WO 2014/014835 | 1/2014 |
| WO | WO-2014/116849 A1 | 7/2014 |

OTHER PUBLICATIONS

Ivan et al., HIFα Targeted for VHL-Mediated Destruction by Proline Hydroxylation: Implications for $O_2$ Sensing, *Science*, 292:464-468, (2001).

Jaakkola et al., Targeting of HIF-α to the von Hippel-Lindau Ubiquitylation Complex by $O_2$-Regulated Prolyl Hydroxylation, *Science*, 292(5516):468-472, (2001).

Lando et al., Oxygen-Dependent Regulation of Hypoxia-Inducible Factors by Prolyl and Asparaginyl Hydroxylation, *Eur. J. Biochem*, 270:781-790, (2003).

Richard et al., Nonhypoxic Pathway Mediates the Induction of Hypoxia-Inducible Factor 1α in Vascular Smooth Muscle Cells, *J. Bio. Chm.*, 275:26765-26771, (2000).

Safran et al., HIF Hydroxylation and the Mammalian Oxygen-sensingPathway, *J. Clin. Invest.*, 111(6):779-783, (2003).

Sandau et al., Induction of Hypoxia-Inducible-Factor 1 by Nitric Oxide Is Mediated Via the PI 3K Pathway, *Biochem. Biophys. Res. Commun.*, 278:263-267, (2000).

Sato et al., Stability and Physicochemical Properties of Viracept Tablets, *Antibiotics and Chemotherapy*, 14(9):1589-1592, (1998)—English Translation Not Available.

Sodhi et al., MAPK and Akt Act Cooperatively But Independently on Hypoxia Inducible Factor-1 α in *ras*V12 Unpregulation of VEGF, *Biochem. Biophys. Res. Commun.*, 287:292-300, (2001).

Tacchini et al., Hepatocyte Growth Factor Signalling Stimulates Hypoxia Inducible Factor-1 (HIF-1) Activity in HepG2 Hepatoma Cells, *Carcinogenesis*, 22:1363-1371, (2001).

Wu et al., Regulatory Perspectives of Type II Prodrug Development and Time-Dependent Toxicity Management: Nonclinical Pharm/Tox Analysis and the Role of Comparative Toxicology, *Toxicology*, 236, pp. 1-6, (2007).

International Search Report for PCT Application No. PCT/US2013/050538 dated Sep. 17, 2013.

Written Opinion for PCT Application No. PCT/US2013/050538 dated Jan. 16, 2015.

Written Opinion and Search Report for SG Application No. 11201500236S, dated Dec. 8, 2015.

International Preliminary Report on Patentability for International Application No. PCT/US2013/050539 dated Jan. 20, 2015. (9 pages).

CRYSTALLINE FORMS OF A PROLYL HYDROXYLASE INHIBITOR

CROSS REFERENCE TO RELATED APPLICATION

This application is a continuation of U.S. application Ser. No. 13/942,443, filed Jul. 15, 2013, now U.S. Pat. No. 9,115,085, which application claims the benefit under 35 U.S.C. §119(e) to U.S. Application No. 61/672,191, filed Jul. 16, 2012, U.S. Application No. 61/768,297, filed Feb. 22, 2013, and U.S. Application No. 61/832,566, filed Jun. 7, 2013, all of which are incorporated herein by reference.

FIELD

The present disclosure relates to crystalline solid forms of [(4-hydroxy-1-methyl-7-phenoxy-isoquinoline-3-carbonyl)-amino]-acetic acid, the process of preparing the forms, and pharmaceutical compositions and methods of use thereof.

STATE OF THE ART

A compound can exist in one or more crystalline forms. Crystalline forms of a drug substance can have different physical properties, including melting point, solubility, dissolution rate, optical and mechanical properties, vapor pressure, hygroscopicity, particle shape, density, and flowability. These properties can have a direct effect on the ability to process and/or manufacture a compound as a drug product. Crystalline forms can also exhibit different stabilities and bioavailability. The most stable crystalline form of a drug product is often chosen during drug development based on the minimal potential for conversion to another crystalline form and on its greater chemical stability. To ensure the quality, safety, and efficacy of a drug product, it is important to choose a crystalline form that is stable, is manufactured reproducibly, and has favorable physicochemical properties.

[(4-Hydroxy-1-methyl-7-phenoxy-isoquinoline-3-carbonyl)-amino]-acetic acid (hereinafter, Compound A) is a potent inhibitor of hypoxia inducible factor (HIF) prolyl hydroxylase, as described in U.S. Pat. No. 7,323,475. HIF prolyl hydroxylase inhibitors are useful for increasing the stability and/or activity of HIF, and useful for, inter alia, treating and preventing disorders associated with HIF, including anemia, ischemia, and hypoxia.

SUMMARY

The present disclosure fulfills these needs and others by providing crystalline forms of Compound A, salts, and solvates. The present disclosure also provides an amorphous form of Compound A. The present disclosure also provides pharmaceutical compositions comprising amorphous or one or more crystalline forms of Compound A. The disclosure also provides processes for making the amorphous and crystalline solid forms and methods for using them to treat, and prevent HIF-associated disorders including conditions involving anemia, ischemia, and hypoxia.

Thus, one embodiment provided is crystalline [(4-hydroxy-1-methyl-7-phenoxy-isoquinoline-3-carbonyl)-amino]-acetic acid (Compound A Form A) characterized by an X-ray powder diffractogram comprising the following peaks: 8.5, 16.2, and 27.4°2θ±0.2°2θ.

Another embodiment provided is crystalline [(4-hydroxy-1-methyl-7-phenoxy-isoquinoline-3-carbonyl)-amino]-acetic acid hemihydrate (Compound A Form B) characterized by an X-ray powder diffractogram comprising the following peaks: 4.2, 8.3, and 16.6°2θ±0.2°2θ.

Yet another embodiment provided is crystalline [(4-hydroxy-1-methyl-7-phenoxy-isoquinoline-3-carbonyl)-amino]-acetic acid hexafluoropropan-2-ol solvate (Compound A Form C) characterized by an X-ray powder diffractogram comprising the following peaks: 4.5, 13.7, and 16.4°2θ±0.2°2θ.

Yet another embodiment provided is crystalline [(4-hydroxy-1-methyl-7-phenoxy-isoquinoline-3-carbonyl)-amino]-acetic acid DMSO:water solvate (Compound A Form D) characterized by an X-ray powder diffractogram comprising the following peaks: 8.4, 8.5, and 16.8°2θ±0.2°2θ.

Yet another embodiment provided is crystalline [(4-hydroxy-1-methyl-7-phenoxy-isoquinoline-3-carbonyl)-amino]-acetic acid sodium salt (Compound A sodium salt) characterized by an X-ray powder diffractogram comprising the following peaks: 5.3, 16.0, and 21.6°2θ±0.2°2θ.

Yet another embodiment provided is crystalline [(4-hydroxy-1-methyl-7-phenoxy-isoquinoline-3-carbonyl)-amino]-acetic acid L-arginine salt (Compound A L-arginine salt) characterized by an X-ray powder diffractogram comprising the following peaks: 20.8, 21.8, and 25.4°2θ±0.2°2θ.

Yet another embodiment provided is crystalline [(4-hydroxy-1-methyl-7-phenoxy-isoquinoline-3-carbonyl)-amino]-acetic acid L-lysine salt (Compound A L-lysine salt) characterized by an X-ray powder diffractogram comprising the following peaks: 19.8, 20.7, and 21.2°2θ±0.2°2θ.

Yet another embodiment provided is crystalline [(4-hydroxy-1-methyl-7-phenoxy-isoquinoline-3-carbonyl)-amino]-acetic acid ethanolamine salt (Compound A ethanolamine salt) characterized by an X-ray powder diffractogram comprising the following peaks: 21.8, 22.7, and 27.1°2θ±0.2°2θ.

Yet another embodiment provided is crystalline [(4-hydroxy-1-methyl-7-phenoxy-isoquinoline-3-carbonyl)-amino]-acetic acid diethanolamine salt (Compound A diethanolamine salt) characterized by an X-ray powder diffractogram comprising the following peaks: 16.9, 23.7, and 25.0°2θ±0.2°2θ.

Yet another embodiment provided is crystalline [(4-hydroxy-1-methyl-7-phenoxy-isoquinoline-3-carbonyl)-amino]-acetic acid tromethamine salt (Compound A tromethamine salt) characterized by an X-ray powder diffractogram comprising the following peaks: 10.1, 14.2, and 21.1°2θ±0.2°2θ.

Yet another embodiment provided is amorphous [(4-hydroxy-1-methyl-7-phenoxy-isoquinoline-3-carbonyl)-amino]-acetic acid (amorphous Compound A).

Yet another embodiment provided is substantially amorphous [(4-hydroxy-1-methyl-7-phenoxy-isoquinoline-3-carbonyl)-amino]-acetic acid potassium salt (Compound A potassium salt).

Still another embodiment provided is directed to a pharmaceutical composition comprising a crystalline or amorphous form of Compound A, or a salt thereof, and a pharmaceutically acceptable excipient.

Additionally, the disclosure provides in one embodiment a method for treating, pretreating, or delaying onset or progression of a condition mediated at least in part by hypoxia inducible factor (HIF). The method comprises administering to a patient in need thereof a therapeutically effective amount of a compound selected from the group consisting of: Compound A Form A, Compound A Form B, Compound A Form C, Compound A Form D, Compound A sodium salt, Compound A L-arginine salt, Compound A L-lysine salt, Compound A ethanolamine salt, Compound A diethanolamine salt, Compound A tromethamine salt, amorphous Compound A, and Compound A potassium salt, as described generally above.

Also provided is a method for treating, pretreating, or delaying onset or progression of a condition mediated at least in part by erythropoietin (EPO), comprising administering to a patient in need thereof, a therapeutically effective amount of a compound selected from the group consisting of: Compound A Form A, Compound A Form B, Compound A Form C, Compound A Form D, Compound A sodium salt, Compound A L-arginine salt, Compound A L-lysine salt, Compound A ethanolamine salt, Compound A diethanolamine salt, Compound A tromethamine salt, amorphous Compound A, and Compound A potassium salt, as described generally above.

Also provided is a method for treating, pretreating, or delaying onset or progression of anemia, comprising administering to a patient in need thereof, a therapeutically effective amount of a compound selected from the group consisting of: Compound A Form A, Compound A Form B, Compound A Form C, Compound A Form D, Compound A sodium salt, Compound A L-arginine salt, Compound A L-lysine salt, Compound A ethanolamine salt, Compound A diethanolamine salt, Compound A tromethamine salt, amorphous Compound A, and Compound A potassium salt, as described generally above.

Also provided is a method of inhibiting the activity of a HIF hydroxylase enzyme, the method comprising bringing into contact the HIF hydroxylase enzyme and a therapeutically effective amount of a compound selected from the group consisting of: Compound A Form A, Compound A Form B, Compound A Form C, Compound A Form D, Compound A sodium salt, Compound A L-arginine salt, Compound A L-lysine salt, Compound A ethanolamine salt, Compound A diethanolamine salt, Compound A tromethamine salt, amorphous Compound A, and Compound A potassium salt, as described generally above.

C./75% RH (middle), and Compound A methanesulfonic acid salt pattern 2 as isolated (second to top) and at 40° C./75% RH (top).

Figure 30:
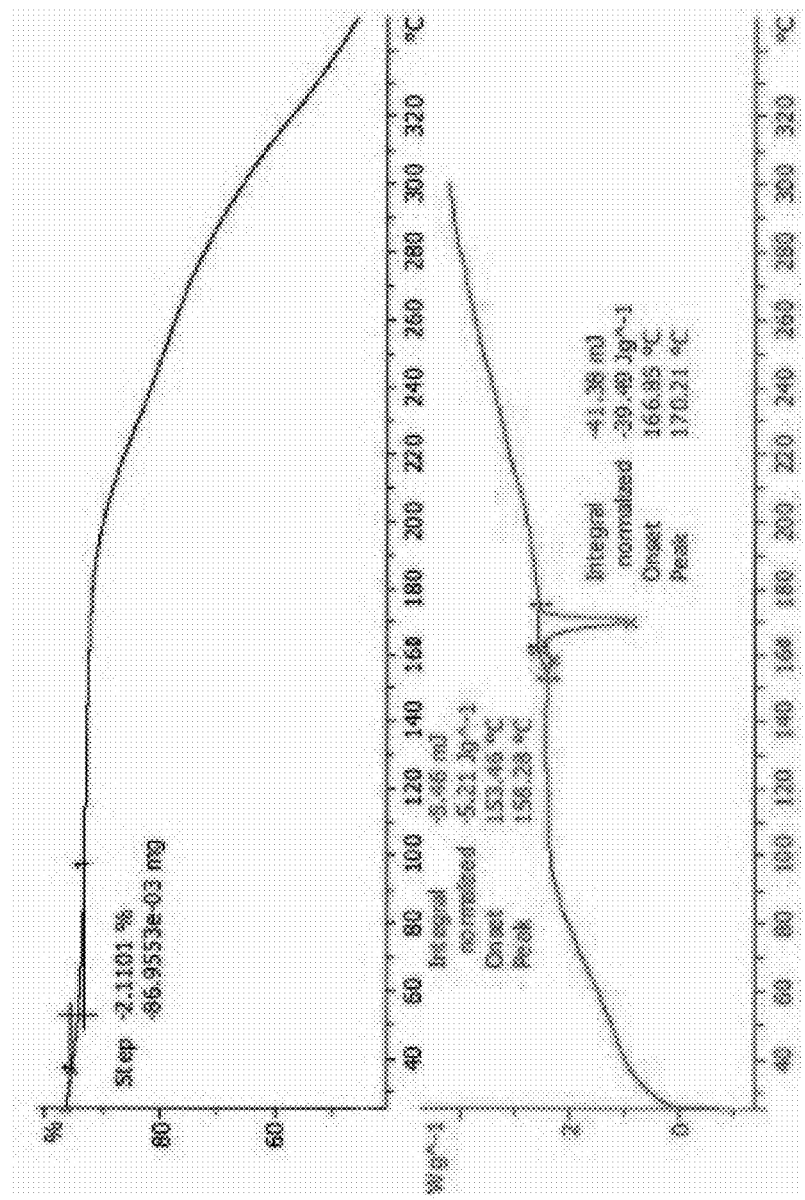

FIG. 30 is a thermogravimetric analysis (TGA) (top) and a differential scanning calorimetry (DSC) curve (bottom) of Compound A methanesulfonic acid salt.

Figure 31:
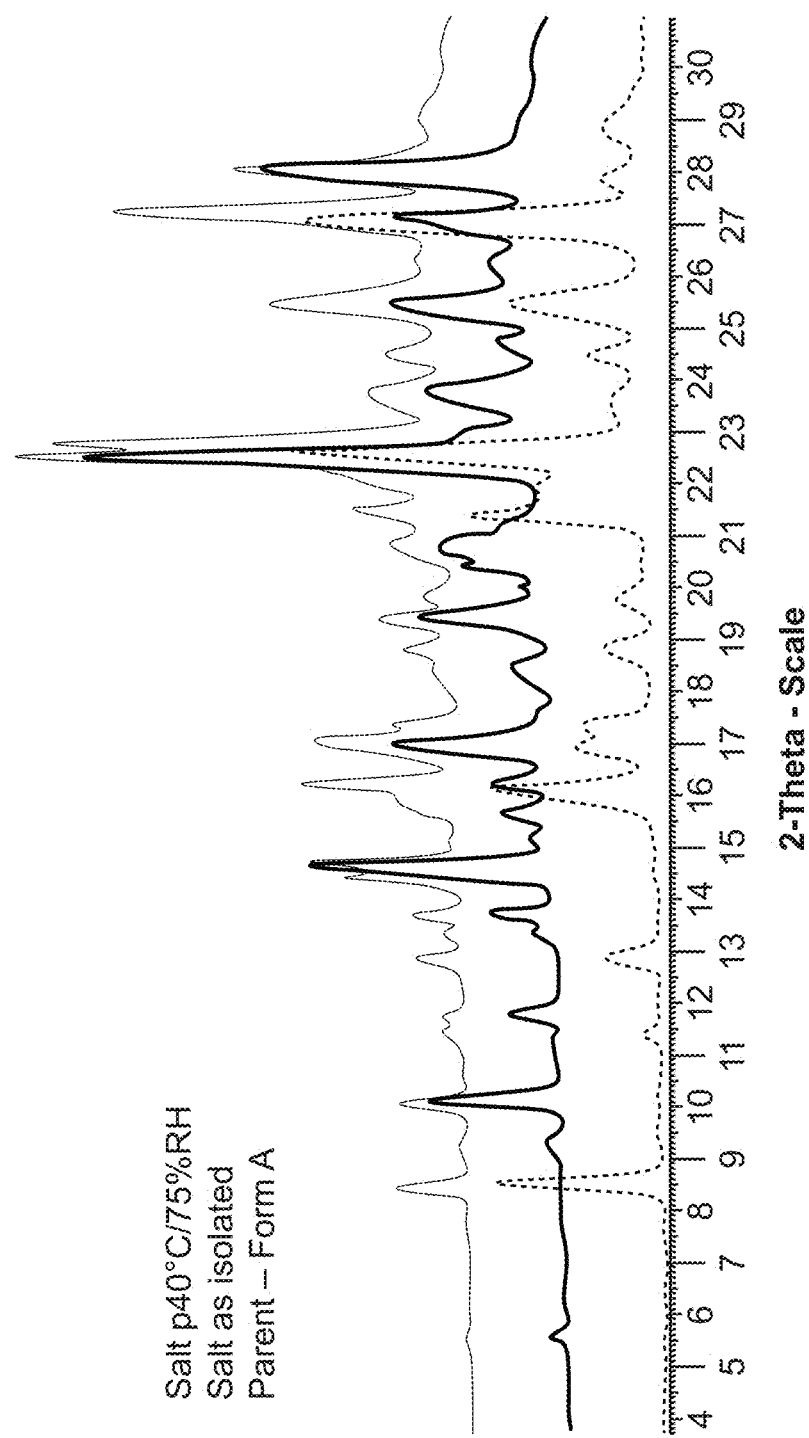

FIG. 31 is an X-ray powder diffraction pattern of Compound A Form A (bottom), Compound A bis triethylamine salt as isolated (middle) and Compound A bis triethylamine salt at 40° C./075% RH (top).

Figure 32:
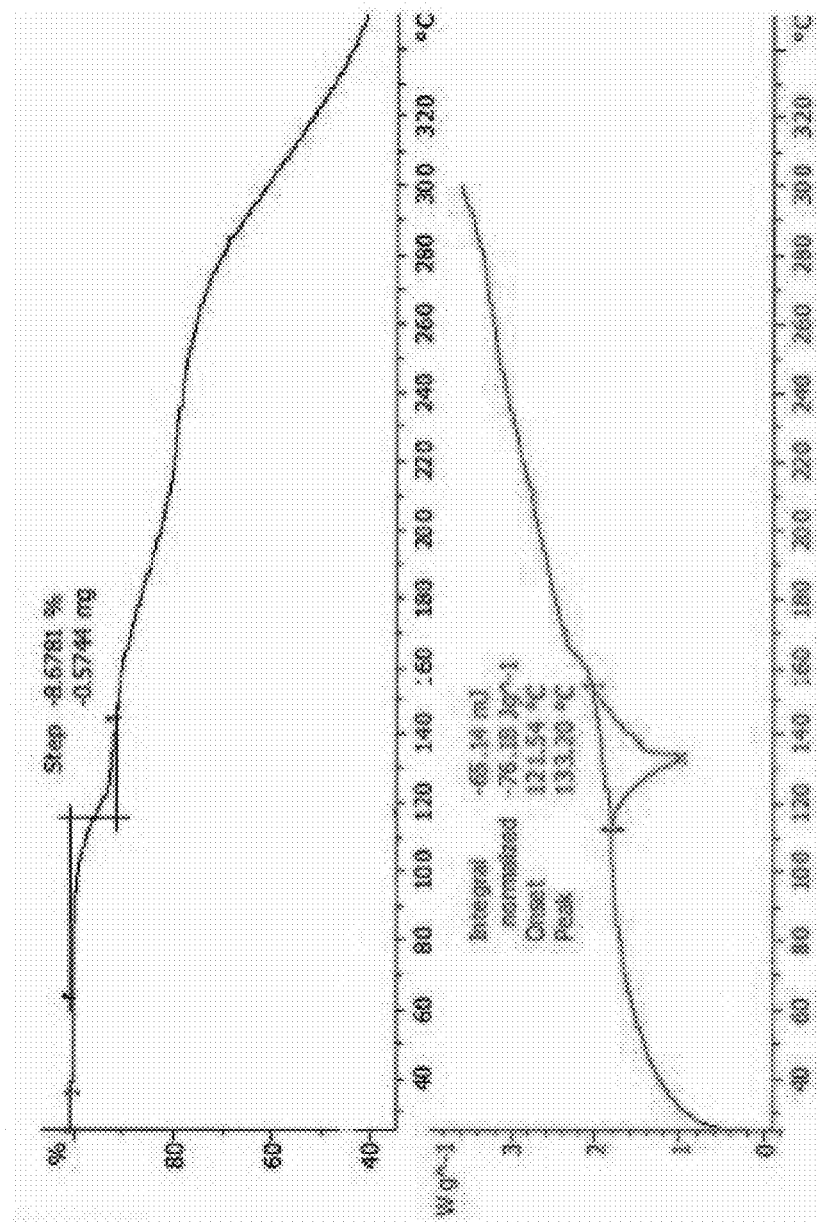

FIG. 32 is a thermogravimetric analysis (TGA) (top) and a differential scanning calorimetry (DSC) curve (bottom) of Compound A bis triethylamine salt.

Figure 33:
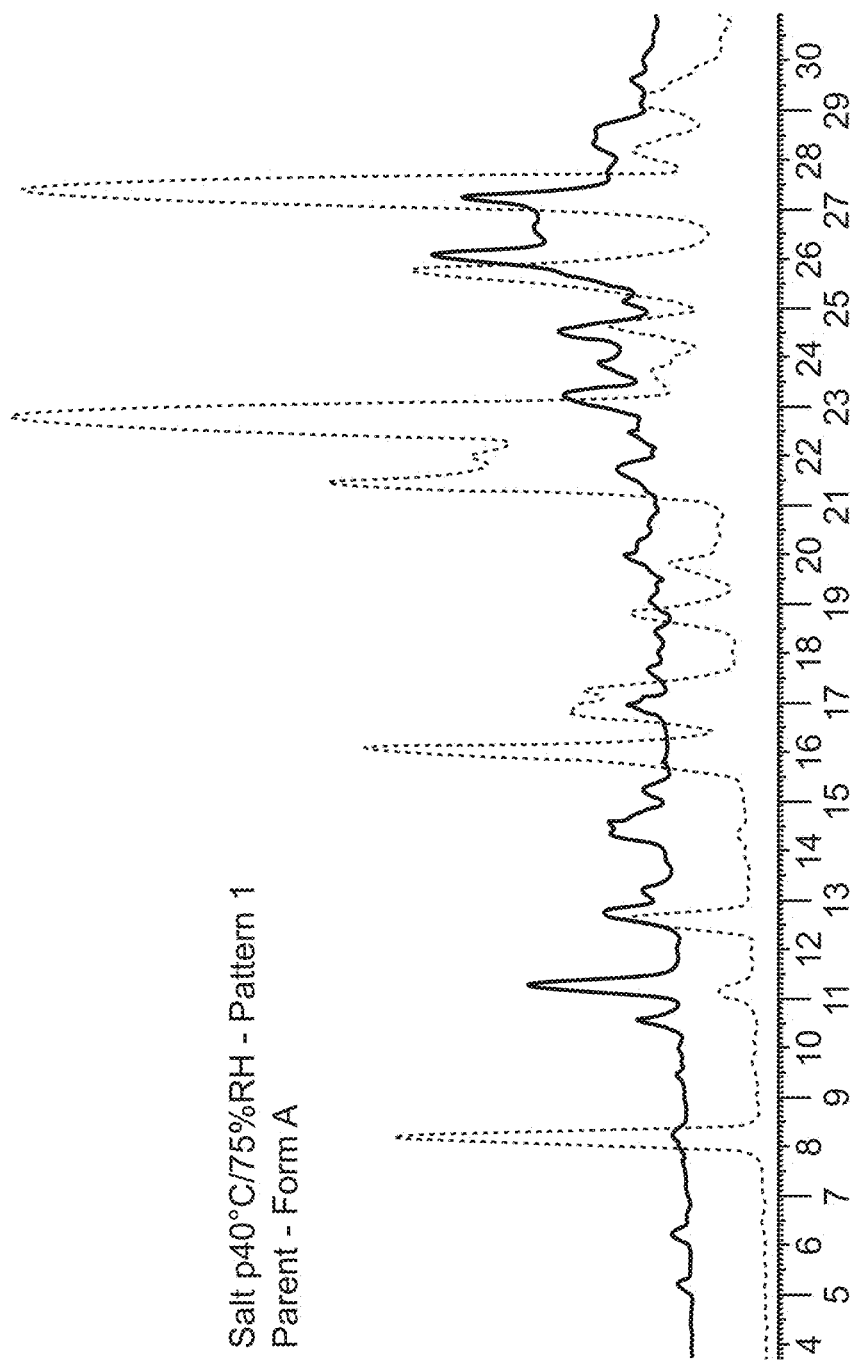

FIG. 33 is an X-ray powder diffraction pattern of Compound A Form A (bottom), and Compound A hemi calcium salt (second crop) at 40° C./75% RH (top).

Figure 34:
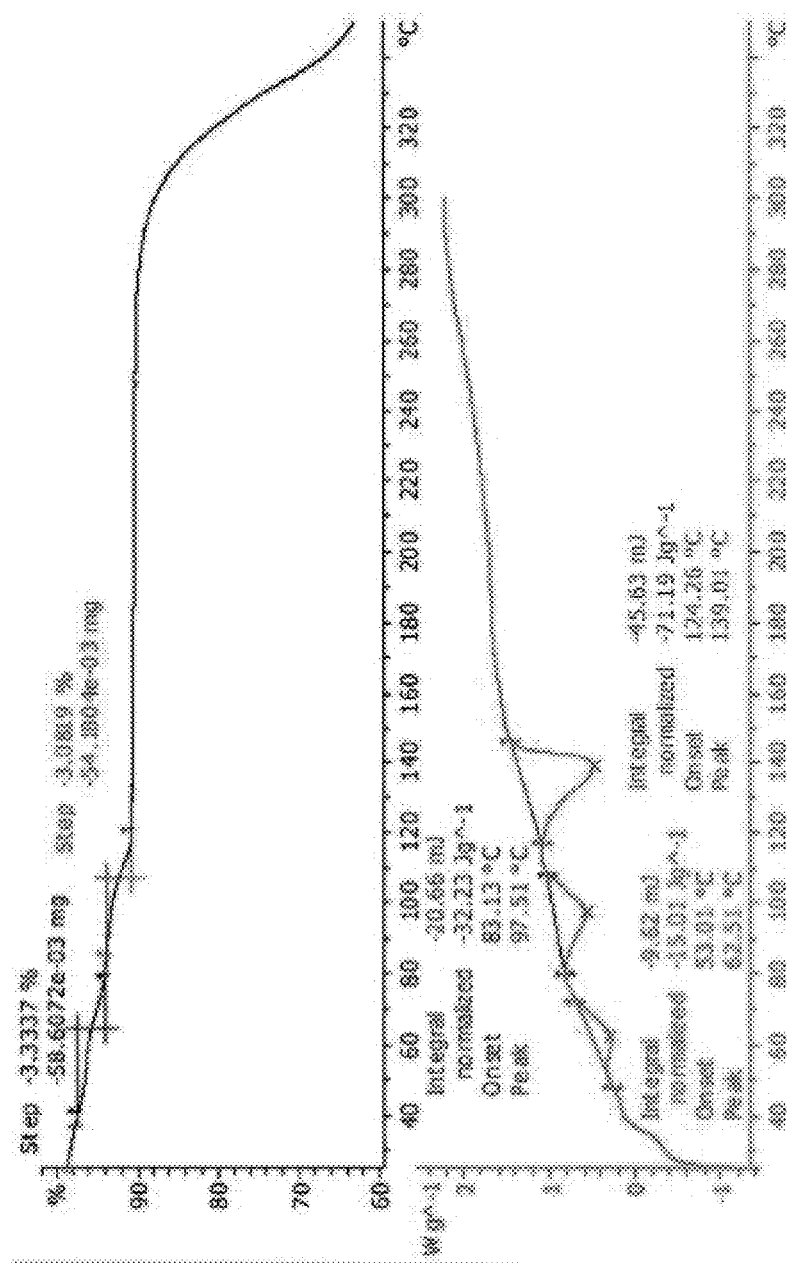

FIG. 34 is a thermogravimetric analysis (TGA) (top) and a differential scanning calorimetry (DSC) curve (bottom) of Compound A hemi calcium salt.

Figure 35:
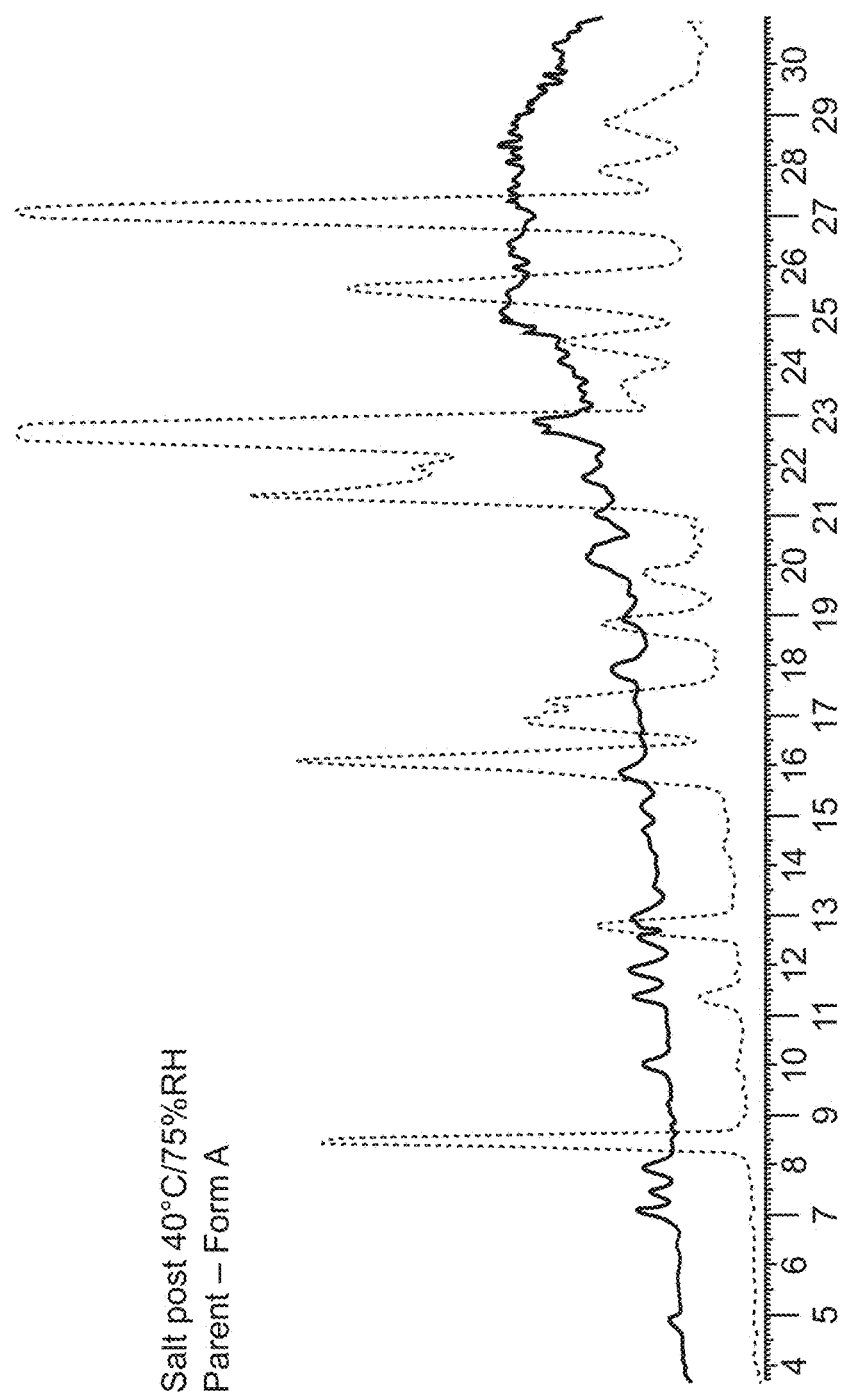

FIG. 35 is an X-ray powder diffraction pattern of Compound A Form A (bottom), and Compound A hemi magnesium salt (second crop) at 40° C./75% RH (top).

Figure 36:
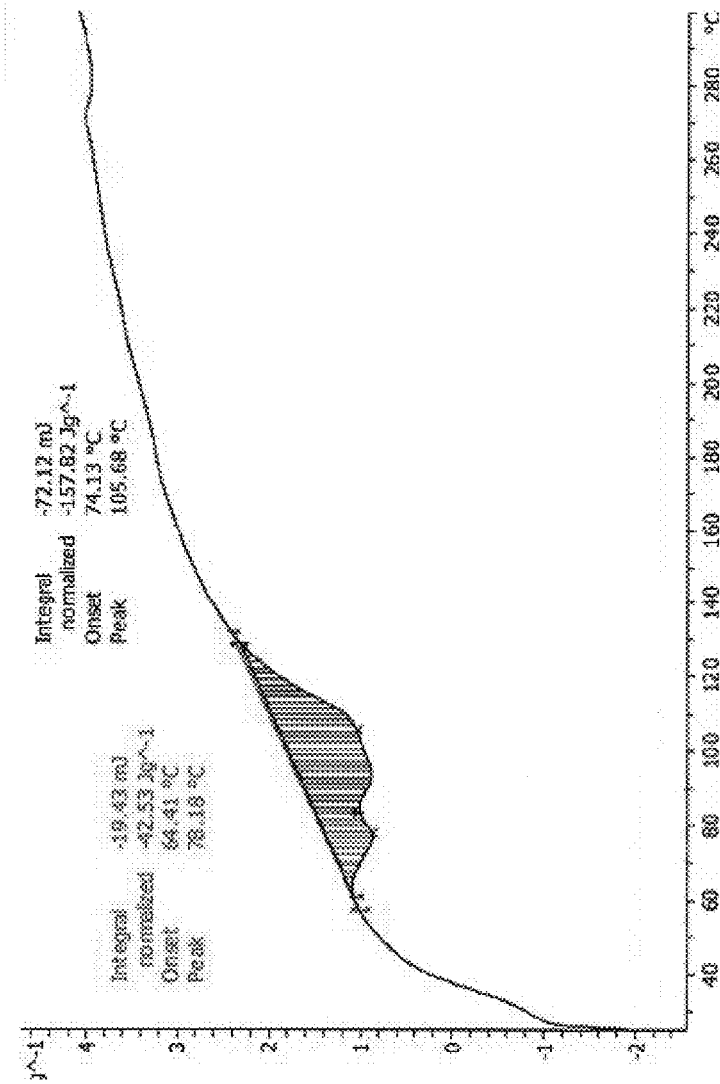

FIG. 36 is a differential scanning calorimetry (DSC) curve of Compound A hemi magnesium salt.

Figure 37:
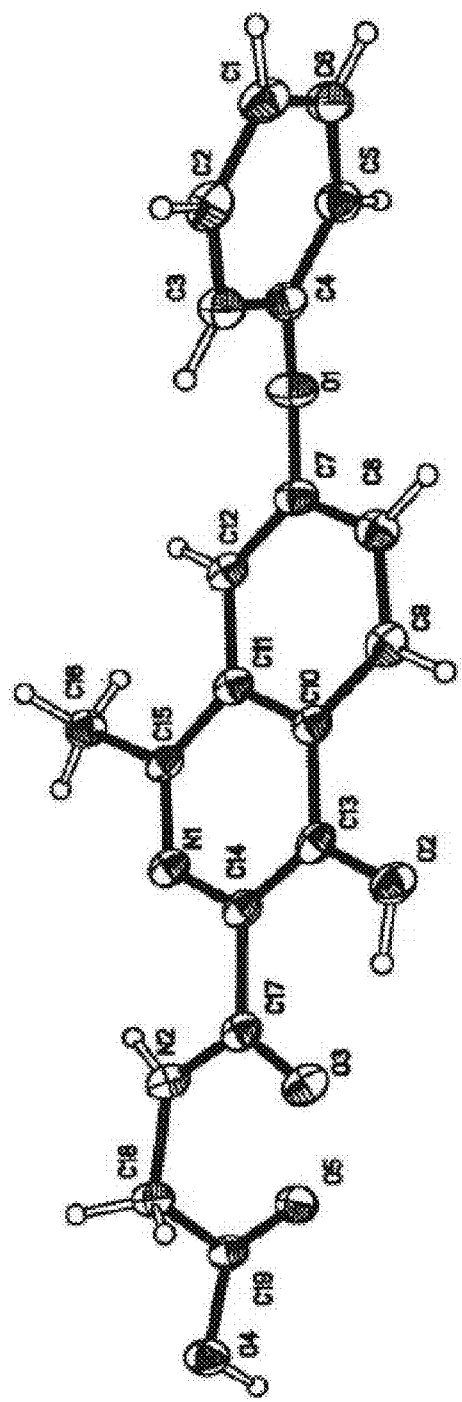

FIG. 37 is the molecular configuration of Compound A Form A.

DETAILED DESCRIPTION

The compound [(4-hydroxy-1-methyl-7-phenoxy-isoquinoline-3-carbonyl)-amino]-acetic acid (Compound A) is a potent inhibitor of hypoxia inducible factor (HIF) prolyl hydroxylase and has the following formula:

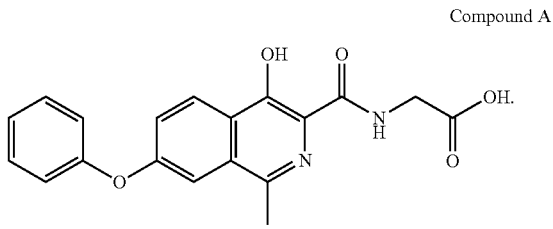 [SMILES: Cc1nc(C(=O)NCC(=O)O)c(O)c2ccc(Oc3ccccc3)cc12]

Compound A

The present disclosure provides crystalline forms of Compound A, salts of Compound A, and solvates of Compound A. The present disclosure also provides an amorphous form of Compound A. The present disclosure also provides pharmaceutical compositions comprising amorphous or crystalline forms of Compound A. The disclosure also provides processes for making the amorphous and crystalline solid forms and methods for using them to treat, and prevent HIF-associated disorders including conditions involving anemia, ischemia, and hypoxia.

Prior to discussing in further detail, the following terms will be defined.

1. Definitions

As used herein, the following terms have the following meanings.

The singular forms "a," "an," and "the" and the like include plural referents unless the context clearly dictates otherwise. Thus, for example, reference to "a compound" includes both a single compound and a plurality of different compounds.

The term "about" when used before a numerical designation, e.g., temperature, time, amount, and concentration, including a range, indicates approximations which may vary by ±10%, ±5% or ±1%.

The term "solvate" refers to a complex formed by the combining of Compound A and a solvent.

The terms "substantially amorphous" and "mostly amorphous" refer to amorphous Compound A where a small amount of crystalline Compound A may be present. In some embodiments, the amount of crystalline Compound A is less than about 10%, or less than about 5%, or less than about 2%, or less than about 1%, or less than about 0.2%, or less than about 0.1%.

"Administration" refers to introducing an agent into a patient. A therapeutic amount can be administered, which can be determined by the treating physician or the like. An oral route of administration is preferred for the crystalline forms of Compound A described herein. The related terms and phrases "administering" and "administration of", when used in connection with a compound or pharmaceutical composition (and grammatical equivalents) refer both to direct administration, which may be administration to a patient by a medical professional or by self-administration by the patient, and/or to indirect administration, which may be the act of prescribing a drug. For example, a physician who instructs a patient to self-administer a drug and/or provides a patient with a prescription for a drug is administering the drug to the patient. In any event, administration entails delivery of the drug to the patient.

"Excipient" as used herein means an inert or inactive substance used in the production of pharmaceutical products, including without limitation any substance used as a binder, disintegrant, coating, compression/encapsulation aid, cream or lotion, lubricant, parenteral, sweetener or flavoring, suspending/gelling agent, or wet granulation agent. Binders include, e.g., carbopol, povidone, xanthan gum, etc.; coatings include, e.g., cellulose acetate phthalate, ethylcellulose, gellan gum, maltodextrin, etc.; compression/encapsulation aids include, e.g., calcium carbonate, dextrose, fructose, honey, lactose (anhydrate or monohydrate; optionally in combination with aspartame, cellulose, or microcrystalline cellulose), starch, sucrose, etc.; disintegrants include, e.g., croscarmellose sodium, gellan gum, sodium starch glycolate, etc.; creams and lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; parenterals include, e.g., mannitol, povidone, etc.; plasticizers include, e.g., dibutyl sebacate, polyvinylacetate phthalate, etc.; suspending/gelling agents include, e.g., carrageenan, sodium starch glycolate, xanthan gum, etc.; sweeteners include, e.g., aspartame, dextrose, fructose, sorbitol, sucrose, etc.; and wet granulation agents include, e.g., calcium carbonate, maltodextrin, microcrystalline cellulose, etc.

"Therapeutically effective amount" or "therapeutic amount" refers to an amount of a drug or an agent that when administered to a patient suffering from a condition, will have the intended therapeutic effect, e.g., alleviation, amelioration, palliation or elimination of one or more manifestations of the condition in the patient. The therapeutically effective amount will vary depending upon the subject and the condition being treated, the weight and age of the subject, the severity of the condition, the particular composition or excipient chosen, the dosing regimen to be followed, timing of administration, the manner of administration and the like, all of which can be determined readily by one of ordinary skill in the art. The full therapeutic effect does not necessarily occur by administration of one dose, and may occur only after administration of a series of doses. Thus, a therapeutically effective amount may be administered in one or more administrations. For example, and without limitation, a therapeutically effective amount of an agent, in the context of treating anemia, refers to an amount of the agent that alleviates, ameliorates, palliates, or eliminates one or more symptoms of anemia in the patient.

"Treatment", "treating", and "treat" are defined as acting upon a disease, disorder, or condition with an agent to reduce or ameliorate the harmful or any other undesired effects of the disease, disorder, or condition and/or its symptoms. Treatment, as used herein, covers the treatment of a human patient, and includes: (a) reducing the risk of occurrence of the condition in a patient determined to be predisposed to the disease but not yet diagnosed as having the condition, (b) impeding the development of the condition, and/or (c) relieving the condition, i.e., causing regression of the condition and/or relieving one or more symptoms of the condition.

An "XRPD pattern" is an x-y graph with diffraction angle (i.e., ° 2θ) on the x-axis and intensity on the y-axis. The peaks within this pattern may be used to characterize a crystalline solid form. As with any data measurement, there is variability in XRPD data. The data are often represented solely by the diffraction angle of the peaks rather than including the intensity of the peaks because peak intensity can be particularly sensitive to sample preparation (for example, particle size, moisture content, solvent content, and preferred orientation effects influence the sensitivity), so samples of the same material prepared under different conditions may yield slightly different patterns; this variability is usually greater than the variability in diffraction angles. Diffraction angle variability may also be sensitive to sample preparation. Other sources of variability come from instrument parameters and processing of the raw X-ray data: different X-ray instruments operate using different parameters and these may lead to slightly different XRPD patterns from the same solid form, and similarly different software packages process X-ray data differently and this also leads to variability. These and other sources of variability are known to those of ordinary skill in the pharmaceutical arts. Due to such sources of variability, it is usual to assign a variability of ±0.2° 2θ to diffraction angles in XRPD patterns.

2. Solid Forms of Compound A

As described generally above, the present disclosure provides solid forms of [(4-hydroxy-1-methyl-7-phenoxy-isoquinoline-3-carbonyl)-amino]-acetic acid (Compound A).

Compound A Form A is characterized by its X-ray powder diffractogram that comprises peaks at 8.5, 16.2, and 27.4°2θ±0.2°2θ. The diffractogram comprises additional peaks at 12.8, 21.6, and 22.9°2θ±0.2°2θ. Form A also is characterized by its fill X-ray powder diffractogram as substantially shown in FIG. 1.

Figure 2:
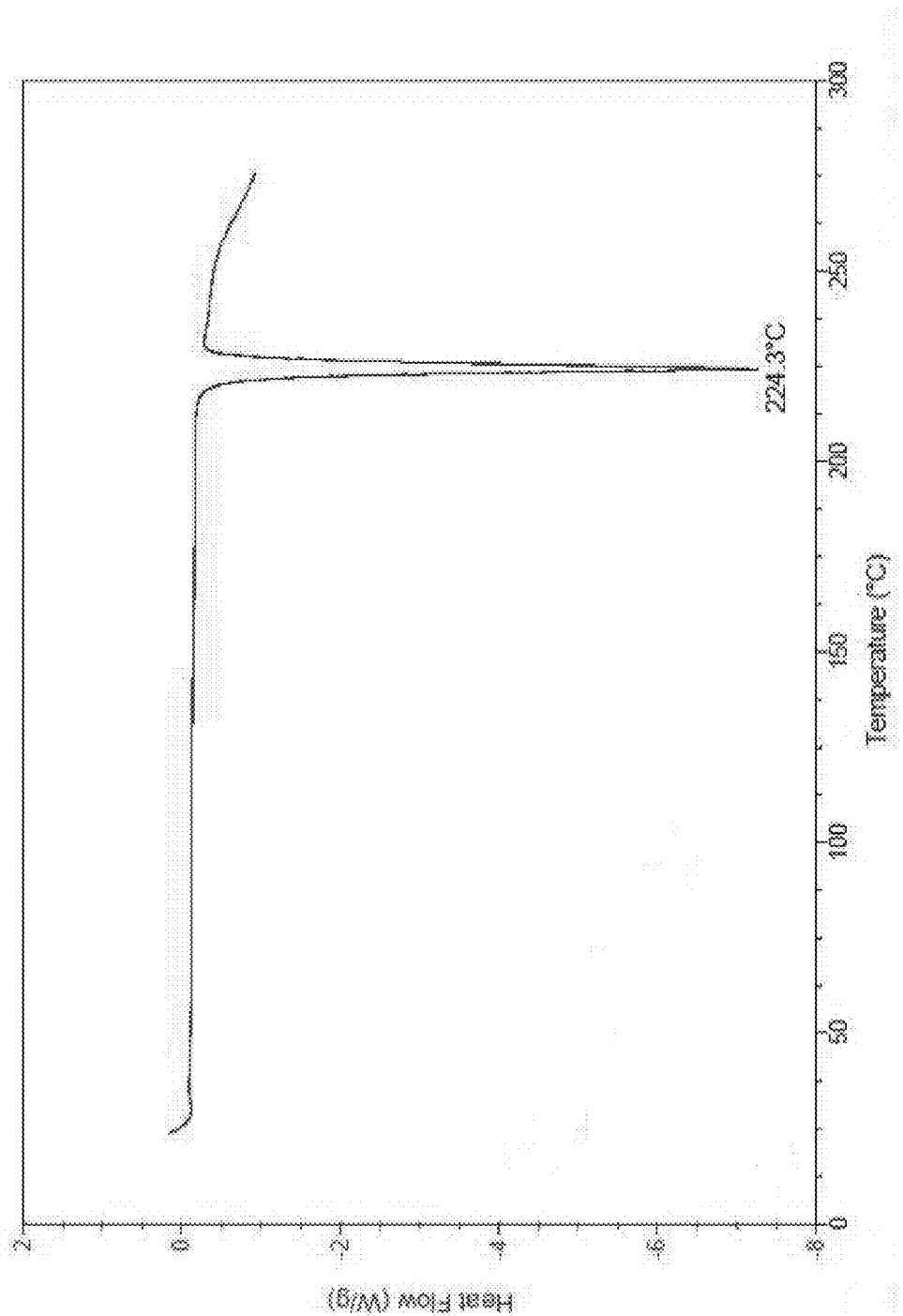
FIG. 2 is a differential scanning calorimetry (DSC) curve of Compound A Form A.

In some embodiments, Form A is characterized by its differential scanning calorimetry (DSC) curve that comprises an endotherm at about 223° C. Form A also is characterized by its full DSC curve as substantially as shown in FIG. 2.

Compound A Form B is characterized by its X-ray powder diffractogram that comprises peaks at 4.2, 8.3, and 16.6°2θ±0.2°2θ. The diffractogram comprises additional peaks at 12.5, 14.1, and 17.4°2θ±0.2°2θ. Form B also is characterized by its full X-ray powder diffractogram as substantially shown in FIG. 3.

Figure 4:
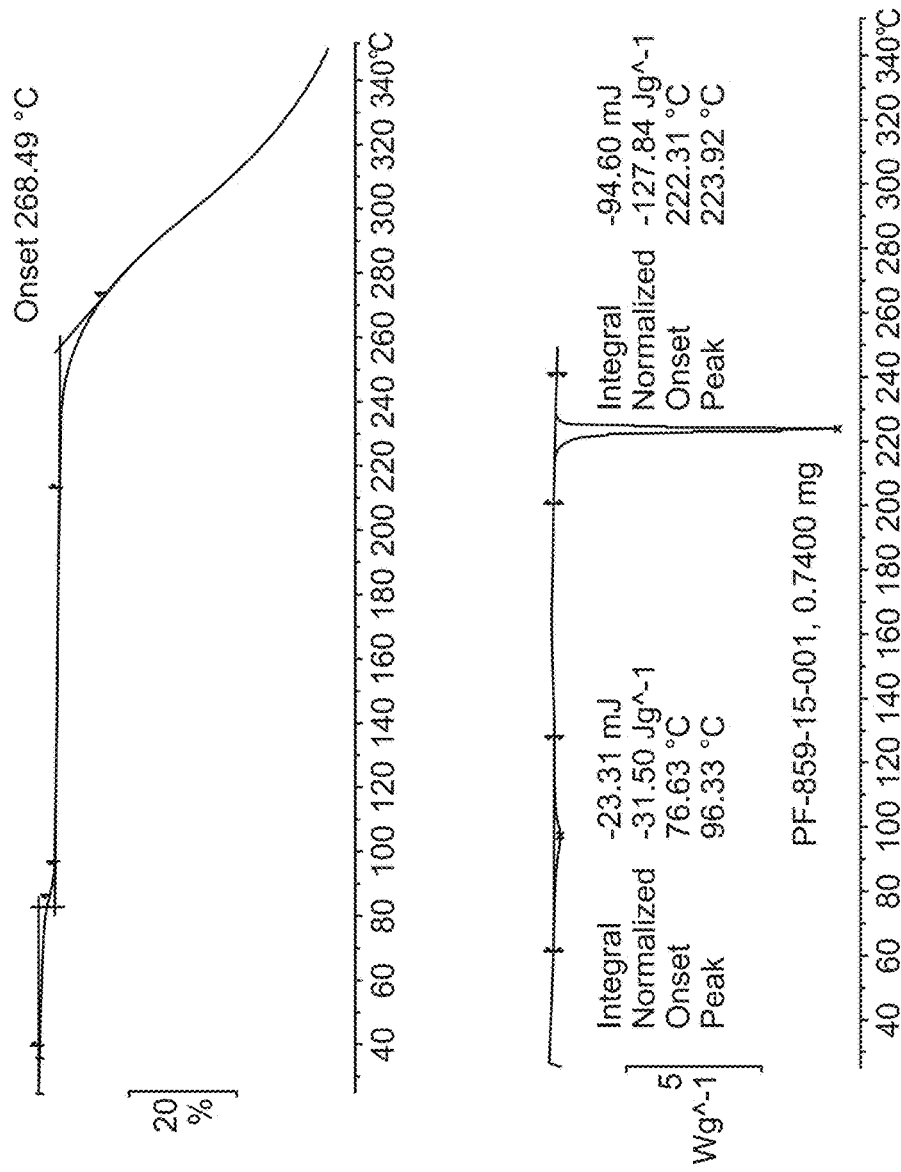
FIG. 4 is a thermogravimetric analysis (TGA) (top) and a differential scanning calorimetry (DSC) curve (bottom) of Compound A Form B.

In some embodiments, Form B is characterized by its differential scanning calorimetry (DSC) curve that comprises an endothermnn at about 222° C. Form B also is characterized by its full DSC curve as substantially as shown in FIG. 4.

Compound A Form C is characterized by its X-ray powder diffractogram that comprises peaks at 4.5, 13.7, and 16.4°2θ±0.2°2θ. The diffractogram comprises additional peaks at 15.4, 15.5, and 20.6°2θ±0.2°2θ. Form C also is characterized by its full X-ray powder diffractogram as substantially shown in FIG. 5.

Figure 6:
FIG. 6 is a differential scanning calorimetry (DSC) curve (top) and a thermogravimetric analysis (TGA) (bottom) of Compound A Form C.

In some embodiments, Form C is characterized by its differential scanning calorimetry (DSC) curve that comprises an endotherm at about 222° C. Form C also is characterized by its full DSC curve as substantially as shown in FIG. 6.

Figure 7:
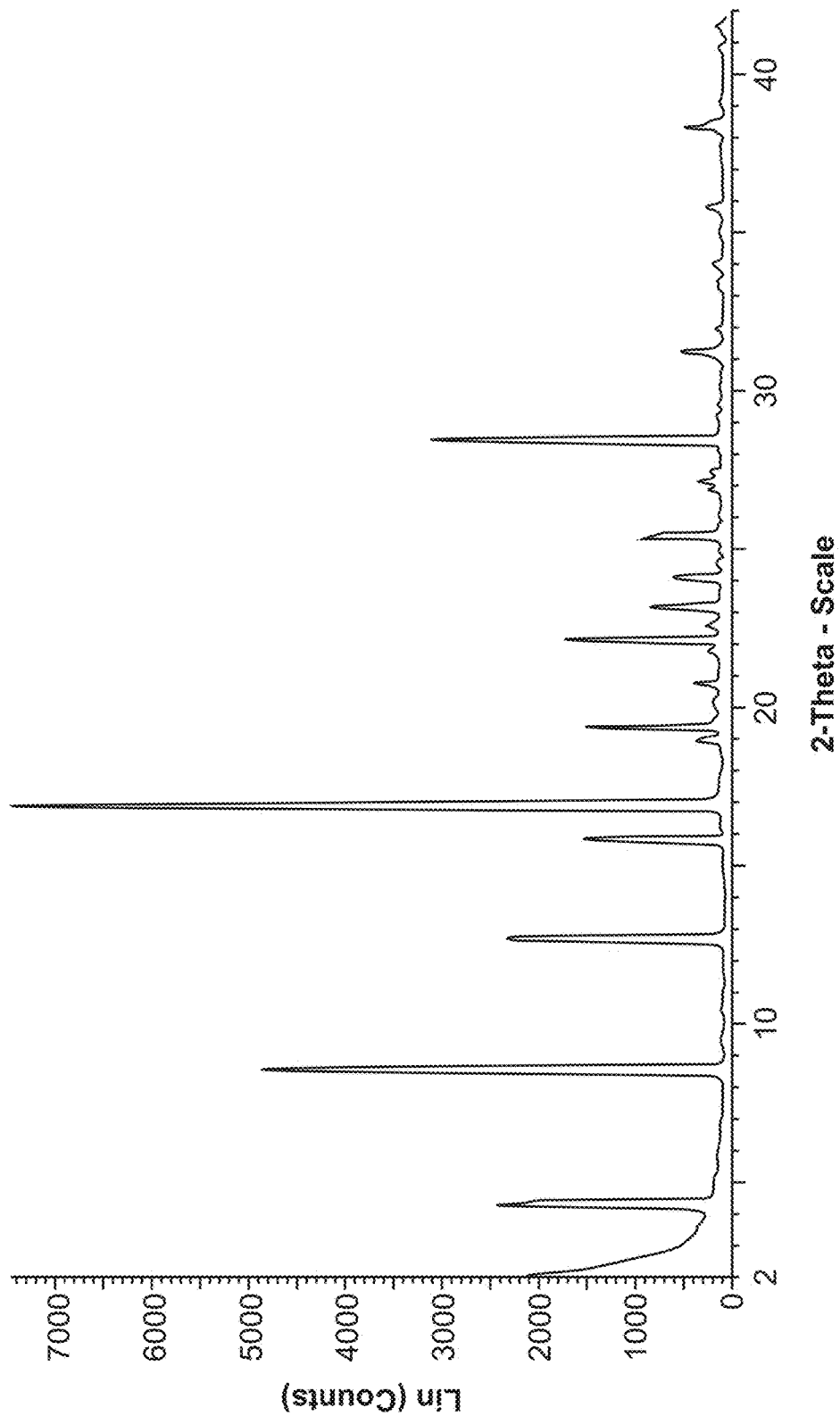
FIG. 7 is an X-ray powder diffraction pattern of Compound A Form D.

Compound A Form D is characterized by its X-ray powder diffractogram that comprises peaks at 8.4, 8.5, and 16.8°2θ±0.2°2θ. The diffractogram comprises additional peaks at 4.2, 12.6, and 28.4°2θ±0.2°2θ. Form D also is characterized by its full X-ray powder diffractogram as substantially shown in FIG. 7.

Figure 8:
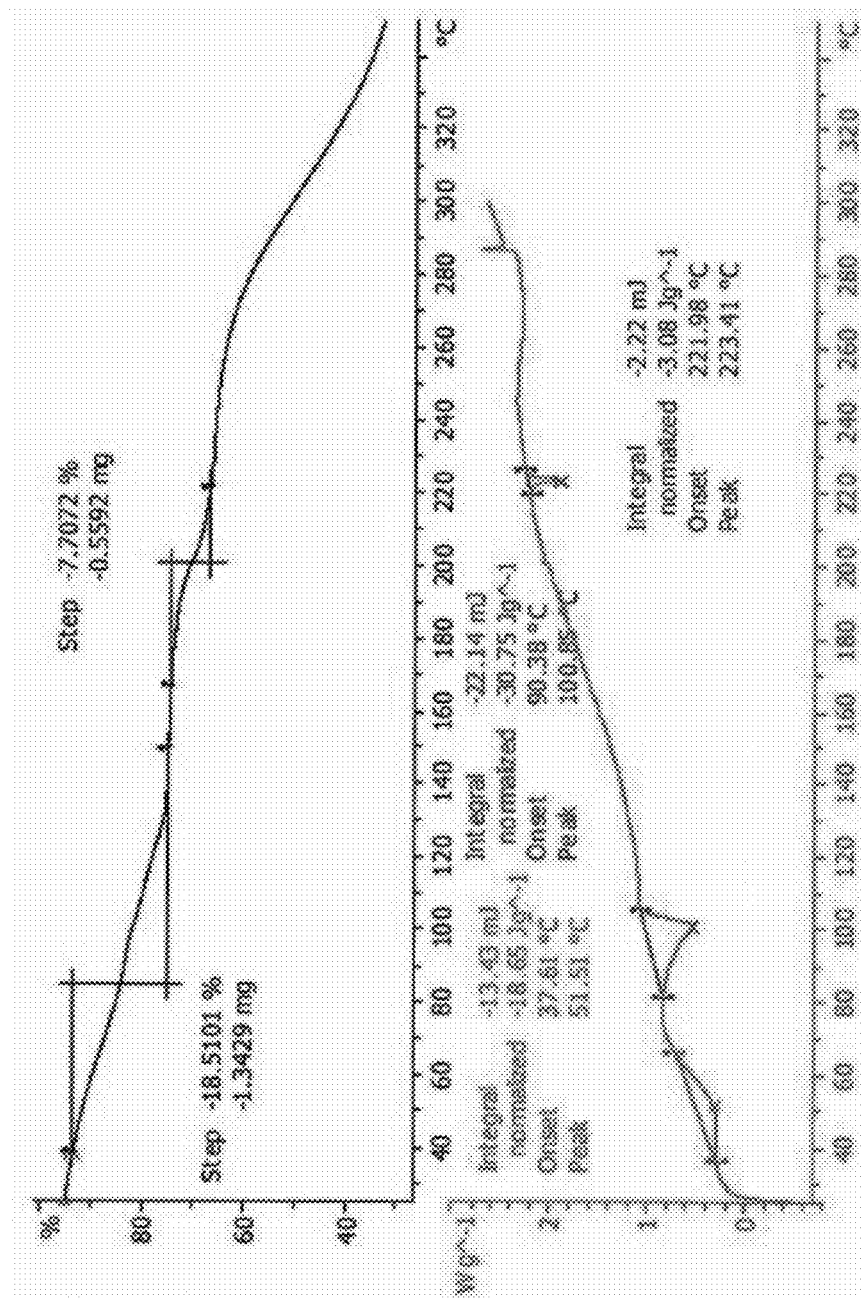
FIG. 8 is a thermogravimetric analysis (TGA) (top) and a differential scanning calorimetry (DSC) curve (bottom) of Compound A Form D.

In some embodiments, Form D is characterized by its differential scanning calorimetry (DSC) curve that comprises an endotherm at about 222° C. Form D also is characterized by its full DSC curve as substantially as shown in FIG. 8.

Compound A sodium salt is characterized by its X-ray powder diffractogram that comprises peaks at 5.3, 16.0, and 21.6°2θ±0.2°2θ. The diffractogram comprises additional peaks at 18.7, 19.2, and 24.0°2θ±0.2°2θ. Compound A sodium salt also is characterized by its full X-ray powder diffractogram as substantially shown in FIG. 9.

Figure 10:
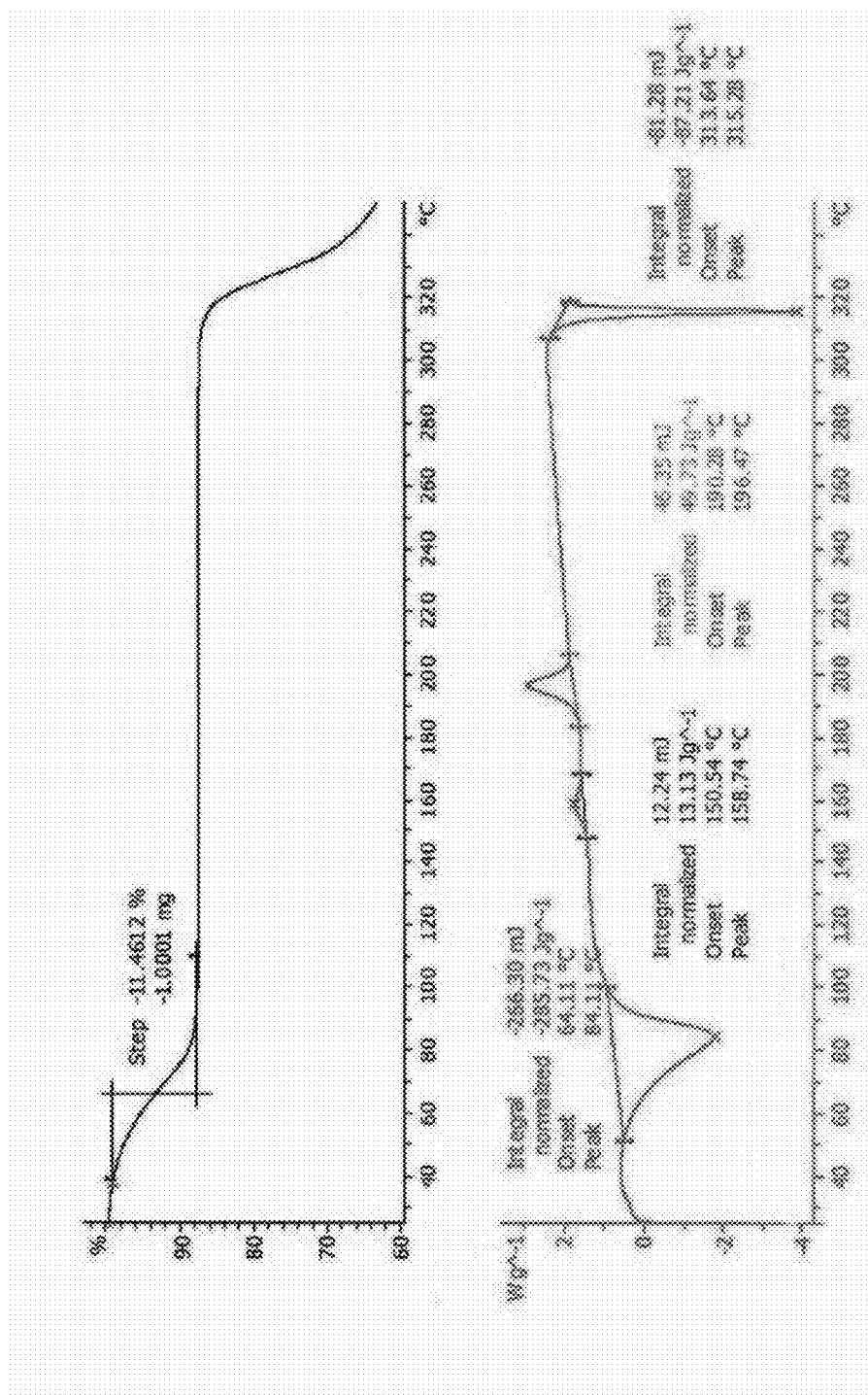
FIG. 10 is a thermogravimetric analysis (TGA) (top) and a differential scanning calorimetry (DSC) curve (bottom) of Compound A sodium salt.

In some embodiments, Compound A sodium salt is characterized by its differential scanning calorimetry (DSC) curve that comprises an endotherm at about 314° C. Compound A sodium salt also is characterized by its fill DSC curve as substantially as shown in FIG. 10.

Compound A L-arginine salt is characterized by its X-ray powder diffractogram that comprises peaks at 20.8, 21.8, and 25.4°2θ±0.2°2θ. The diffractogram comprises additional peaks at 22.7, 23.4, and 26.4°2θ±0.2°2θ. Compound A L-arginine salt also is characterized by its full X-ray powder diffractogram as substantially shown in FIG. 11.

Figure 12:
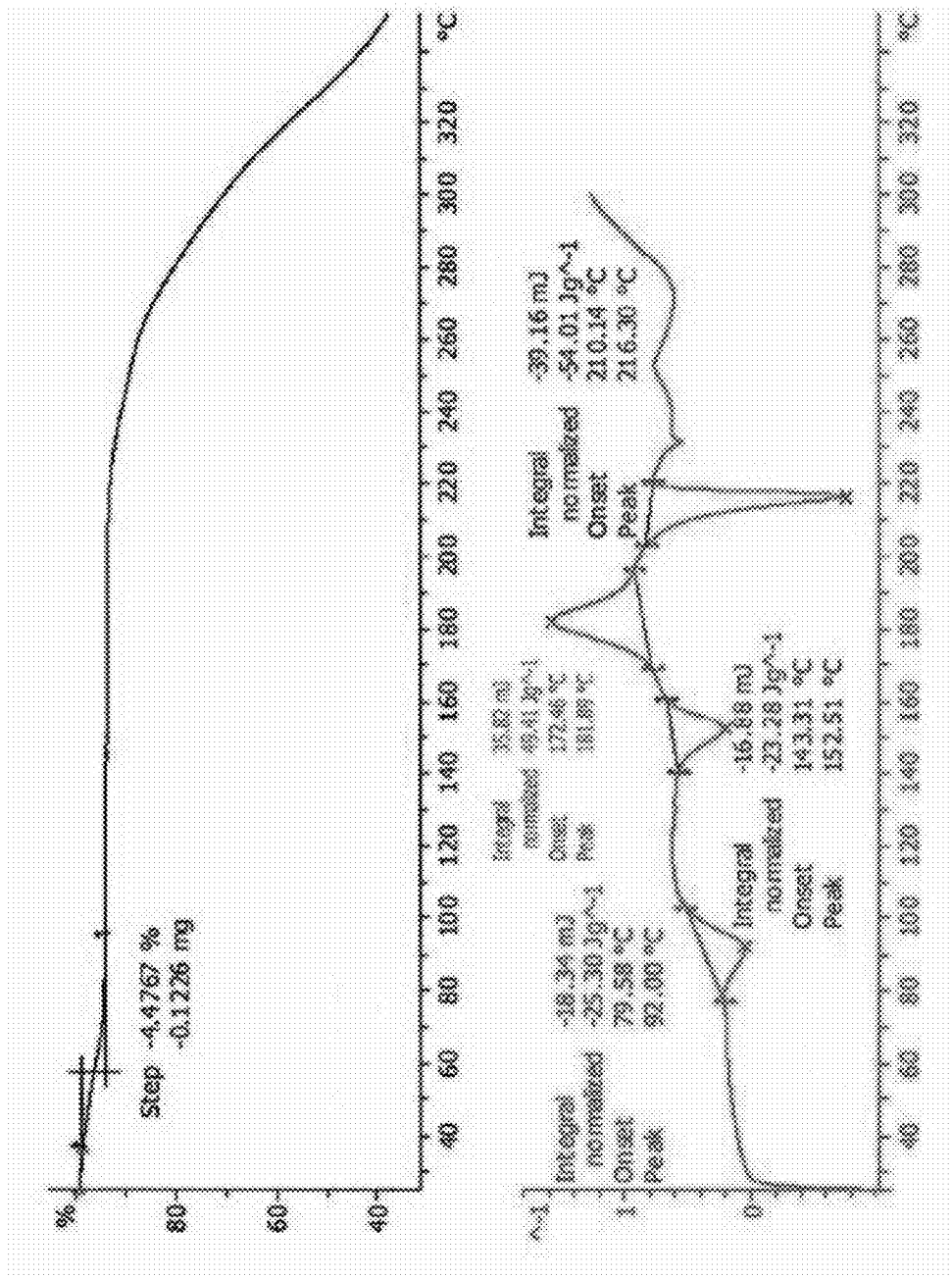
FIG. 12 is a thermogravimetric analysis (TGA) (top) and a differential scanning calorimetry (DSC) curve (bottom) of Compound A L-arginine salt.

In some embodiments, Compound A L-arginine salt is characterized by its differential scanning calorimetry (DSC) curve that comprises an endotherm at about 210° C. Compound A L-arginine salt also is characterized by its full DSC curve as substantially as shown in FIG. 12.

Compound A L-lysine salt is characterized by its X-ray powder diffractogram that comprises peaks at 19.8, 20.7, and 21.2°2θ±0.2°2θ. The diffractogram comprises additional peaks at 10.2, 16.9, and 18.4°2θ±0.2°2θ. Compound A L-lysine salt also is characterized by its full X-ray powder diffractogram as substantially shown in FIG. 13.

Figure 14:
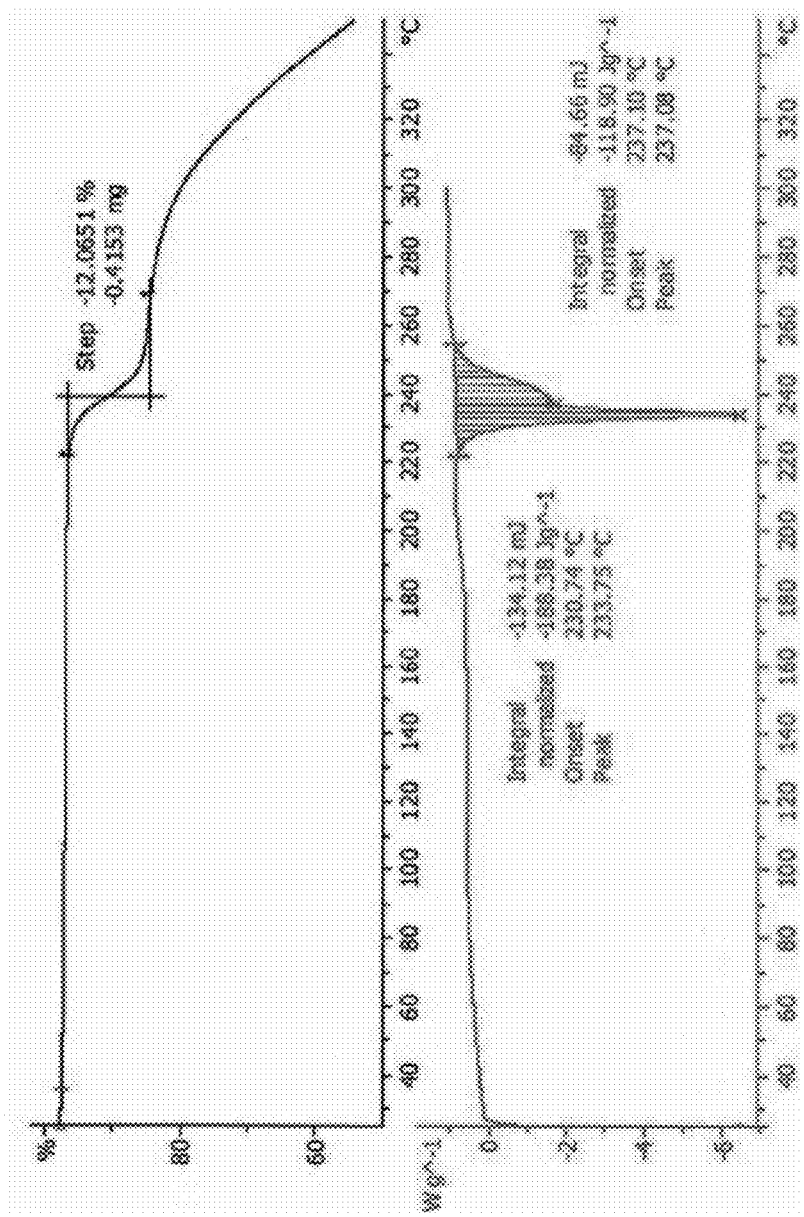
FIG. 14 is a thermogravimetric analysis (TGA) (top) and a differential scanning calorimetry (DSC) curve (bottom) of Compound A L-lysine salt.

In some embodiments, Compound A L-lysine salt is characterized by its differential scanning calorimetry (DSC) curve that comprises an endotherm at about 237° C. Compound A L-lysine salt also is characterized by its full DSC curve as substantially as shown in FIG. 14.

Compound A ethanolamine salt is characterized by its X-ray powder diffractogram that comprises peaks at 21.8, 22.7, and 27.1°2θ±0.2°2θ. The diffractogram comprises additional peaks at 21.1, 26.2, and 26.6°2θ±0.2°2θ. Compound A ethanolamine salt also is characterized by its full X-ray powder diffractogram as substantially shown in FIG. 15.

Figure 16:
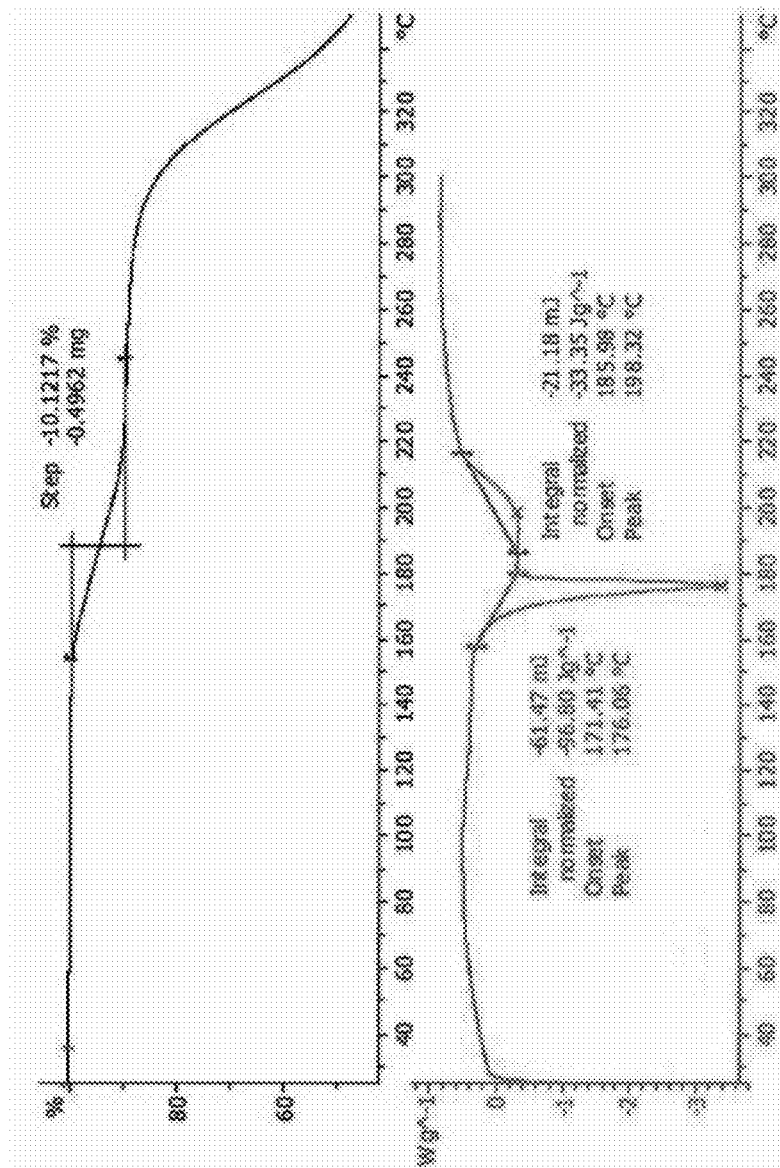
FIG. 16 is a thermogravimetric analysis (TGA) (top) and a differential scanning calorimetry (DSC) curve (bottom) of Compound A ethanolamine salt.

In some embodiments, Compound A ethanolamine salt is characterized by its differential scanning calorimetry (DSC) curve that comprises an endotherm at about 171° C. Compound A ethanolamine salt also is characterized by its full DSC curve as substantially as shown in FIG. 16.

Compound A diethanolamine salt is characterized by its X-ray powder diffractogram that comprises peaks at 16.9, 23.7, and 25.0°2θ±0.2°2θ. The diffractogram comprises additional peaks at 19.6, 22.6, and 26.0°2θ±0.2°2θ. Compound A diethanolamine salt also is characterized by its full X-ray powder diffractogram as substantially shown in FIG. 17.

Figure 18:
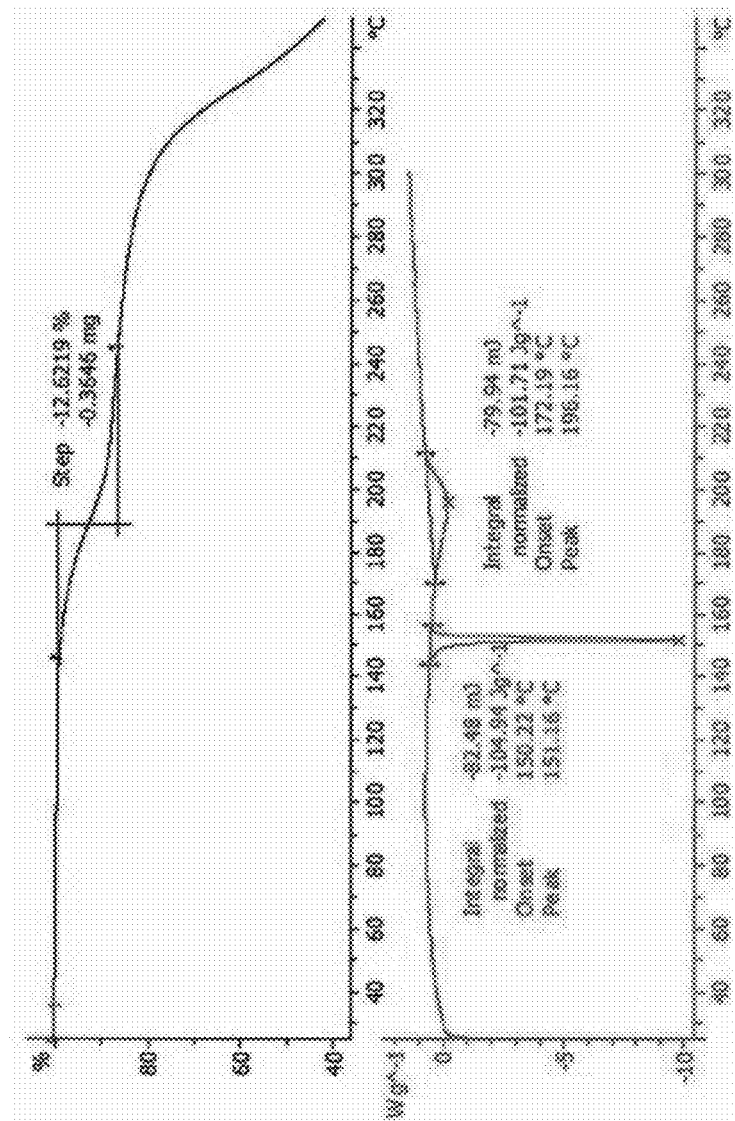
FIG. 18 is a thermogravimetric analysis (TGA) (top) and a differential scanning calorimetry (DSC) curve (bottom) of Compound A diethanolamine salt.

In some embodiments, Compound A diethanolamine salt is characterized by its differential scanning calorimetry (DSC) curve that comprises an endotherm at about 150° C. Compound A diethanolamine salt also is characterized by its full DSC curve as substantially as shown in FIG. 18.

Compound A tromethamine salt is characterized by its X-ray powder diffractogram that comprises peaks at 10.1, 14.2, and 21.1°2θ±0.2°2θ. The diffractogram comprises additional peaks at 20.1, 25.7, and 28.4°2θ±0.2°2θ. Compound A tromethamine salt also is characterized by its full X-ray powder diffractogram as substantially shown in FIG. 19.

Figure 20:
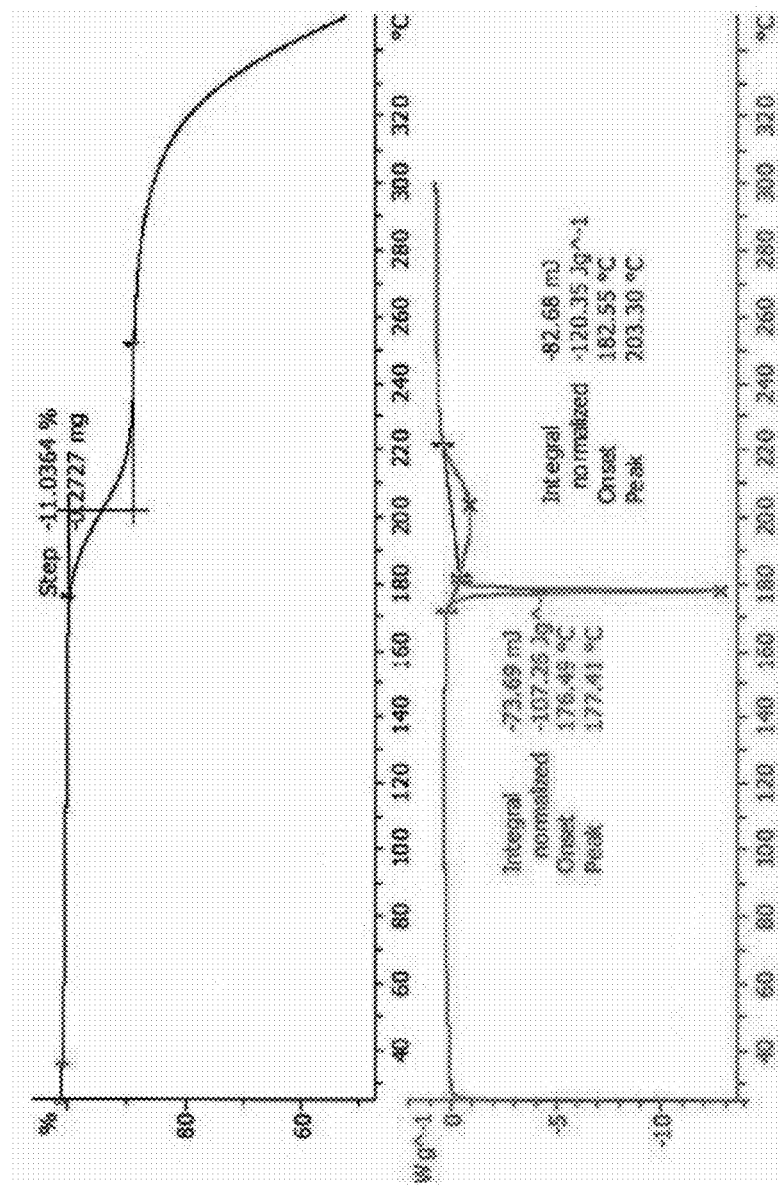
FIG. 20 is a thermogravimetric analysis (TGA) (top) and a differential scanning calorimetry (DSC) curve (bottom) of Compound A tromethamine salt.

In some embodiments, Compound A tromethamine salt is characterized by its differential scanning calorimetry (DSC) curve that comprises an endotherm at about 176° C. Compound A tromethamine salt also is characterized by its full DSC curve as substantially as shown in FIG. 20.

Figure 22:
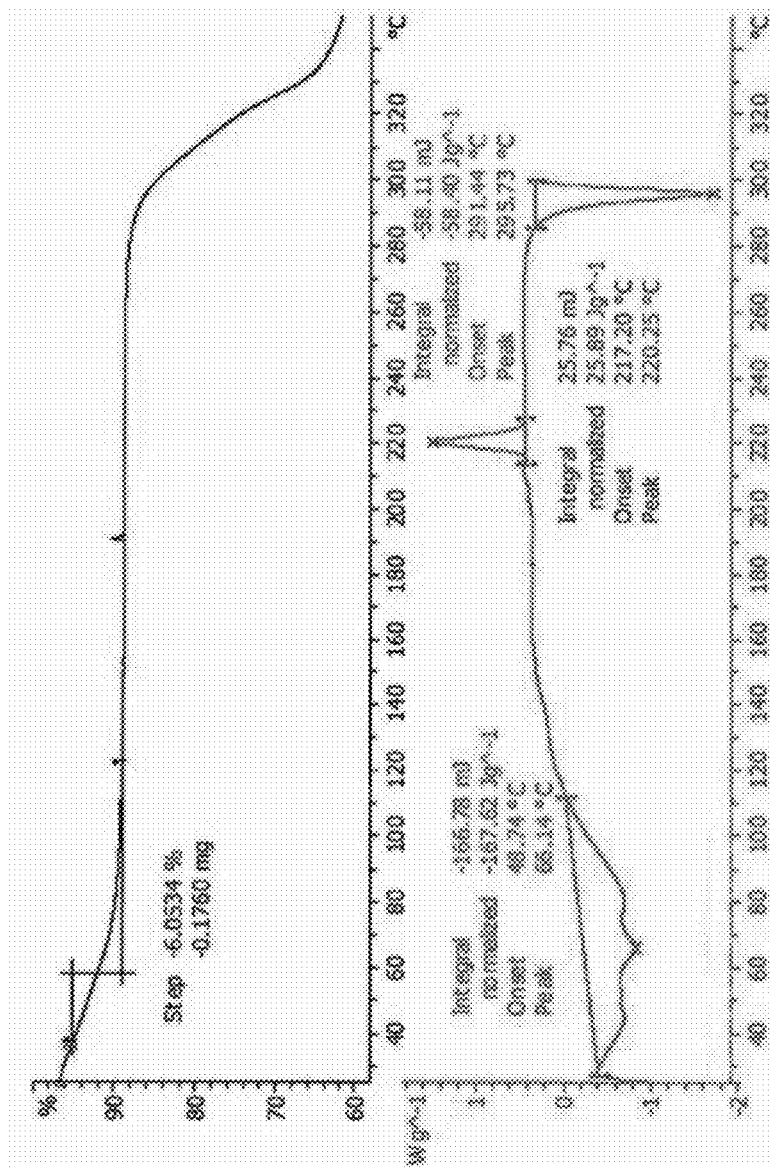
FIG. 22 is a thermogravimetric analysis (TGA) (top) and a differential scanning calorimetry (DSC) curve (bottom) of Compound A potassium salt.

Also provided is amorphous [(4-hydroxy-1-methyl-7-phenoxy-isoquinoline-3-carbonyl)-amino]-acetic acid (amorphous Compound A) and substantially amorphous [(4-hydroxy-1-methyl-7-phenoxy-isoquinoline-3-carbonyl)-amino]-acetic acid potassium salt (Compound A potassium salt). The substantially amorphous Compound A potassium salt has been characterized by a differential scanning calorimetry (DSC) curve that comprises an endotherm at about 291° C. (FIG. 22).

As described in the Examples below. Form A is the most stable crystalline form among Form B, C, and D) of Compound A.

3. Pharmaceutical Compositions, Formulations and Routes of Administration

In one aspect, the present disclosure is directed to a pharmaceutical composition comprising one or more crystalline forms of [(4-hydroxy-1-methyl-7-phenoxy-isoquinoline-3-carbonyl)-amino]-acetic acid (Compound A) having the following structure:

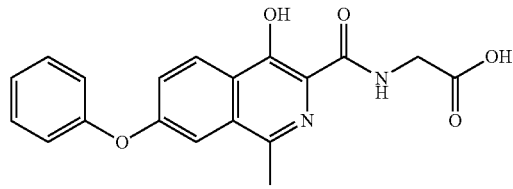

Compound A or a salt thereof, and at least one pharmaceutically acceptable excipient.

In one embodiment, the pharmaceutical composition comprises a compound selected from the group consisting of: Compound A Form A, Compound A Form B, Compound A Form C, Compound A Form D, Compound A sodium salt, Compound A L-arginine salt, Compound A L-lysine salt, Compound A ethanolamine salt. Compound A diethanolamine salt, Compound A tromethamine salt, amorphous Compound A, and Compound A potassium salt, as described generally above, and at least one pharmaceutically acceptable excipient.

In one embodiment, the pharmaceutical composition comprises Compound A in Form A. In one embodiment, the pharmaceutical composition comprises Compound A wherein at least about 85% of Compound A is in Form A. In one embodiment, the pharmaceutical composition comprises Compound A wherein at least about 90% of Compound A is in Form A. In one embodiment, the pharmaceutical composition comprises Compound A wherein at least about 95% of Compound A is in Form A. In one embodiment, the pharmaceutical composition comprises Compound A wherein at least about 99% of Compound A is in Form A. In one embodiment, the pharmaceutical composition comprises Compound A wherein at least about 99.5% of Compound A is in Form A. In one embodiment, the pharmaceutical composition comprises Compound A wherein at least about 99.9% of Compound A is in Form A. In one embodiment, the pharmaceutical composition comprises Compound A wherein at least about 99.99% of Compound A is in Form A.

In one embodiment, the pharmaceutical composition further comprises an additional therapeutic agent selected from the group consisting of vitamin B12, folic acid, ferrous sulfate, recombinant human erythropoietin, and an erythropoiesis stimulating agent (ESA). In another embodiment, the pharmaceutical composition is formulated for oral delivery. In another embodiment, the pharmaceutical composition is formulated as a tablet or a capsule.

The crystalline forms of the present disclosure can be delivered directly or in pharmaceutical compositions along with suitable excipients, as is well known in the art. Various treatments embodied herein can comprise administration of an effective amount of a crystalline form of the disclosure to a subject in need, e.g., a subject having or at risk for anemia due to, e.g., chronic renal failure, diabetes, cancer, AIDS, radiation therapy, chemotherapy, kidney dialysis, or surgery. In one embodiment, the subject is a mammalian subject, and in one embodiment, the subject is a human subject.

An effective amount of a crystalline form can readily be determined by routine experimentation, as can the most effective and convenient route of administration and the most appropriate formulation. In one embodiment, the dosage may be from 0.05 mg/kg to about 700 mg/kg per day. Typically, the dosage may be from about 0.1 mg/kg to about 500 mg/kg; from about 0.5 mg/kg to about 250 mg/kg; from about 1 mg/kg to about 100 mg/kg; from about 1 mg/kg to about 10 mg/kg; from about 1 mg/kg to about 5 mg/kg; or from about 1 mg/kg to about 2 mg/kg. For example, the dosage may be about 1.0 mg/kg; about 1.2 mg/kg; about 1.5 mg/kg; about 2.0 mg/kg; or about 2.5 mg/kg. Various formulations and drug delivery systems are available in the art (see, e.g., Gennaro, A. R., ed. (1995) Remington's Pharmaceutical Sciences).

Suitable routes of administration may, for example, include oral, rectal, transmucosal, nasal, or intestinal administration and parenteral delivery, including intramuscular, subcutaneous, intramedullary injections, as well as intrathecal, direct intraventricular, intravenous, intraperitoneal, intranasal, or intraocular injections. The crystalline form or composition thereof may be administered in a local rather than a systemic manner. For example, a crystalline form or composition thereof can be delivered via injection or in a targeted drug delivery system, such as a depot or sustained release formulation. In one embodiment, the route of administration is oral.

The pharmaceutical compositions of the present disclosure may be manufactured by any of the methods well-known in the art, such as by conventional mixing, dissolving, granulating, dragee-making, levigating, emulsifying, encapsulating, entrapping, or lyophilizing processes. As noted above, the compositions can include one or more pharmaceutically acceptable excipients that facilitate processing of active molecules into preparations for pharmaceutical use.

Proper formulation is dependent upon the route of administration chosen. For injection, for example, the composition may be formulated in aqueous solutions, preferably in physiologically compatible buffers such as Hanks' solution. Ringer's solution, or physiological saline buffer. For transmucosal or nasal administration, penetrants appropriate to the barrier to be permeated are used in the formulation. Such penetrants are generally known in the art. In a preferred embodiment of the present disclosure, the present crystalline forms are prepared in a formulation intended for oral administration. For oral administration, it can be formulated readily by combining the crystalline forms with pharmaceutically acceptable excipients well known in the art. Such excipients enable the crystalline forms of the disclosure to be formulated as tablets, pills, dragees, capsules, liquids, gels, syrups, slurries, suspensions and the like, for oral ingestion by a subject. The crystalline forms may also be formulated in rectal compositions such as suppositories or retention enemas, e.g., containing conventional suppository bases such as cocoa butter or other glycerides.

Pharmaceutical preparations for oral use can be obtained using solid excipients, optionally grinding a resulting mixture, and processing the mixture of granules, after adding suitable auxiliaries, if desired, to obtain tablets or dragee cores. Suitable excipients are, for example, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, microcrystalline cellulose and/or polyvinylpyrrolidone (PVP or povidone). If desired, disintegrating agents may be added, such as the cross-linked polyvinyl pyrrolidone, agar, croscarmellose sodium or alginic acid or a salt thereof such as sodium alginate. Also, wetting agents such as sodium dodecyl sulfate or lubricants such as magnesium stearate may be included.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the crystalline forms may be dissolved or suspended in suitable liquids, such as fatty oils, liquid paraffin, or liquid polyethylene glycols. In addition, stabilizers may be added. All formulations for oral administration should be in dosages suitable for such administration.

In one embodiment, the crystalline forms described herein can be administered transdermally, such as through a skin patch, or topically. In one aspect, the transdermal or topical formulations can additionally comprise one or multiple penetration enhancers or other effectors, including agents that enhance migration of the delivered compound. Transdermal or topical administration could be preferred, for example, in situations in which location specific delivery is desired.

For administration by inhalation, the crystalline forms for use according to the present disclosure are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges of, for example, gelatin, for use in an inhaler or insufflator may be formulated. These typically contain a powder mix of the crystalline form and a suitable powder base such as lactose or starch.

Compositions formulated for parenteral administration by injection, e.g., by bolus injection or continuous infusion can be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents. Formulations for parenteral administration include aqueous solutions or other compositions in water-soluble form.

Suspensions of the crystalline forms may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the crystalline forms to allow for the preparation of highly concentrated solutions. Alternatively, the active ingredient may be in powder form for constitution with a suitable vehicle, e.g., sterile pyrogen-free water, before use.

As mentioned above, the compositions of the present disclosure may also be formulated as a depot preparation. Such long acting formulations may be administered by implantation (for example, subcutaneously or intramuscularly) or by intramuscular injection. Thus, for example, the present crystalline forms may be formulated with suitable polymeric or hydrophobic materials (for example as an emulsion in an acceptable oil) or ion exchange resins, or as sparingly soluble derivatives, for example, as a sparingly soluble salt.

For any composition used in the various treatments embodied herein, a therapeutically effective dose can be estimated initially using a variety of techniques well known in the art. For example, in a cell culture assay, a dose can be formulated in animal models to achieve a circulating concentration range that includes the $IC_{50}$ as determined in cell culture. Dosage ranges appropriate for human subjects can be determined, for example, using data obtained from cell culture assays and non-human animal studies. In one embodiment, the dosage may be from 0.05 mg/kg to about 700 mg/kg administered periodically. The dosage may be administered once a day, every other day, one, two or three times a week, or at other appropriate intervals as can be readily determined by competent medical practitioners. Typically the dosage is administered 2 or 3 times a week. Typically, the dosage may be from about 0.1 mg/kg to about 500 mg/kg; from about 0.5 mg/kg to about 250 mg/kg; from about 1 mg/kg to about 100 mg/kg; from about 1 mg/kg to about 10 mg/kg; from about 1 mg/kg to about 5 mg/kg; or from about 1 mg/kg to about 2 mg/kg. For example, the dosage may be about 1.0 mg/kg; about 1.2 mg/kg; about 1.5 mg/kg; about 2.0 mg/kg; or about 2.5 mg/kg.

A therapeutically effective dose of a compound refers to that amount of the compound that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Compounds that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

Dosage amount and interval may be adjusted individually to provide plasma levels of the active moiety that are sufficient to modulate a desired parameter, e.g., endogenous erythropoietin plasma levels, i.e. minimal effective concentration (MEC). The MEC will vary for each compound but can be estimated from, for example, in vitro data. Dosages necessary to achieve the MEC will depend on individual characteristics and route of administration. Compounds or compositions thereof should be administered using a regimen which maintains plasma levels above the MEC for about 10-90% of the duration of treatment, preferably about 30-90% of the duration of treatment, and most preferably between 50-90%. In cases of local administration or selective uptake, the effective local concentration of the drug may not be related to plasma concentration. Alternatively, modulation of a desired parameter, e.g., stimulation of endogenous erythropoietin, may be achieved by 1) administering a loading dose followed by a maintenance dose, 2) administering an induction dose to rapidly achieve the desired parameter, e.g., erythropoietin levels, within a target range, followed by a lower maintenance dose to maintain, e.g., hematocrit, within a desired target range, or 3) repeated intermittent dosing.

The amount of compound or composition administered will, of course, be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a crystalline form of the disclosure formulated in a compatible pharmaceutical excipient may also be prepared, placed in an appropriate container, and labeled for treatment of an indicated condition. Suitable conditions indicated on the label may include treatment of conditions, disorders, or diseases in which anemia is a major indication.

4. Method of Use

One aspect of the disclosure provides for use of one or more of a crystalline or amorphous form of [(4-hydroxy-1-methyl-7-phenoxy-isoquinoline-3-carbonyl)-amino]-acetic acid (Compound A), or a composition comprising one or more crystalline or amorphous forms of Compound A or a solvate or salt thereof, for the manufacture of a medicament for use in treating various conditions or disorders as described herein. It also provides methods of using the crystalline or amorphous form, or composition or medicament thereof to treat, pretreat, or delay progression or onset of various conditions or disorders as described herein. In one embodiment, the crystalline form of Compound A used in the method is Form A. In one embodiment, the crystalline form of Compound A used in the method is Form B. Form C or Form D. As used in this section "Method of Use" and the corresponding method claims, "compound" refers to a crystalline or amorphous form of Compound A, or a solvate or salt thereof.

In one embodiment, at least about 85% of the compound used in the method is Compound A Form A. In one embodiment, at least about 90% of the compound used in the method is Compound A Form A. In one embodiment, at least about 95% of the compound used in the method is Compound A Form A. In one embodiment, at least about 99% of the compound used in the method is Compound A Form A. In one embodiment, at least about 99.5% of the compound used in the method is Compound A Form A. In one embodiment, at least about 99.9% of the compound used in the method is Compound A Form A. In one embodiment, at least about 99.99% of the compound used in the method is Compound A Form A.

The medicaments or compositions can be used to modulate the stability and/or activity of HIF, and thereby activate HIF-regulated gene expression. The crystalline or amorphous form, or composition or medicament thereof, can be used in methods to treat, pretreat, or delay progression or onset of conditions associated with HIF including, but not limited to, anemic, ischemic, and hypoxic conditions. In various embodiments, the crystalline or amorphous form, or composition or medicament thereof, is administered immediately following a condition producing acute ischemia, e.g., myocardial infarction, pulmonary embolism, intestinal infarction, ischemic stroke, and renal ischemic-reperfusion injury. In another embodiment, the crystalline or amorphous form, or composition or medicament thereof, is administered to a patient diagnosed with a condition associated with the development of chronic ischemia, e.g., cardiac cirrhosis, macular degeneration, pulmonary embolism, acute respiratory failure, neonatal respiratory distress syndrome, and congestive heart failure. In yet another embodiment, the crystalline or amorphous form, or composition or medicament thereof, is administered immediately after a trauma or injury. In other embodiments, the crystalline or amorphous form, or composition or medicament thereof, can be administered to a subject based on predisposing conditions, e.g., hypertension, diabetes, occlusive arterial disease, chronic venous insufficiency, Raynaud's disease, chronic skin ulcers, cirrhosis, congestive heart failure, and systemic sclerosis. In still other embodiments, the crystalline or amorphous form, or composition or medicament thereof, may be administered to pretreat a subject to decrease or prevent the development of tissue damage associated with ischemia or hypoxia.

The crystalline or amorphous firm, or compositions or medicaments thereof, can also be used to increase endogenous erythropoietin (EPO). The crystalline or amorphous form, or composition or medicament thereof, can be administered to prevent, pretreat, or treat EPO-associated conditions, including, e.g., conditions associated with anemia and neurological disorders. Conditions associated with anemia include disorders such as acute or chronic kidney disease, diabetes, cancer, ulcers, infection with virus, e.g., HIV, bacteria, or parasites; inflammation, etc. Anemic conditions can further include those associated with procedures or treatments including, e.g., radiation therapy, chemotherapy, dialysis, and surgery. Disorders associated with anemia additionally include abnormal hemoglobin and/or erythrocytes, such as found in disorders such as microcytic anemia, hypochromic anemia, aplastic anemia, etc.

The disclosure is also directed to use of a crystalline or amorphous form, or composition or medicament thereof, to treat, pretreat, or delay onset of a condition associated with a disorder selected from the group consisting of anemic disorders; neurological disorders and/or injuries including cases of stroke, trauma, epilepsy, and neurodegenerative disease, cardiac ischemia including, but not limited to, myocardial infarction and congestive heart failure; liver ischemia including, but not limited to, cardiac cirrhosis; renal ischemia including, but not limited to, acute kidney failure and chronic kidney failure; peripheral vascular disorders, ulcers, burns, and chronic wounds; pulmonary embolism; and ischemic-reperfusion injury.

The disclosure is also directed to a method of inhibiting the activity of at least one hydroxylase enzyme which modifies the alpha subunit of hypoxia inducible factor. The HIF hydroxylase enzyme may be a prolyl hydroxylase including, but not limited to, the group consisting of EGLN1, EGLN2, and EGLN3 (also known as PHD2, PHD1 and PHD3, respectively), described by Taylor (2001, Gene 275:125-132), and characterized by Aravind and Koonin (2001, Genome Biol 2:RESEARCH0007), Epstein et al. (2001, Cell 107:43-54), and Bruick and McKnight (2001, Science 294:1337-1340). The method comprises contacting the enzyme with an inhibiting effective amount of one or more crystalline or amorphous form of Compound A. In some embodiments, the HIF hydroxylase enzyme is an asparaginyl hydroxylase or a prolyl hydroxylase. In other embodiments, the HIF hydroxylase enzyme is a factor inhibiting HIF, human EGLN1, EGLN2, or EGLN3.

While this disclosure has been described in conjunction with specific embodiments and examples, it will be apparent to a person of ordinary skill in the art, having regard to that skill and this disclosure, that equivalents of the specifically disclosed materials and methods will also be applicable to this disclosure; and such equivalents are intended to be included within the following claims.

EXAMPLES

Unless otherwise stated, the following abbreviations used throughout the specification have the following definitions:

| | |
|---|---|
| ° C. | Degree Celsius |
| Ac | Acetyl |
| ca. | About |
| d | Doublet |
| dd | Doublet of doublets |
| DMA | Dimethylamine |
| DMEM | Eagle's minimal essential medium |
| DMF | Dimethylformamide |
| DMSO | Dimethylsulfoxide |
| DSC | Differential scanning calorimetry |
| EDTA | Ethylenediaminetetraacetic acid |
| EtOAc | Ethyl Acetate |
| eq. | Equivalents |
| FBS | Fetal bovine serum |
| g | Gram |
| Gly | Glycine |
| h | Hour |
| HEPES | 4-(2-hydroxyethyl)-1-piperazineethanesulfonic acid |
| HPLC | High performance liquid chromatography |
| IPA | Isopropyl alcohol |
| iPrOAc | Isopropylacetate |
| J | Joules |
| J | Coupling constant |
| kg | Kilogram |
| kV | Kilovolts |
| m | Multiplet |
| M | Molar |
| M+ | Mass peak |
| mA | Milliamps |
| Me | Methyl |
| MEC | Minimal effective concentration |
| MeCN | Acetonitrile |
| MEK | Methyl ethyl ketone |
| mg | Milligram |
| MHz | Megahertz |
| MIBK | Methyl iso-butyl ketone |
| min | Minute |
| mIU | Milliinternational units |
| mL | Milliliter |
| mm | Millimeter |
| mM | Millimolar |
| mol | Mole |
| MS | Mass spectroscopy |
| NMR | Nuclear magnetic resonance |
| PBS | Phosphate buffer system |
| Ph | Phenyl |
| RH | Relative humidity |
| rpm | Revolutions per minute |
| s | Singlet |
| s | Second |
| TEA | Triethylamine |
| TGA | Thermogravimetric analysis |
| THF | Tetrahydrofuran |
| Ts | Tosyl |
| vol | Volume |
| w | weight |
| XRPD | X-ray powder diffraction |
| δ | Chemical shift |
| μL | Microliter |
| μM | Micromolar |

X-Ray Powder Diffraction (XRPD)

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Gobel multilayer mirror coupled with a pinhole collimator of 0.3 mm. A weekly performance check is carried out using a certified standard NIST 1976 Corundum (flat plate).

The beam divergence, i.e. the effective size of the X-ray beam on the sample, was approximately 4 mm. A θ-θ continuous scan mode was employed with a sample—detector distance of 20 cm which gives an effective 2θ range of 3.2°-29.7°. Typically the sample would be exposed to the X-ray beam for 120 seconds. The software used for data collection was GADDS for WNT 4.1.16 and the data were analyzed and presented using Diffrac Plus EVA v11.0.0.2 or v13.0.0.2.

Alternatively, X-Ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.5.0 and the data were analyzed and presented using Diffrac Plus EVA v11.0.0.2 or v13.0.0.2.

Samples were run under ambient conditions as flat plate specimens using powder as received. The sample was gently packed into a cavity cut into polished, zero-background (510) silicon wafer. The sample was rotated in its own plane during analysis. The details of the data collection are:
Angular range: 2 to 42°2θ
Step size: 0.05°2θ
Collection time: 0.5 s/step
Analysis duration: 7 minutes Differential Scanning Calorimetry (DSC)

DSC was were collected on a TA Instruments Q2000 equipped with a 50 position autosampler. The calibration for thermal capacity was carried out using sapphire and the calibration for energy and temperature was carried out using certified indium. Typically 0.5-3 mg of each sample, in a pin-holed aluminum pan, was heated at 10° C./min from 25° C. to 300° C. A purge of dry nitrogen at 50 ml/min was maintained over the sample. Modulated temperature DSC was carried out using an underlying heating rate of 2° C./min and temperature modulation parameters of ±0.318° C. (amplitude) every 60 seconds (period). The instrument control software was Advantage for Q Series v2.8.0.392 and Thermal Advantage v4.8.3 and the data were analyzed using Universal Analysis v4.4A.

Alternatively, the DSC data was collected on a Mettler DSC 823e equipped with a 34 position auto-sampler. The instrument was calibrated for energy and temperature using certified indium. Typically 0.5-3 mg of each sample, in a pin-holed aluminum pan, was heated at 10° C./min from 25° C. to 300° C. or 25° C. to 320° C. A nitrogen purge at 50 ml/min was maintained over the sample. The instrument control and data analysis software was STARe v9.20.

Thermo-Gravimetric Analysis (TGA)

TGA data were collected on a Mettler TGNSDT A 851 e equipped with a 34 position autosampler. The instrument was temperature calibrated using certified indium. Typically, 1-30 mg of each sample was loaded onto a pre-weighed aluminum crucible and was heated at 10° C./min from ambient temperature to 350° C. A nitrogen purge at 50 ml/min was maintained over the sample. The instrument control and data analysis software was STARe v9.20.

Example 1

Preparation of Compound A Form A

Methods

The crystalline [(4-hydroxy-1-methyl-7-phenoxy-isoquinoline-3-carbonyl)-amino]-acetic acid (Compound A Form A) was prepared via the following methods.

Method I

The crystalline Compound A Form A (see Example 1, Method I) was used in this method. 15 mg of the crystalline material was used with each solvent added in increments until a clear solution had been obtained or until 50 volumes (750 μL) of solvent had been added. Samples were sonicated for 5 seconds after each solvent addition. When insoluble, the slurries were stirred at 500 rpm cycling between 25° C. and 50° C. (4 h at each temperature) for a period of from 16 hours to six days. Any resulting solutions were then allowed to evaporate at room temperature. The solids obtained from this experiment were analyzed by XRPD.

Each of the following solvents used in the above described Method I provided Form A: acetic acid, acetone, acetophenone, benzonitrile, benzyl alcohol, butyronitrile, chlorobenzene cyclohexanone, 1,2-dichlorobenzene, 1,2-dichloroethane, dimethoxyethane, dimethylacetamide. DMSO, 1,4-dioxane, ethylene glycol, EtOAc, formamide, hexafluorobenzene, hexane, IPA, IPA:10% water, iPrOAc, MeCN, MEK, MIBK, nitromethane, perfluorohexane, propionitrile, sulfolane, t-butyl methyl ether, t-butanol, tetraline, THF, and toluene.

Using Method I, hexafluoropropan-2-ol, methanol and ethanol did not provide Form A.

Method II

The crystalline Compound A Form A (see Example 1, Method VIII) was used in this method. 15 mg of the crystalline material was used with 30 volumes (450 μL) of solvent with the exception of DMSO and DMA where 5 volumes were used. Slurries were sonicated for 5 seconds. The slurries were stirred at 500 rpm at 5° C. for a period of six days. Any resulting solutions were then allowed to evaporate at room temperature. The solids obtained were analyzed by XRPD.

Each of the following solvents used in the above described Method II provided Form A: benzonitrile, sulfolane, formamide, tetraline, acetophenone, benzyl alcohol, ethylene glycol, 1,2-dichlorobenzene, chlorobenzene, cyclohexanone, butyronitrile, acetic acid, nitromethane, propionitrile, dimethoxyethane, 1,2-dichloroethane, hexafluorobenzene, t-butanol, hexane, and perfluorohexane.

Using Method II, hexafluoropropan-2-ol did not provide Form A.

Method III

The crystalline Compound A Form A (see Example 1, Method VIII) was used in this method. Method III is substantially as described in Method II, above, with the exception that the slurries were stirred at 500 rpm at 50° C. for a period of six days. The solids obtained were analyzed by XRPD.

Each of the following solvents used in the above described Method III provided Form A: benzonitrile, sulfolane, formamide, tetraline, acetophenone, benzyl alcohol, ethylene glycol, 1,2-dichlorobenzene, chlorobenzene, cyclohexanone, butyronitrile, acetic acid, nitromethane, propionitrile, dimethoxyethane, 1,2-dichloroethane, hexafluorobenzene, t-butanol, hexane, and perfluorohexane.

Using Method III, dimethylacetamide, t-butyl methyl ether, and hexafluoropropan-2-ol did not provide Form A.

Method IV

The crystalline Compound A Form B (see Example 2) was used in this method. 15 mg of the crystalline material was used with 30 volumes (450 μL) solvent with the exception of DMSO and DMA where 5 volumes was used. Slurries were sonicated for 5 seconds. The slurries were stirred at 500 rpm, cycling between 25° C. and 50° C. (4 h at each temperature) for six days. Any resulting solutions were then left to evaporate quickly at room temperature. The solids were analyzed by XRPD.

Each of the following solvents used in the above described Method IV provided Form A: benzonitrile, sulfolane, formamide, tetraline, acetophenone, benzyl alcohol, ethylene glycol, 1,2-dichlorobenzene, chlorobenzene, cyclohexanone, butyronitrile, acetic acid, t-butyl methyl ether, nitromethane, propionitrile, dimethoxyethane, 1,2-dichloroethane, hexafluorobenzene, t-butanol, hexane, perfluorohexane, and hexafluoropropan-2-ol.

Method V

The crystalline Compound A Form A (see Example 1, Method VIII) was used in this method. 20 mg of the crystalline material was dissolved in THF (410 µL) before the addition of 10 volumes (200 µL) of solvent with the exception of DMSO and DMA where 5 volumes was used. The slurries were stirred at 500 rpm cycling between 25° C. and 50° C. (4 h at each temperature) for 48 hours. Any solutions which were obtained after the heat/cool cycles were allowed to evaporate at room temperature. The solids obtained were analyzed by XRPD.

Each of the following solvents used in the above described Method V provided Form A. Benzonitrile, sulfolane, formamide, tetraline, acetophenone, benzyl alcohol, ethylene glycol, DMSO, 1,2-dichlorobenzene, chlorobenzene, cyclohexanone, butyronitrile, acetic acid, t-butyl methyl ether, propionitrile, dimethoxyethane, 1,2-dichloroethane, hexafluorobenzene, t-butanol, and hexane.

Using Method V, nitromethane, hexafluoropropan-2-ol, and perfluorohexane did not provide Form A.

Method VI

The crystalline Compound A Form A (30 mg, see Example 1, Method VIII) was dissolved in 10 mL of acetone. This solution was subject to fast solvent evaporation on a rota-evaporator (40° C., 35-50 Torr). 12.85 mg of the resulting material was used with 10 volumes (128.5 µL) of solvent with the exception of DMSO and DMA where 5 volumes was used. Slurries were sonicated for 5 seconds. The slurries were stirred at 500 rpm between 25° C. and 50° C. (8 h cycles) for a period of six days. Any resulting solutions were then allowed to evaporate at room temperature. Solids obtained were analyzed by XRPD.

Each of the following solvents used in the above described Method VI provided Form A: benzonitrile, sulfolane, formamide, tetraline, acetophenone, benzyl alcohol, ethylene glycol, DMSO, 1,2-dichlorobenzene, chlorobenzene, butyronitrile, acetic acid, t-butyl methyl ether, nitromethane, propionitrile, dimethoxyethane, 1,2-dichloroethane, hexafluorobenzene, t-butanol, and hexane.

Using Method VI, cyclohexanone, hexafluoropropan-2-ol, and perfluorohexane did not provide Form A.

Method VII

The crystalline Compound A Form A (see Example 1, Method VIII) was used in this method. 30 mg was suspended in 7 volumes of solvent (10% aqueous). Slurries were sonicated for 5 seconds. The slurries were stirred at 500 rpm cycling between 25° C. and 50° C. (8 h cycles) for a period of four days. The solids obtained were analyzed by XRPD.

Each of the following solvents used in the above described Method VII provided Form A: acetone, acetonitrile, ethanol, methanol, 2-methyl-THF, and IPA.

Method VIII

An aqueous solution of sodium hydroxide was added slowly to a stirred suspension of Compound A in water at temperature range (10° C. to 90° C.). A solution of acetic acid in water was then slowly charged at temperature range (10° C. to 90° C.) and the mixture was stirred. The solid was filtered, washed with water, and dried under vacuum to constant weight. Compound A Form A was obtained as white to light yellow crystalline solid.

Data

Figure 1:
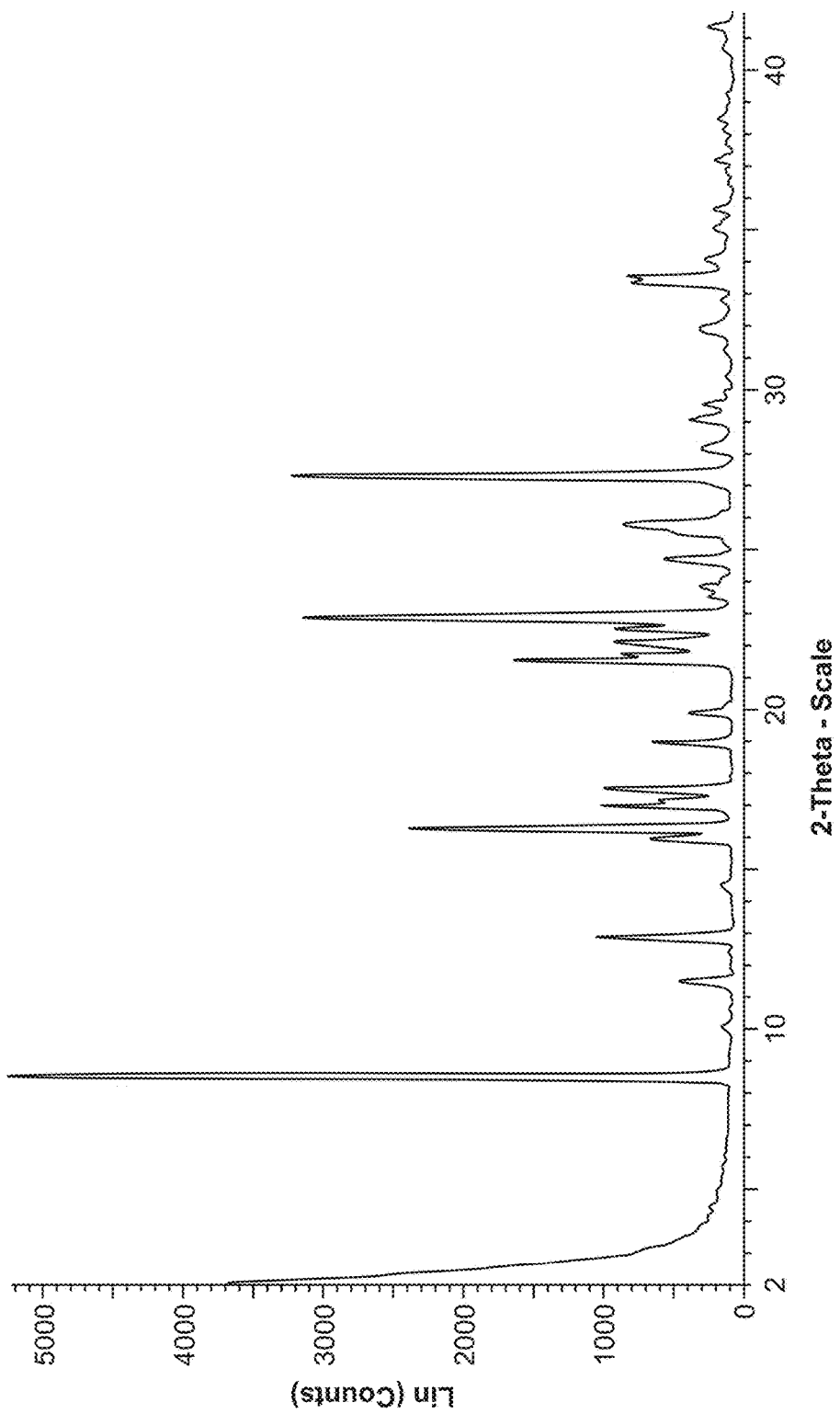
FIG. 1 is an X-ray powder diffraction pattern of Compound A Form A.

The XRPD pattern for Compound A Form A is shown in FIG. 1 and peaks and their related intensities in the XRPD pattern are shown in Table 1 below.

TABLE 1

Peaks in the XRPD Pattern for Compound A Form A

| Peak Position (°2θ) | Relative Intensity (%) |
| --- | --- |
| 8.5 | 100 |
| 10.1 | 3.5 |
| 11.4 | 9.2 |
| 12.8 | 20.6 |
| 14.5 | 3.2 |
| 15.9 | 13.4 |
| 16.2 | 45.5 |
| 16.9 | 18.5 |
| 17.1 | 11.5 |
| 17.5 | 19.0 |
| 19.0 | 12.5 |
| 19.9 | 7.7 |
| 20.2 | 2.8 |
| 21.6 | 31.9 |
| 21.8 | 16.0 |
| 22.0 | 11.9 |
| 22.2 | 17.2 |
| 22.6 | 17.4 |
| 22.9 | 36.4 |
| 23.6 | 4.7 |
| 23.8 | 6.5 |
| 24.1 | 3.4 |
| 24.7 | 11.0 |
| 25.2 | 3.0 |
| 25.6 | 9.8 |
| 25.8 | 16.5 |
| 27.4 | 60.6 |
| 28.2 | 7.7 |
| 28.4 | 3.7 |
| 29.1 | 7.6 |
| 29.2 | 5.8 |
| 29.6 | 5.3 |
| 30.0 | 2.7 |
| 30.4 | 2.3 |
| 31.3 | 2.8 |
| 31.9 | 5.9 |
| 32.0 | 6.1 |
| 32.8 | 3.0 |
| 33.4 | 15.6 |
| 33.6 | 16.1 |
| 34.1 | 5.2 |
| 34.6 | 2.8 |
| 35.1 | 4.3 |
| 35.2 | 4.2 |
| 35.3 | 3.2 |
| 35.7 | 4.0 |
| 36.5 | 2.2 |
| 36.6 | 2.2 |
| 36.9 | 2.4 |
| 37.0 | 2.4 |
| 37.3 | 4.0 |
| 37.4 | 2.8 |

TABLE 1-continued

Peaks in the XRPD Pattern for Compound A Form A

| Peak Position (°2θ) | Relative Intensity (%) |
|---|---|
| 37.7 | 2.3 |
| 37.8 | 2.3 |
| 38.2 | 2.9 |
| 38.5 | 3.2 |
| 38.9 | 2.4 |
| 39.3 | 2.4 |
| 40.8 | 2.8 |
| 41.5 | 4.9 |

Figure 24:
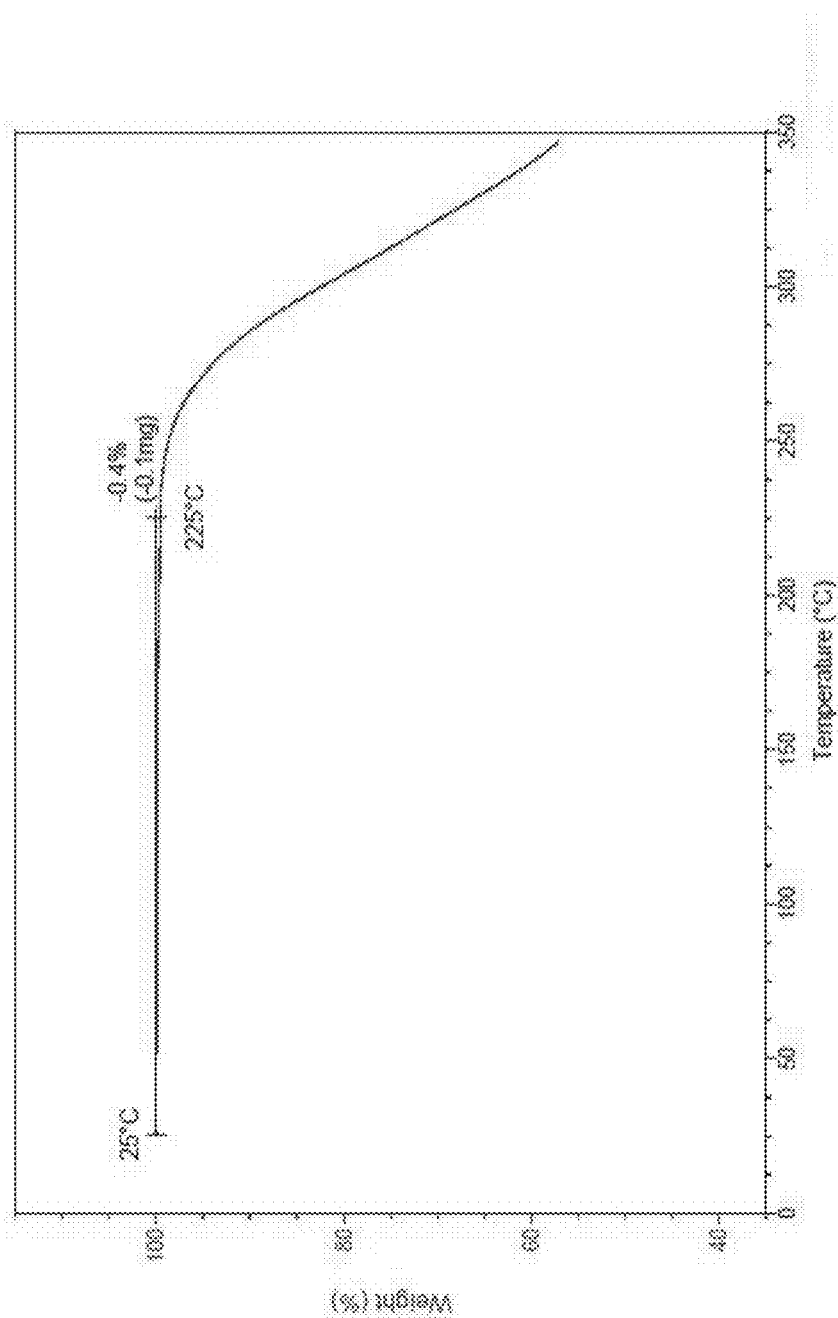
FIG. 24 is the thermogravimetric analysis (TGA) of Compound A Form A.

The results of the differential scanning calorimetry and thermogravimetric analyses of Compound A Form A are presented in FIGS. 2 and 24, respectively. The thermogravimetric analysis shows negligible weight loss of approximately 0.4% between 25° C. and 225° C. followed by a steady loss of weight above 225° C., suggesting sublimation or decomposition of the material at these temperatures (FIG. 24). The differential scanning calorimetry analysis of Compound A Form A showed a very shallow exotherm in the range from about 80-190° C., followed by a sharp endotherm at about 224.3° C. (peak maximum). The sharp endotherm corresponded to the melt of the material, as determined by hotstage microscopy.

The hotstage microscopy of Compound A Form A showed little change of the material below its melting point. Some changes in birefringence were noted in the range of about 150-200° C. The sample melted within the temperature range of about 218.5-222.4° C.

The moisture sorption data for Compound A Form A showed negligible weight gain, approximately 0.2% gained from between 5% to 95% relative humidity, which was lost on desorption. The small moisture uptake of Compound A Form A is indicative of a kinetically non-hygroscopic material.

Example 2

Preparation of Compound A Form B

Method

Crystalline Compound A Form B was provided by lyophilization of Form A in a 1,4-dioxane:water (2:1) mixture. 20 mg of the crystalline Compound A Form B was dissolved in 20 volumes 1,4-dioxane before addition of 20 volumes cosolvent. The solvent systems were left to evaporate at room temperature, under the fume hood. The solids obtained from this experiment were analysed by XRPD.

Each of the following cosolvents used in the above described method provided Form B, 1,4-Dioxane:water (1:1), 1,4-dioxane:water (1:1), 1,4-dioxane:methanol (1:1), 1,4-dioxane:ethanol, 1,4-dioxane:acetone (1:1), 1,4-dioxane:THF (1:1), and 1,4-dioxane:heptane (1:1).

Data

Figure 3:
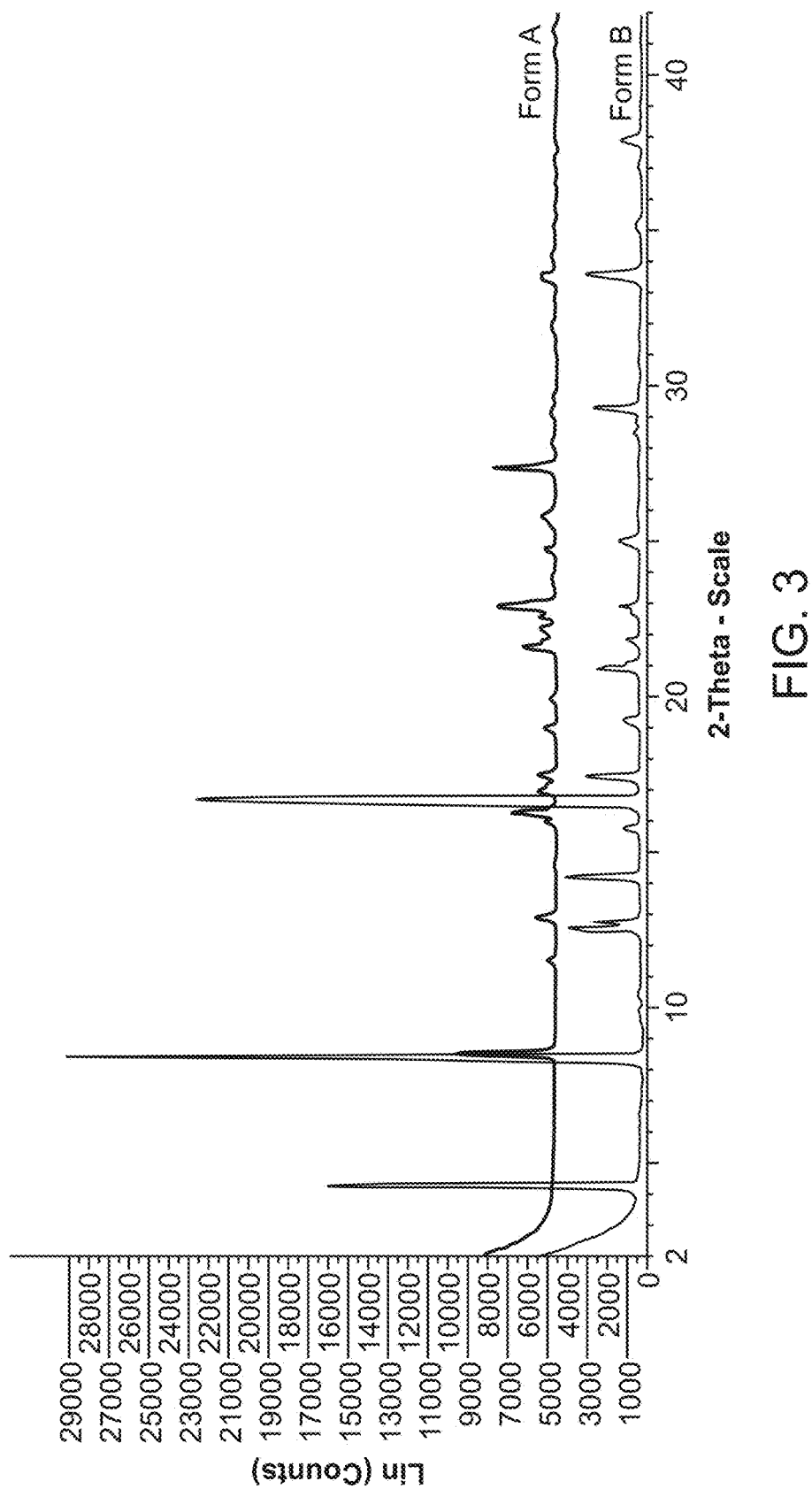
FIG. 3 is an X-ray powder diffraction pattern of Compound A Form B (bottom) plotted with an X-ray powder diffraction pattern of Compound A Form A (top).

The XRPD pattern for Compound A Form B is shown in FIG. 3 and peaks and their related intensities in the XRPD pattern are shown in Table 2 below. The crystalline pattern changed after the sample was stored at 25° C./96% RH for twelve days, reverting to Form A.

TABLE 2

Peaks in the XRPD Pattern for Compound A Form B

| Peak Position (°2θ) | Relative Intensity (%) |
|---|---|
| 4.2 | 53.9 |
| 8.3 | 100 |
| 9.8 | 1.3 |
| 10.5 | 1.1 |
| 11.5 | 1.0 |
| 12.5 | 12.9 |
| 12.7 | 8.3 |
| 12.9 | 1.3 |
| 14.1 | 13.7 |
| 15.8 | 3.9 |
| 16.6 | 76.3 |
| 17.4 | 10.4 |
| 19.2 | 3.7 |
| 20.9 | 8.2 |
| 21.0 | 3.7 |
| 21.8 | 3.7 |
| 22.7 | 3.0 |
| 22.9 | 4.6 |
| 24.9 | 2.7 |
| 25.0 | 4.9 |
| 25.9 | 1.5 |
| 27.5 | 1.5 |
| 28.4 | 2.1 |
| 28.8 | 1.7 |
| 29.3 | 9.0 |
| 30.0 | 1.3 |
| 30.8 | 1.4 |
| 31.6 | 1.2 |
| 33.5 | 6.9 |
| 33.6 | 9.9 |
| 35.2 | 1.5 |
| 37.0 | 1.2 |
| 37.9 | 4.3 |
| 41.6 | 0.8 |

No residual solvent was observed, other than water. A weight loss of 2.8% w/w between room temperature and 90° C. in the TGA thermogram suggested the presence of 0.5 equivalent of water (theoretical 2.5% w/w) (FIG. 4). The DSC thermogram showed an endothermic event associated to the weight loss (FIG. 4). A sharp endothermic event occurs at 222.3° C. (−127.8 J/g), which matches the melt of Form A.

High resolution XRPD data was collected over a month. After a full month at ambient temperature (32 days), the sample (Form B) almost completely reverted to anhydrous Form A.

Example 3

Preparation of Compound A Form C

Method

Crystalline [(4-hydroxy-1-methyl-7-phenoxy-isoquinoline-3-carbonyl)-amino]-acetic acid hexafluoropropan-2-ol solvate (Compound A Form C) was prepared following the procedure described in Methods I, II, III and VI of Example 1 using hexafluoropropan-2-ol as the solvent.

Data

Figure 5:
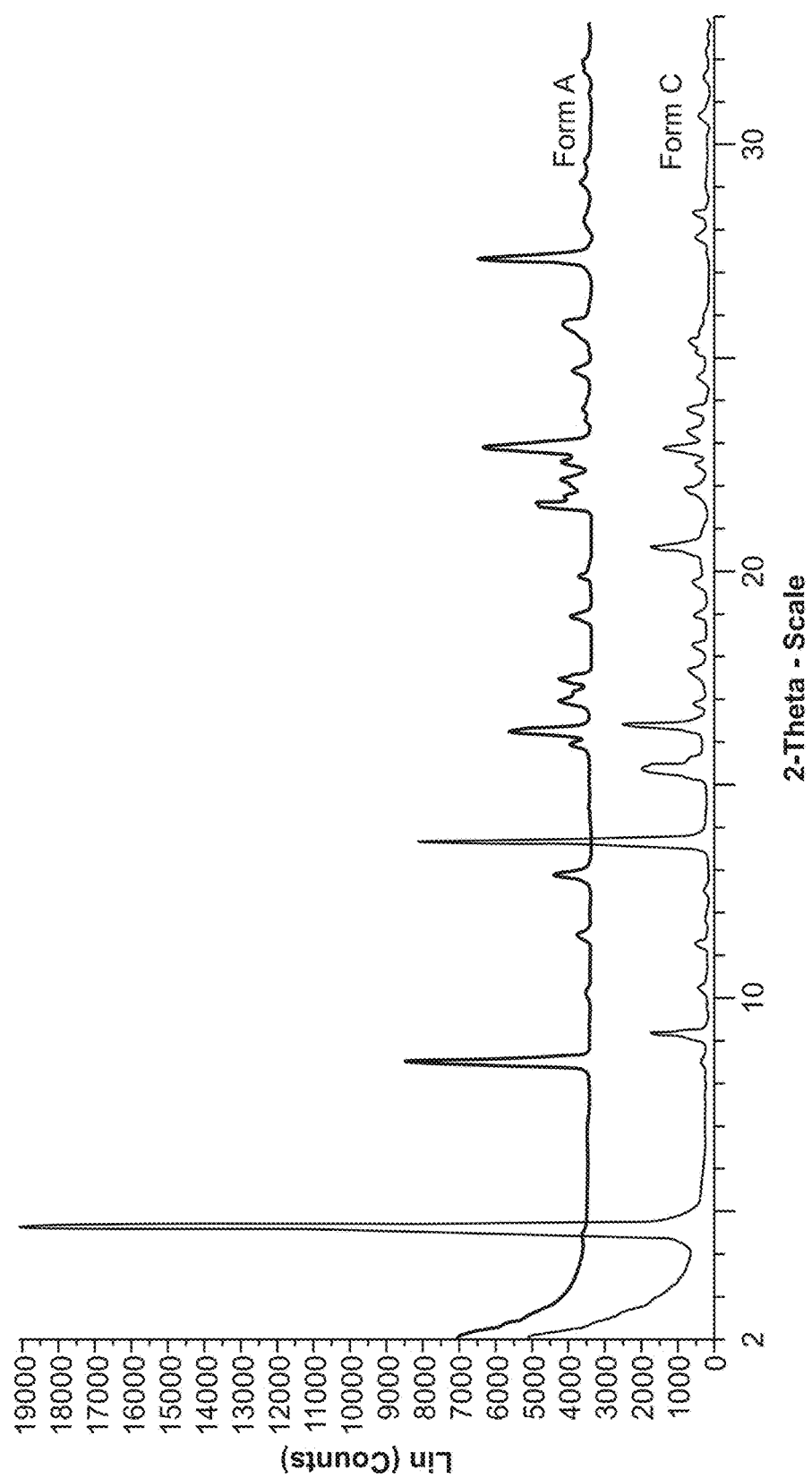
FIG. 5 is an X-ray powder diffraction pattern of Compound A Form C (bottom) plotted with an X-ray powder diffraction pattern of Compound A Form A (top).

The XRPD pattern for Compound A Form C is shown in FIG. 5 and peaks and their related intensities in the XRPD pattern are shown in Table 3 below.

TABLE 3

Peaks in the XRPD Pattern for Compound A Form C

| Peak Position (°2θ) | Relative Intensity (%) |
|---|---|
| 4.5 | 100 |
| 8.5 | 1.6 |
| 9.1 | 7.9 |
| 10.2 | 1.9 |
| 11.2 | 2.5 |
| 11.8 | 1.2 |
| 12.5 | 1.2 |
| 13.7 | 37 |
| 15.4 | 9.2 |
| 15.5 | 8.3 |
| 15.6 | 3 |
| 16.4 | 11.5 |
| 16.9 | 2.5 |
| 17.7 | 3.3 |
| 18.3 | 2.7 |
| 18.7 | 1.2 |
| 19.0 | 2.3 |
| 19.8 | 2.5 |
| 20.6 | 8 |
| 21.9 | 3.5 |
| 22.4 | 1.5 |
| 22.5 | 2.3 |
| 22.9 | 6.3 |
| 23.3 | 3.1 |
| 23.8 | 3.4 |
| 24.6 | 2 |
| 25.2 | 2.3 |
| 25.4 | 3.1 |
| 25.7 | 1.9 |
| 26.0 | 1.5 |
| 27.5 | 1.2 |
| 27.9 | 2.3 |
| 28.4 | 2.6 |
| 29.1 | 1.4 |
| 29.4 | 1 |
| 29.8 | 1 |
| 30.2 | 1 |
| 30.8 | 2.1 |
| 31.6 | 1.2 |
| 31.7 | 1.5 |
| 32.2 | 1.3 |
| 32.3 | 1.1 |
| 33.1 | 0.9 |
| 34.1 | 1.4 |
| 34.2 | 1.5 |
| 35.1 | 0.9 |
| 35.5 | 0.8 |
| 37.0 | 0.9 |
| 37.8 | 1.1 |
| 38.7 | 1 |
| 40.2 | 0.7 |
| 40.9 | 1.1 |
| 41.8 | 1.2 |

Residual solvent was observed by proton NMR and was assigned to the hexafluoropropan-2-ol. Thermal analysis was also carried out on this sample (FIG. 6). A weight loss of 7.8% w/w between room temperature and 130° C. in the TGA thermogram suggested the presence of ⅙ equivalent of hexafluoropropan-2-ol (theoretical 7.36% w/w) in the sample. The DSC thermogram showed an endothermic event associated to the weight loss followed by a small exothermic event (ca. 130° C.) (FIG. 6). A sharp endothermic event occurs at 222.2° C. (−17.9 J/g), which matches the melt of Form A. In conclusion, the material isolated from hexafluoropropan-2-ol is a meta-stable solvate under ambient conditions and converts to Form A.

Example 4

Preparation of Compound A Form D

Method

Crystalline [(4-hydroxy-1-methyl-7-phenoxy-isoquinoline-3-carbonyl)-amino]-acetic acid DMSO:water solvate (Compound A Form D) was prepared from slow evaporation from THF/DMSO (20 volumes THF/5 volumes DMSO) of either mostly amorphous Compound A or Form A.

Data

The XRPD pattern for Compound A Form D is shown in FIG. 8 and peaks and their related intensities in the XRPD pattern are shown in Table 4 below. The sample (Form D) converted to Form A when left drying at ambient temperature.

TABLE 4

Peaks in the XRPD Pattern for Compound A Form D

| Peak Position (°2θ) | Relative Intensity (%) |
|---|---|
| 4.2 | 32.7 |
| 4.3 | 29.4 |
| 8.4 | 65 |
| 8.5 | 65 |
| 12.6 | 30.9 |
| 15.8 | 20.6 |
| 16.8 | 100 |
| 18.9 | 5.5 |
| 19.3 | 19.1 |
| 20.7 | 6.2 |
| 21.7 | 3.8 |
| 22.1 | 23 |
| 22.6 | 4.6 |
| 23.1 | 11.7 |
| 24.0 | 8.7 |
| 24.5 | 3.1 |
| 25.3 | 12.1 |
| 25.4 | 10.3 |
| 26.8 | 4 |
| 27.1 | 4.4 |
| 27.3 | 3.9 |
| 28.4 | 43 |
| 31.2 | 7.7 |
| 32.0 | 3.4 |
| 33.3 | 4.4 |
| 33.4 | 3 |
| 34.0 | 6.2 |
| 35.8 | 3.7 |
| 38.3 | 7.6 |
| 39.1 | 3.6 |
| 40.9 | 2.5 |
| 41.6 | 3.6 |

Residual solvent was observed by proton NMR and was assigned to the DMSO. The TGA thermogram and DSC thermogram are shown in FIG. 8. The TGA shows a first weight loss between 40-150° C. of 18.5% (combination of water and DMSO) and a second weight loss between 170-220° C. (possible DMSO). Two broad endotherms at 37.6° C. and 90.4° C. were possible due to loss of water and DMSO. A small endotherm at 222.0° C. was observed due to melt of Form A.

Example 5

Preparation of Salts of Compound A

Method

The crystalline Compound A Form A was used to prepare the following salts.

Compound A Form A (50 mg per experiment) was dissolved in acetone or THF (50 vol, 2.1 ml) at 50° C. The solutions were treated with 1.1 mol eq. of the corresponding counter ion (for example, 1.0 M aqueous solution of sodium hydroxide, potassium hydroxide or hydrochloric acid). The temperature was maintained at 50° C. for 20 min then cooled to 0° C. at 0.1° C./min with stirring. After 20 h at 0° C., the solids were filtered, air dried for 10 min and analyzed by the appropriate techniques.

Data

Compound A Sodium Salt

Figure 9:
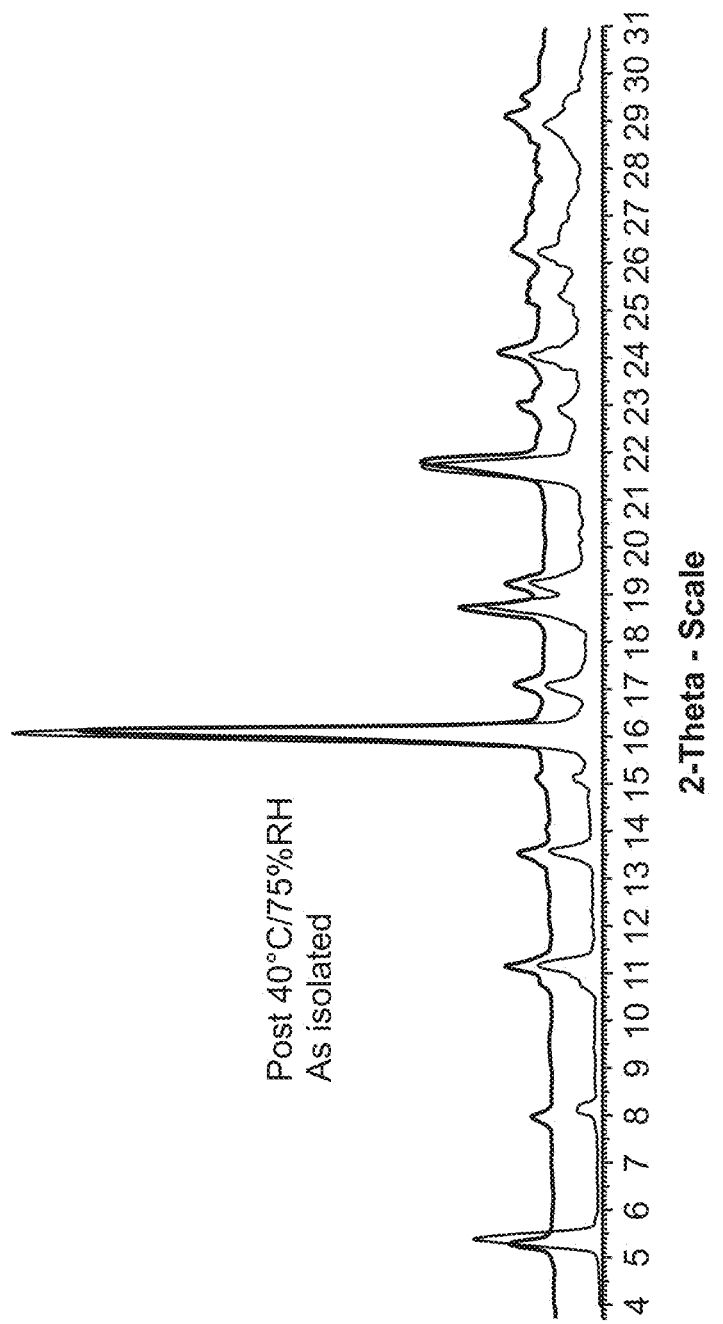
FIG. 9 is an X-ray powder diffraction pattern of Compound A sodium salt as isolated (bottom) and at 40° C./75% RH (top).

The XRPD pattern for Compound A sodium salt is shown in FIG. 9 and peaks and their related intensities in the XRPD pattern are shown in Table 5 below.

TABLE 5

Peaks in the XRPD Pattern for Compound A Sodium Salt

| Peak Position (°2θ) | Relative Intensity (%) |
|---|---|
| 5.3 | 22.0 |
| 8.1 | 4.4 |
| 11.1 | 10.9 |
| 13.5 | 9.3 |
| 15.1 | 5.2 |
| 16.0 | 100.0 |
| 17.0 | 9.6 |
| 18.7 | 20.0 |
| 19.2 | 13.3 |
| 21.6 | 30.7 |
| 22.9 | 7.7 |
| 24.0 | 12.6 |
| 25.3 | 7.5 |
| 26.2 | 11.0 |
| 28.9 | 10.1 |

The stoichiometry (ionic Compound A:counter ion) was determined to be 1:1 by Ion Chromatography (Metrohm 761 Compact IC, IC Net software v2.3). The TGA thermogram and DSC thermogram are shown in FIG. 10. The TGA thermogram shows a weight loss between 40-90° C. of 11.5%. The DSC thermogram shows a broad endotherm at 64.1° C., followed by two exotherms at 150.5° C. and 190.3° C. and a sharp melt at 313.6° C. Purity was determined to be about 99.6%.

Compound A Potassium Salt

Figure 21:
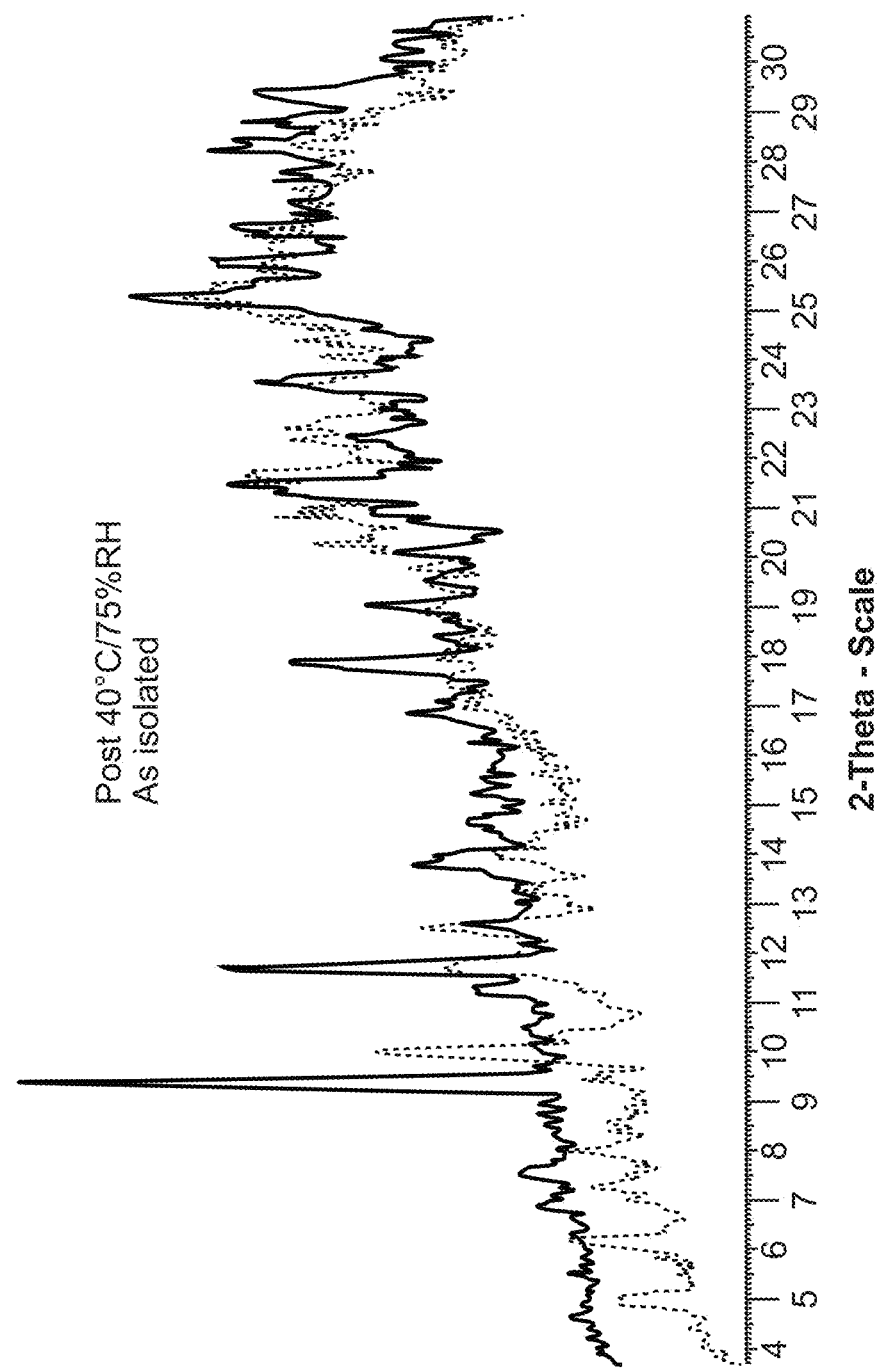
FIG. 21 is an X-ray powder diffraction pattern of Compound A potassium salt as isolated (bottom) and at 40° C./75% RH (top).

The stoichiometry (ionic Compound A:counter ion) was determined to be 1:1 by Ion Chromatography (Metrohm 761 Compact IC, IC Net software v2.3). The XRPD pattern for the Compound A potassium salt is shown in FIG. 21. As seen in the Figure, the potassium salt is substantially amorphous. Thermal analysis showed a possible loss of water followed by a recrystallization event to produce non-solvated, crystalline form with a melt at 291° C. (FIG. 22).

Compound A L-Arginine Salt

Figure 11:
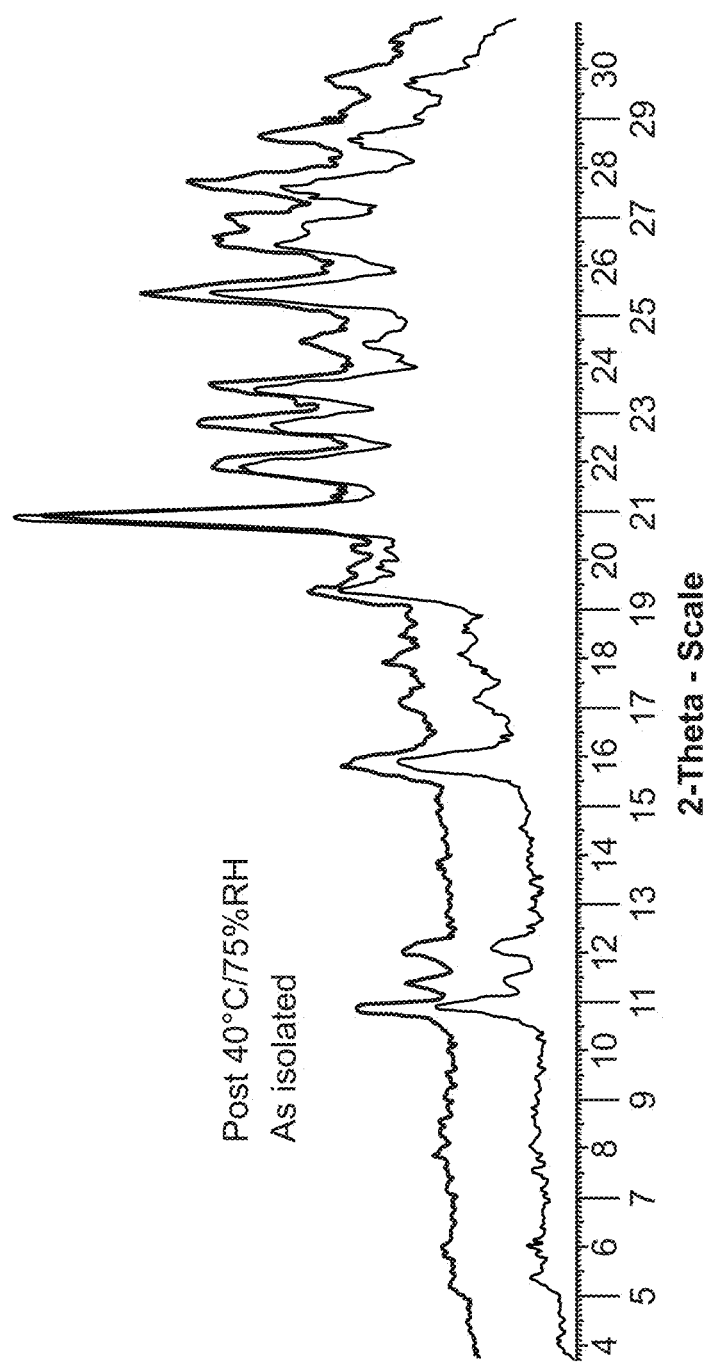
FIG. 11 is an X-ray powder diffraction pattern of Compound A L-arginine salt as isolated (bottom) and at 40° C./75% RH (top).

The XRPD pattern for Compound A L-arginine salt is shown in FIG. 11 and peaks and their related intensities in the XRPD pattern are shown in Table 6 below.

TABLE 6

Peaks in the XRPD Pattern for Compound A L-arginine salt

| Peak Position (°2θ) | Relative Intensity (%) |
|---|---|
| 10.8 | 24.5 |
| 11.4 | 13.1 |
| 12.0 | 15.1 |
| 15.8 | 31.7 |
| 17.1 | 18.2 |
| 18.0 | 20.9 |
| 19.4 | 41.9 |
| 20.8 | 100.0 |
| 21.8 | 59.7 |
| 22.7 | 53.7 |
| 23.4 | 56.8 |
| 24.4 | 37.5 |
| 25.4 | 64.4 |
| 26.4 | 53.7 |
| 26.8 | 48.8 |
| 27.5 | 52.3 |
| 28.5 | 40.4 |
| 29.7 | 30.5 |

The stoichiometry (ionic Compound A:counter ion) was determined to be about 1:1 by NMR. The TGA thermogram and DSC thermogram are shown in FIG. 12. The TGA thermogram shows a weight loss between 40-100° C. of 4.5%. The DSC thermogram shows two broad endotherms at 79.6° C. and 143.3° C., an exotherm at 172.5° C., followed by an endotherm at 210.1° C. Purity was determined to be about 99.5%.

Compound A L-Lysine Salt

Figure 13:
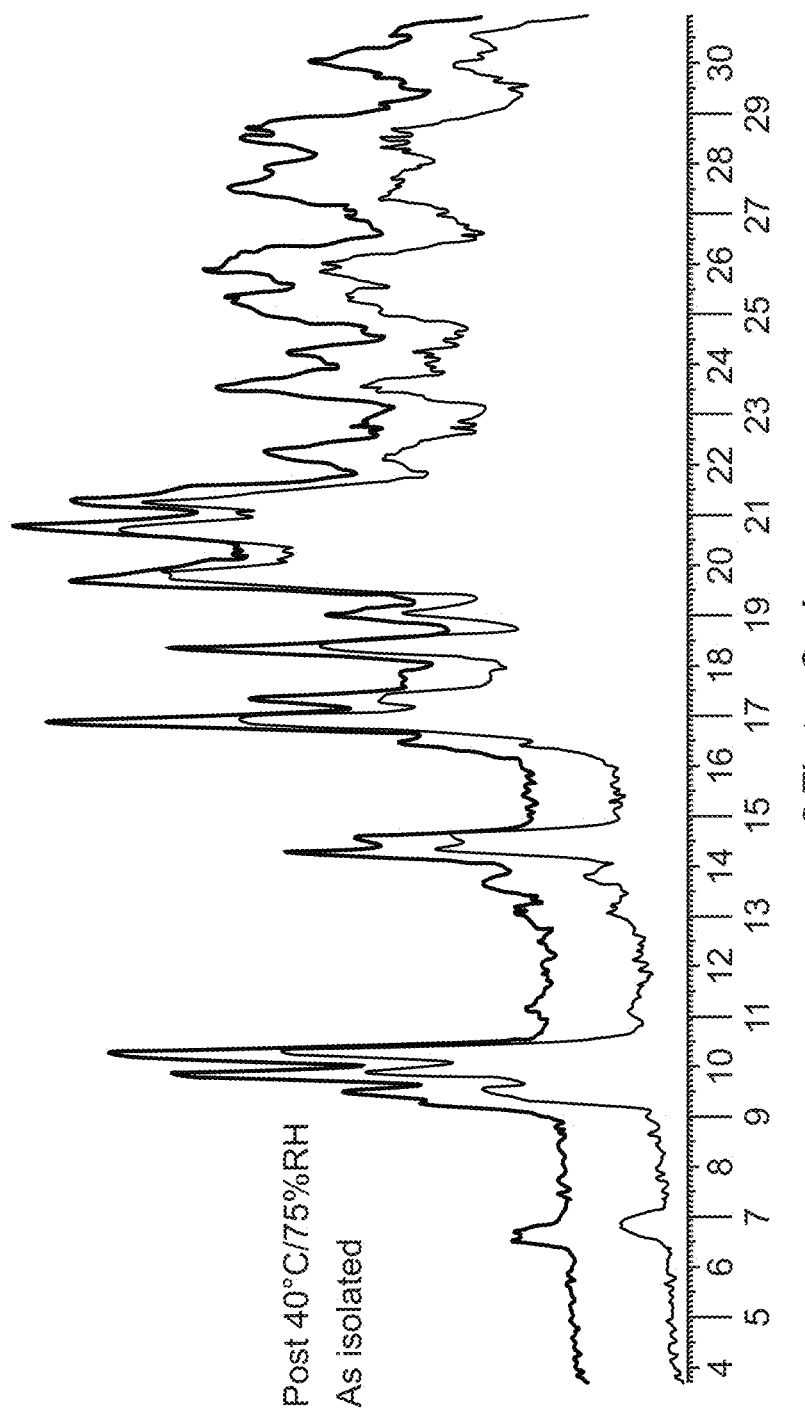
FIG. 13 is an X-ray powder diffraction pattern of Compound A L-lysine salt as isolated (bottom) and at 40° C./75% RH (top).

The XRPD pattern for Compound A L-lysine salt is shown in FIG. 13 and peaks and their related intensities in the XRPD pattern are shown in Table 7 below.

TABLE 7

Peaks in the XRPD Pattern for Compound A L-lysine salt

| Peak Position (°2θ) | Relative Intensity (%) |
|---|---|
| 6.8 | 11.5 |
| 9.5 | 36.4 |
| 9.9 | 57.4 |
| 10.2 | 71.5 |
| 13.1 | 13.9 |
| 13.8 | 18.4 |
| 14.4 | 44.8 |
| 14.6 | 41.6 |
| 16.9 | 78.8 |
| 17.3 | 55.4 |
| 18.4 | 65.1 |
| 19.0 | 50.1 |
| 19.8 | 92.4 |
| 20.7 | 100.0 |
| 21.2 | 95.1 |
| 22.1 | 53.7 |
| 23.6 | 58.0 |
| 25.5 | 59.8 |
| 25.0 | 64.7 |
| 26.1 | 63.9 |
| 27.4 | 54.3 |
| 28.4 | 53.4 |
| 28.6 | 53.8 |
| 28.8 | 52.3 |
| 30.0 | 41.7 |
| 30.6 | 38.2 |

The stoichiometry (ionic Compound A counter ion) was determined to be about 1:1 by NMR. The TGA thermogram and DSC thermogram are shown in FIG. 14. The TGA thermogram shows a weight loss between 235-270° C. of 12.1%. The DSC thermogram shows a sharp melt at 230.7° C. and a broad endotherm at 237.1° C. Purity was determined to be about 99.6%.

Compound A Ethanolamine Salt

Figure 15:
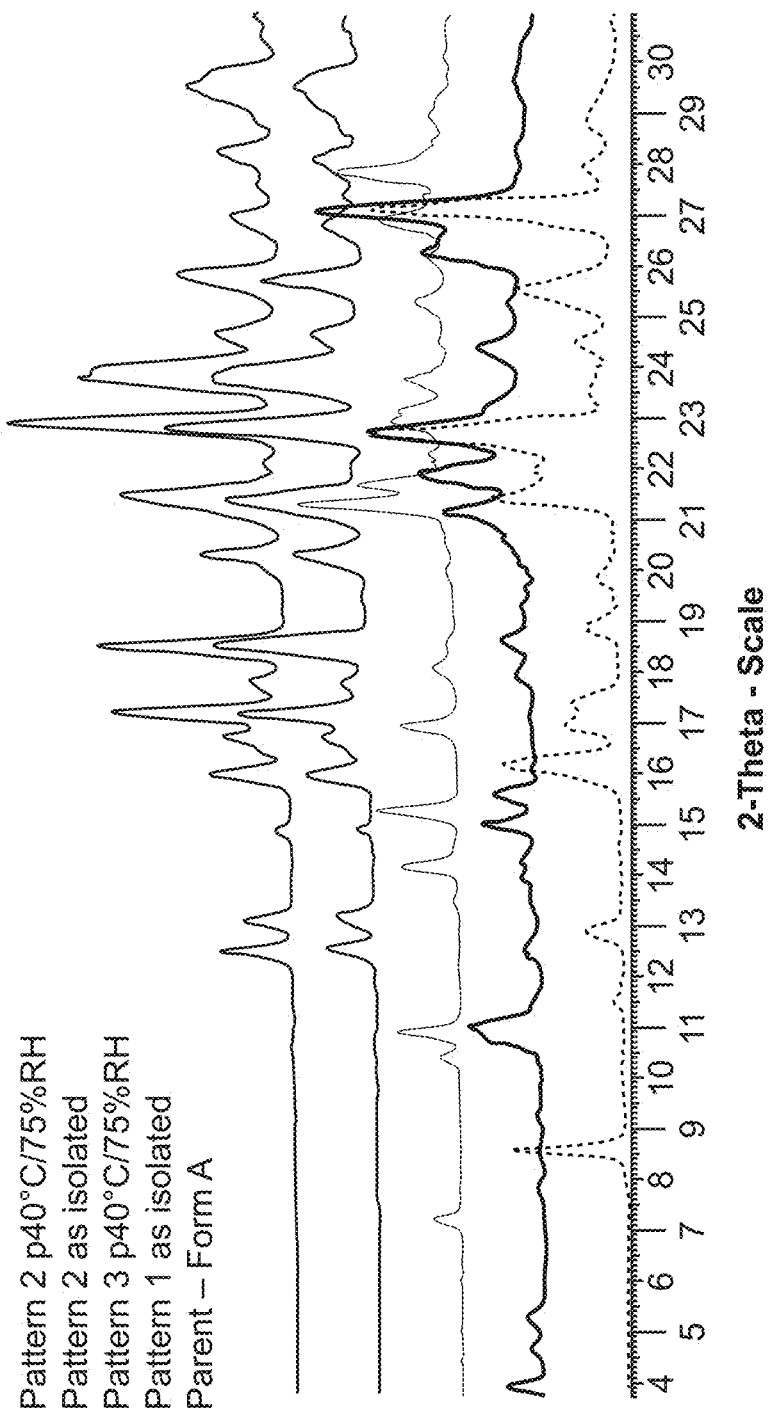
FIG. 15 is an X-ray powder diffraction pattern of Compound A Form A (bottom), Compound A ethanolamine salt pattern 1 as isolated (second to bottom), Compound A ethanolamine salt pattern 3 at 40° C./75% RH (middle), Compound A ethanolamine salt pattern 2 as isolated (second to top), and Compound A ethanolamine salt pattern 2 at 40° C./75% RH (top).

The XRPD patterns for Compound A ethanolamine salt is shown in FIG. 15 and peaks and their related intensities in the XRPD patterns are shown in Tables 8, 9 and 10 below. Pattern 1 was observed from acetone, pattern 2 was observed from THF, and Pattern 3 was observed at 40° C./75% RH.

TABLE 8

Peaks in the XRPD Pattern for Compound A ethanolamine salt (Pattern 1)

| Peak Position (°2θ) | Relative Intensity (%) |
|---|---|
| 3.8 | 15.6 |
| 4.6 | 6.3 |
| 5.1 | 8.3 |
| 7.7 | 4.8 |
| 10.9 | 32.8 |
| 12.5 | 10.0 |
| 15.0 | 28.2 |
| 15.5 | 23.5 |
| 17.9 | 14.0 |
| 18.6 | 20.1 |
| 21.1 | 45.2 |
| 21.8 | 54.9 |
| 22.7 | 77.7 |
| 24.4 | 30.3 |
| 26.2 | 53.6 |
| 26.6 | 47.6 |
| 27.1 | 100.0 |

TABLE 9

Peaks in the XRPD Pattern for Compound A ethanolamine salt (Pattern 2)

| Peak Position (°2θ) | Relative Intensity (%) |
|---|---|
| 12.5 | 25.5 |
| 13.1 | 22.4 |
| 14.9 | 12.8 |
| 15.9 | 37.4 |
| 16.7 | 29.3 |
| 17.1 | 68 0 |
| 17.8 | 19.4 |
| 18.5 | 79.6 |
| 20.2 | 42.4 |
| 21.4 | 73.3 |
| 22.8 | 100.0 |
| 23.8 | 80.2 |
| 24.7 | 34.6 |
| 25.7 | 57.9 |
| 26.8 | 28.9 |
| 27.4 | 19.0 |
| 28.0 | 32.7 |
| 29.5 | 41.4 |
| 30.8 | 19.6 |

TABLE 10

Peaks in the XRPD Pattern for Compound A ethanolamine salt (Pattern 3)

| Peak Position (°2θ) | Relative Intensity (%) |
|---|---|
| 7.2 | 18.1 |
| 10.3 | 15.2 |
| 10.8 | 39.7 |
| 13.4 | 8.1 |
| 14.1 | 37.3 |
| 16.2 | 52.9 |
| 16.9 | 37.5 |
| 18.1 | 17.7 |
| 21.3 | 100.0 |
| 21.7 | 64.8 |
| 22.3 | 21.7 |
| 22.9 | 42.3 |
| 23.1 | 39.6 |
| 23.7 | 36.1 |
| 25.3 | 29.9 |
| 26.2 | 23.3 |
| 26.9 | 50.5 |
| 27.8 | 75.0 |
| 29.0 | 22.7 |
| 18.5 | 11.8 |

For both THF and acetone, the stoichiometry (ionic Compound A:counter ion) was determined to be about 1:1 by NMR. The TGA thermogram and DSC thermogram for the Compound A ethanolamine salt from acetone is shown in FIG. 16. The TGA thermogram shows a weight loss between 155-250° C. of 10.1% (0.8 equivalents of ethanolamine). The DSC thermogram shows a sharp melt at 171.4° C. and a broad endotherm at 186.0° C. Purity was determined to be about 99.0%. For the Compound A ethanolamine salt from THF, the TGA thermogram showed a weight loss between 155-250° C. of 10.1% (0.8 equivalents of ethanolamine), and the DSC thermogram showed a sharp melt at 172.4° C. and a broad endotherm at 185.5° C. Purity was determined to be about 99.1%.

Compound A Diethanolamine Salt

Figure 17:
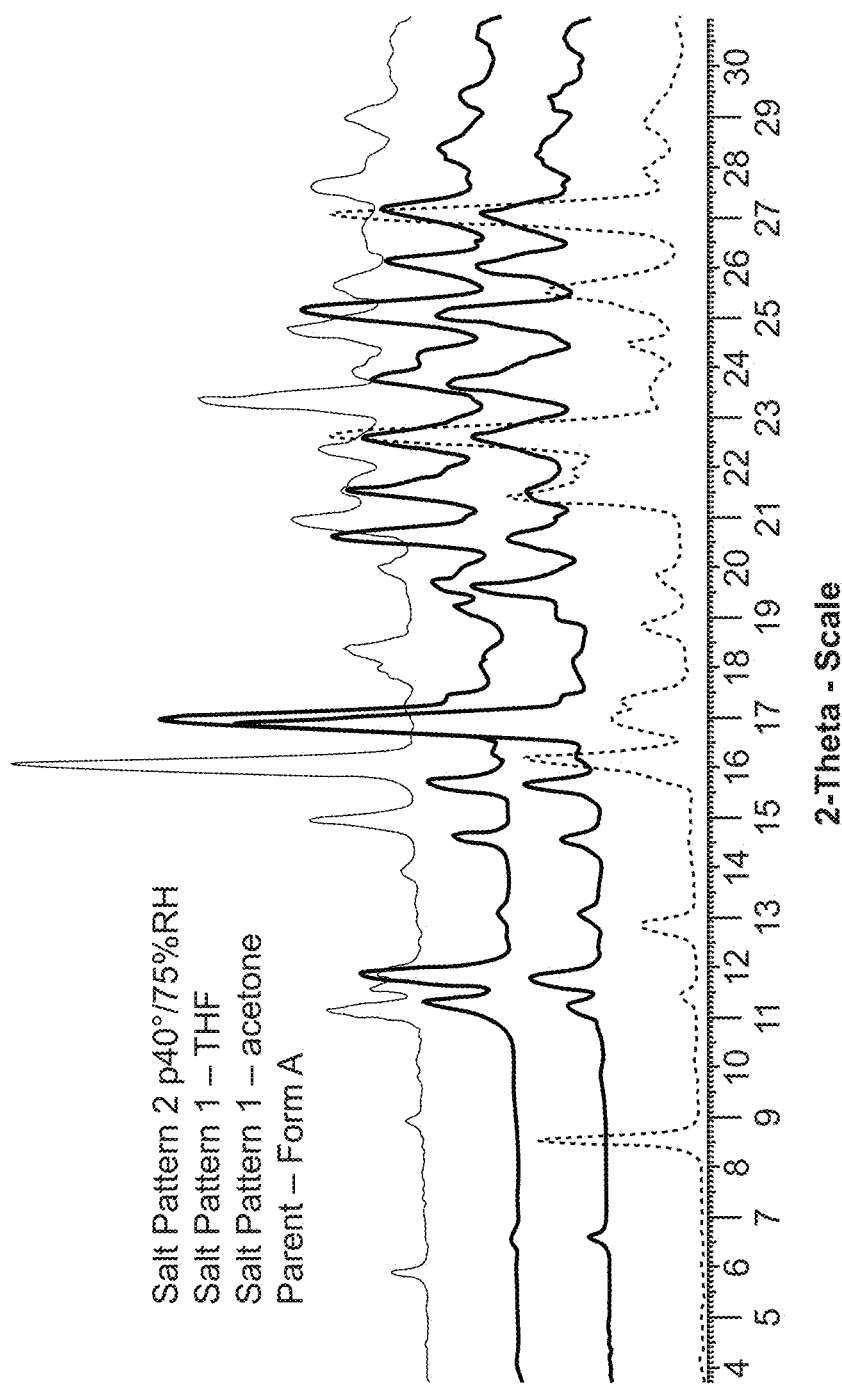
FIG. 17 is an X-ray powder diffraction pattern of Compound A Form A (bottom), Compound A diethanolamine salt pattern 1 from acetone (second to bottom), Compound A diethanolamine salt pattern 1 from THF (second to top), and Compound A diethanolamine salt at 40° C./75% RH (pattern 2, top).

The XRPD patterns for Compound A diethanolamine salt is shown in FIG. 17 and peaks and their related intensities in the XRPD patterns are shown in Tables 11 and 12 below. Pattern 1 was observed from acetone and Pattern 2 was observed at 40° C./75% RH.

TABLE 11

Peaks in the XRPD Pattern for Compound A diethanolamine salt (Pattern 1)

| Peak Position (°2θ) | Relative Intensity (%) |
|---|---|
| 6.6 | 6.6 |
| 11.2 | 12.5 |
| 11.8 | 21.6 |
| 13.0 | 9.5 |
| 14.5 | 13.6 |
| 15.6 | 22.9 |
| 16.9 | 100.0 |
| 19.6 | 37.5 |
| 20.5 | 27.7 |
| 21.4 | 23.1 |
| 22.6 | 37.3 |
| 23.7 | 42.9 |
| 25.0 | 46.9 |
| 26.0 | 36.5 |
| 27.1 | 35.3 |
| 28.3 | 20.8 |
| 29.4 | 17.1 |
| 30.6 | 13.2 |

TABLE 12

Peaks in the XRPD Pattern for Compound
A diethanolamine salt (Pattern 2)

| Peak Position (°2θ) | Relative Intensity (%) |
|---|---|
| 5.9 | 9.4 |
| 8.9 | 5.9 |
| 11.1 | 23.9 |
| 11.5 | 13.9 |
| 11.9 | 12.7 |
| 13.9 | 7.0 |
| 14.9 | 27.7 |
| 16.0 | 100.0 |
| 18.3 | 20.0 |
| 20.0 | 11.9 |
| 20.9 | 32.5 |
| 21.5 | 20.5 |
| 22.3 | 26.4 |
| 23.3 | 54.6 |
| 24.0 | 17.1 |
| 24.8 | 33.5 |
| 25.6 | 22.4 |
| 27.6 | 27.7 |
| 29.0 | 20.1 |

The stoichiometry (ionic Compound A:counter ion) was determined to be about 1:1 by NMR. The TGA thermogram and DSC thermogram are shown in FIG. 18. The TGA thermogram shows a weight loss between 155-250° C. (of 12.6%. The DSC thermogram shows a sharp melt at 150.2° C. and a broad endotherm at 172.2° C. Purity was determined to be about 99.7%.

Compound A Tromethamine Salt

Figure 19:
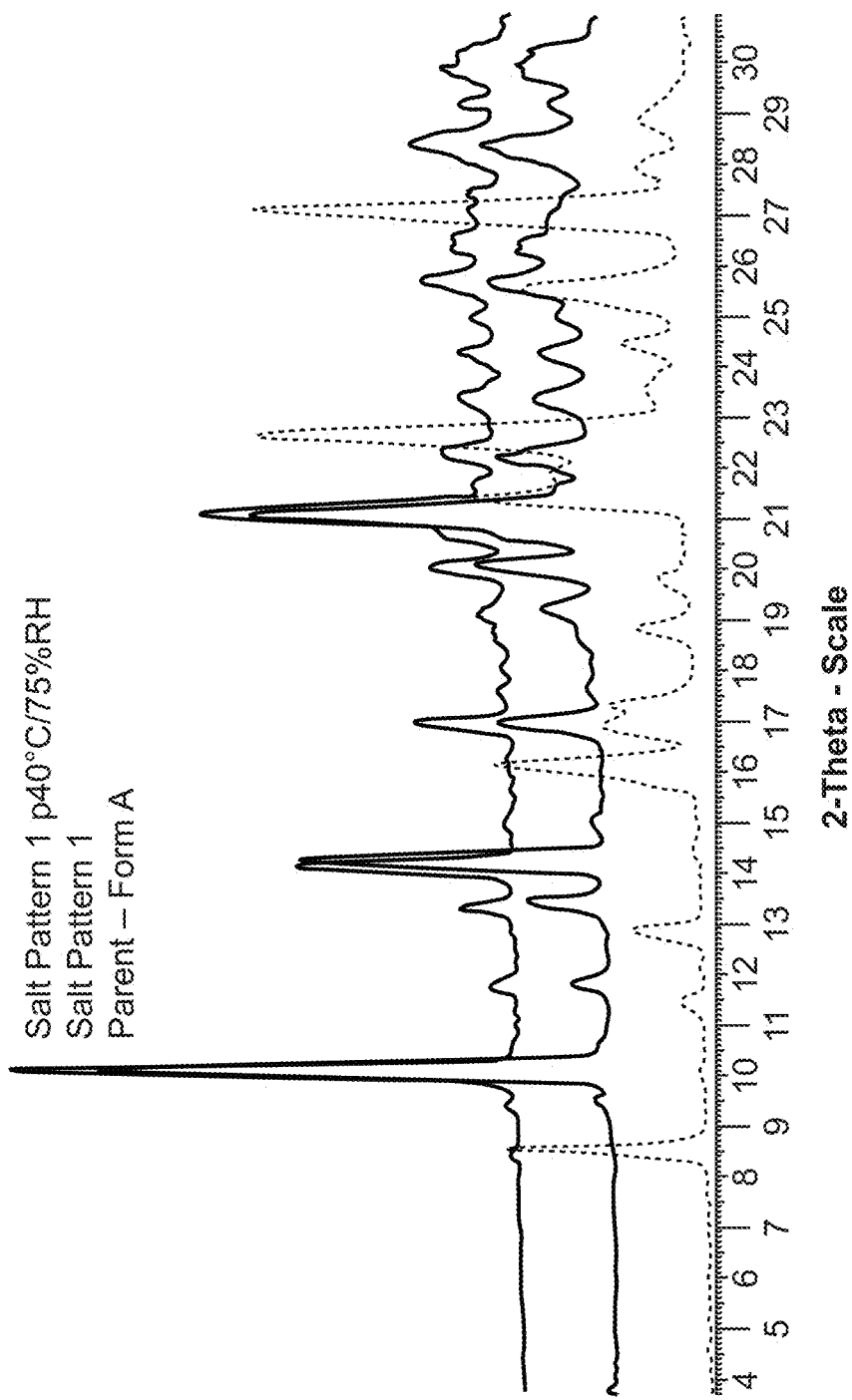
FIG. 19 is an X-ray powder diffraction pattern of Compound A Form A (bottom), and Compound A tromethamine salt as isolated (middle) and at 40° C./75% RH (top).

The XRPD pattern for Compound A tromethamine salt is shown in FIG. 19 and peaks and their related intensities in the XRPD pattern is shown in Table 13 below.

TABLE 13

Peaks in the XRPD Pattern for Compound A tromethamine salt

| Peak Position (°2θ) | Relative Intensity (%) |
|---|---|
| 9.4 | 4.3 |
| 10.1 | 100.0 |
| 11.8 | 8.5 |
| 13.4 | 15.3 |
| 14.2 | 53.0 |
| 15.0 | 5.1 |
| 16.9 | 20.3 |
| 19.2 | 12.9 |
| 20.1 | 23.5 |
| 21.1 | 69.2 |
| 22.3 | 21.4 |
| 23.4 | 14.7 |
| 24.3 | 13.6 |
| 25.1 | 10.5 |
| 25.7 | 21.5 |
| 26.3 | 16.9 |
| 28.4 | 22.9 |
| 29.2 | 12.0 |
| 30.0 | 17.1 |

The stoichiometry (ionic Compound A:counter ion) was determined to be about 1:1 by NMR. The TGA thermogram and DSC thermogram are shown in FIG. 20. The TGA thermogram shows a weight loss between 180-260° C. of 11.0%. The DSC thermogram shows a sharp melt at 176.5° C. and a broad endotherm at 182.6° C. Purity was determined to be about 99.7%.

Compound A Hydrochloric Acid Salt

Figure 25:
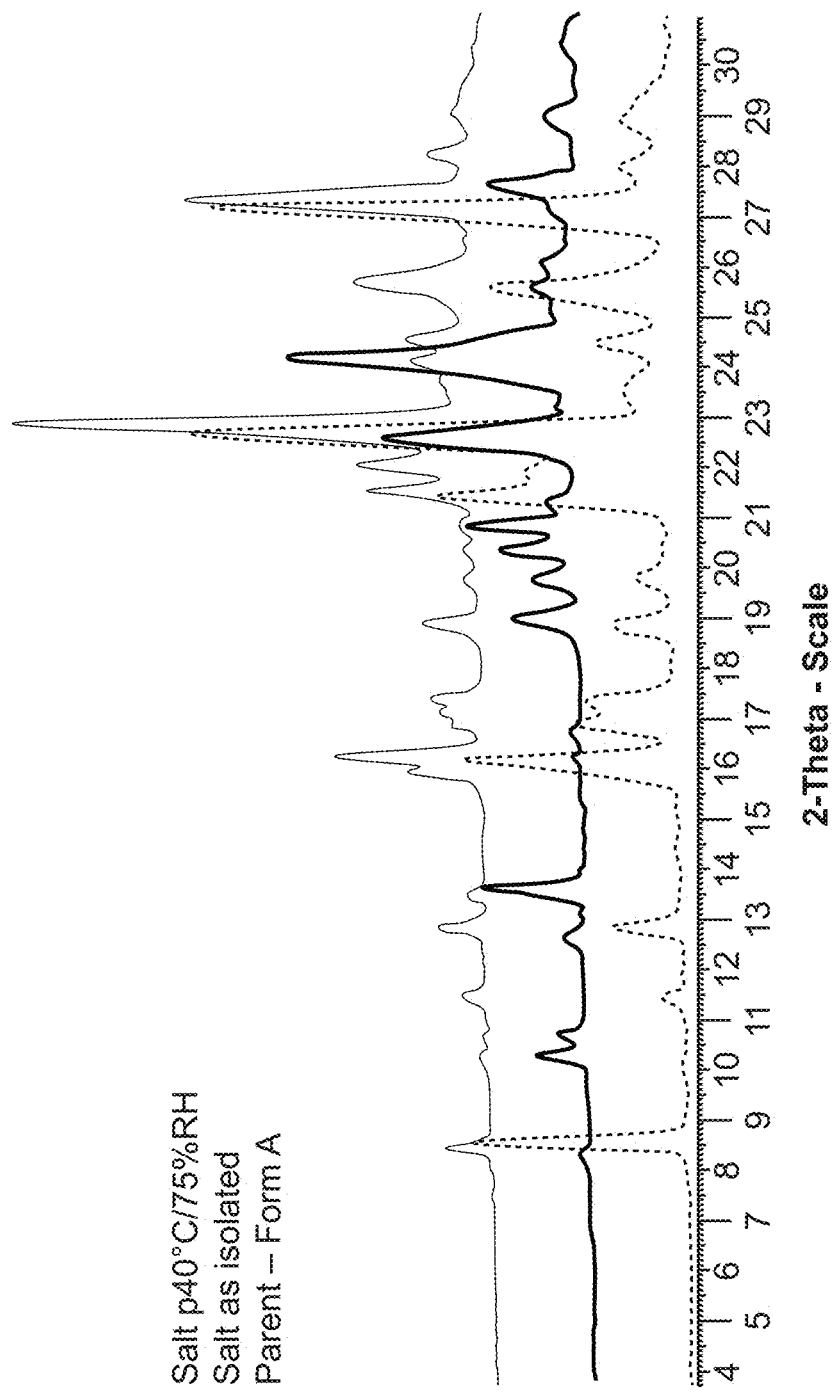
FIG. 25 is an X-ray powder diffraction pattern of Compound A Form A (bottom), and Compound A hydrochloric acid salt as isolated (middle) and at 40° C./75% RH (top).

The XRPD pattern for Compound A hydrochloric acid salt is shown in FIG. 25 and peaks and their related intensities in the XRPD pattern is shown in Table 14 below.

TABLE 14

Peaks in the XRPD Pattern for Compound A hydrochloric acid salt

| Peak Position (°2θ) | Relative Intensity (%) |
|---|---|
| 8.2 | 6.4 |
| 10.2 | 18.3 |
| 10.7 | 13.6 |
| 12.5 | 10.9 |
| 13.6 | 36.1 |
| 19.0 | 27.1 |
| 19.8 | 21.1 |
| 20.3 | 30.6 |
| 20.9 | 42.7 |
| 21.3 | 17.4 |
| 22.5 | 68.5 |
| 24.1 | 100.0 |
| 27.6 | 36.4 |
| 29.0 | 17.9 |
| 25.6 | 21.5 |

Figure 26:
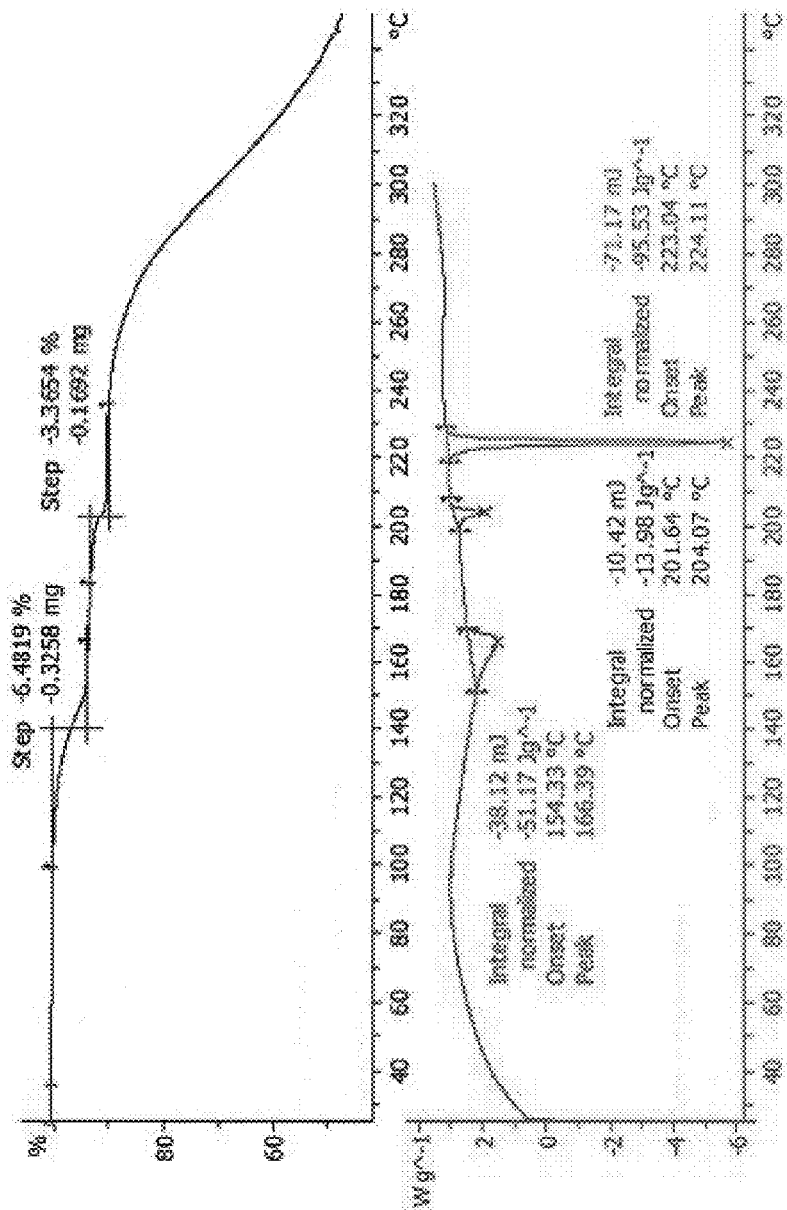
FIG. 26 is a thermogravimetric analysis (TGA) (top) and a differential scanning calorimetry (DSC) curve (bottom) of Compound A hydrochloric acid salt.

The stoichiometry (ionic Compound A:counter ion) was determined to be about 1:1 by Ion Chromatography. The TGA thermogram and DSC thermogram are shown in FIG. 26. The TGA thermogram shows a weight loss between 100-170° C. of 6.5% and a second weight loss between 185-210° C. of 3.4%. The DSC thermogram shows two small endotherms at 154.3 and 201.6° C., and a sharp melt at 223.0° C. Purity was determined to be about 99.1%.

Compound A Sulfuric Acid Salt

Figure 27:
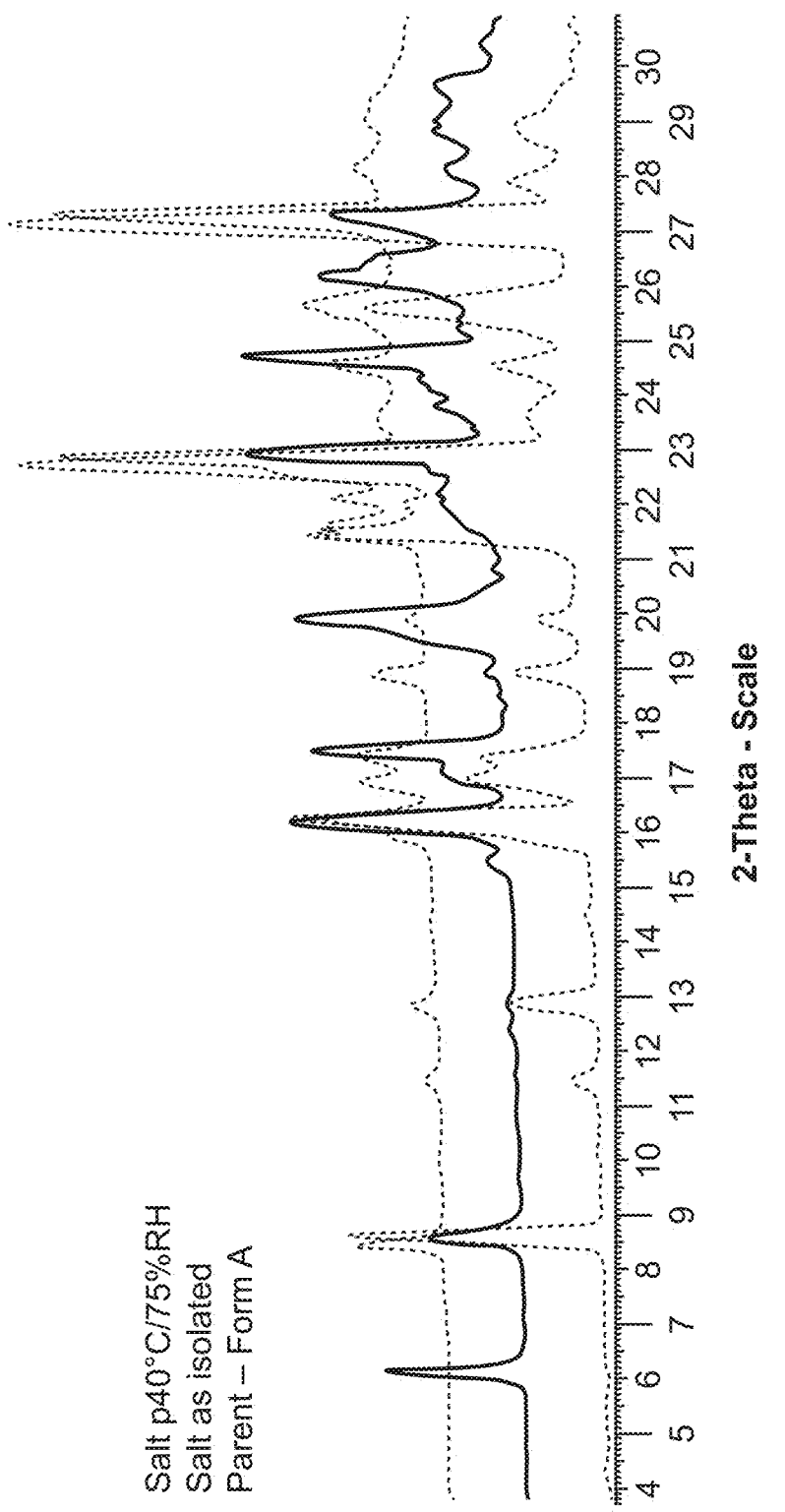
FIG. 27 is an X-ray powder diffraction pattern of Compound A Form A (bottom), and Compound A sulfuric acid salt as isolated (middle) and at 40° C./75% RH (top).

The XRPD pattern for Compound A sulfuric acid salt is shown in FIG. 27 to be a mixture of the salt and Form A. The peaks and their related intensities in the XRPD pattern is shown in Table 15 below.

TABLE 15

Peaks in the XRPD Pattern for Compound A sulfuric acid salt

| Peak Position (°2θ) | Relative Intensity (%) |
|---|---|
| 6.1 | 48.8 |
| 8.5 | 36.2 |
| 15.4 | 15.0 |
| 16.1 | 82.4 |
| 17.1 | 32.4 |
| 17.4 | 75.9 |
| 19.8 | 82.9 |
| 22.9 | 100.0 |
| 23.7 | 33.4 |
| 24.7 | 99.5 |
| 26.1 | 73.0 |
| 27.3 | 70.9 |
| 28.1 | 29.8 |
| 28.8 | 35.1 |
| 29.6 | 35.1 |

Figure 28:
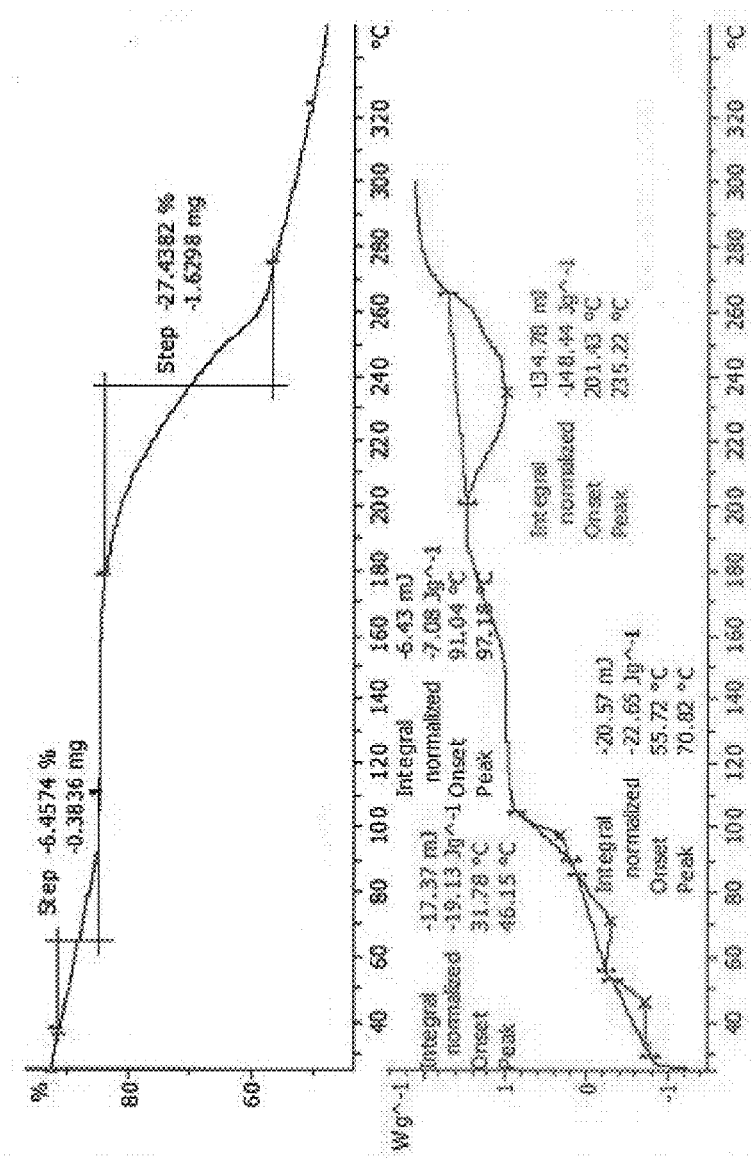
FIG. 28 is a thermogravimetric analysis (TGA) (top) and a differential scanning calorimetry (DSC) curve (bottom) of Compound A sulfuric acid salt.

The TGA thermogram and DSC thermogram are shown in FIG. 28. The TGA thermogram shows a weight loss between 10-110° C. of 6.5% and a second weight loss between 180-280° C. of 27.4%. The DSC thermogram shows three small endotherms at 31.8, 55.7 and 91.0 associated with the first weight loss, and a large, broad endotherm at 201.4° C. due to decomposition.

Compound A Methanesulfonic Acid Salt

Figure 29:
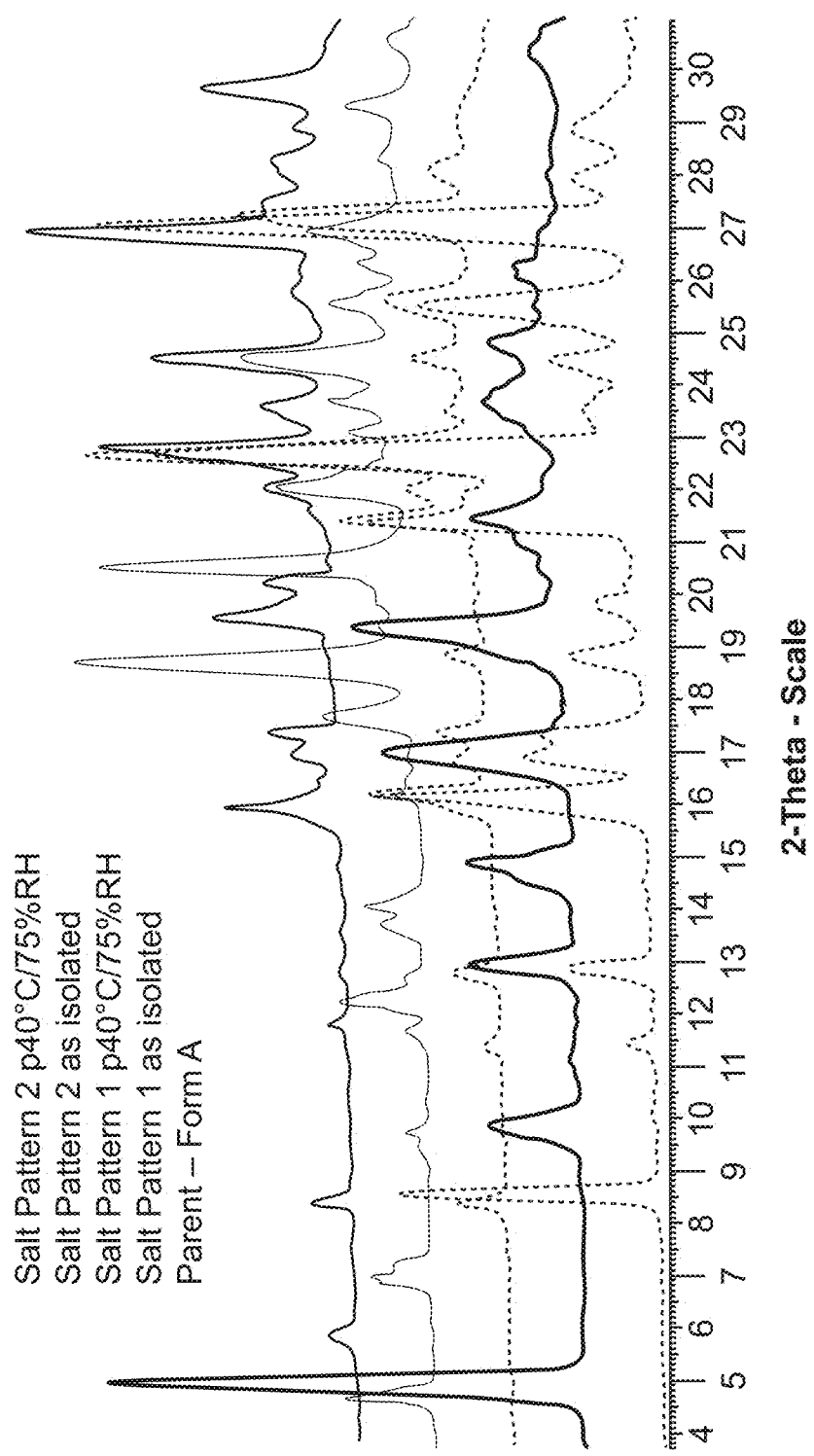
FIG. 29 is an X-ray powder diffraction pattern of Compound A Form A (bottom), Compound A methanesulfonic acid salt pattern 1 as isolated (second to bottom) and at 40°

The XRPD patterns for Compound A methanesulfonic acid salt is shown in FIG. 29 and the peaks and their related intensities in the XRPD patterns are shown in Tables 16 and 17 below. Pattern 1 was observed from acetone, and pattern 2 was observed from THF. Pattern 1 reverted to Form A at 40° C./75% RH and pattern 2 reverted to a mixture of Form A and Pattern 1 at 40° C./75% RH.

TABLE 16

Peaks in the XRPD Pattern for Compound
A methanesulfonic acid salt (Pattern 1)

| Peak Position (°2θ) | Relative Intensity (%) |
|---|---|
| 4.9 | 100.0 |
| 9.8 | 21.0 |
| 12.9 | 24.9 |
| 14.9 | 25.8 |
| 17.0 | 43.9 |
| 19.4 | 49.7 |
| 21.5 | 25.3 |
| 23.7 | 23.4 |
| 24.8 | 21.5 |

TABLE 17

Peaks in the XRPD Pattern for Compound
A methanesulfonic acid salt (Pattern 2)

| Peak Position (°2θ) | Relative Intensity (%) |
|---|---|
| 4.6 | 25.8 |
| 6.9 | 18.4 |
| 7.1 | 12.7 |
| 9.7 | 8.3 |
| 12.2 | 26.6 |
| 11.6 | 8.8 |
| 13.6 | 15.5 |
| 14.0 | 20.1 |
| 17.7 | 31.7 |
| 18.7 | 100.0 |
| 20.5 | 93.8 |
| 22.1 | 44.8 |
| 23.1 | 24.7 |
| 23.7 | 30.7 |
| 24.6 | 54.3 |
| 25.6 | 30.3 |
| 26.4 | 21.6 |
| 27.0 | 36.7 |
| 28.4 | 17.2 |
| 29.3 | 25.4 |
| 30.5 | 14.1 |

For both THF and acetone, the stoichiometry (ionic Compound A:counter ion) was determined to be about 1:1 by NMR. The TGA thermogram and DSC thermogram for the Compound A methanesulfonic acid salt from THF is shown in FIG. 30. The TGA thermogram shows a weight loss between 40-100° C. of 2.1%. The DSC thermogram shows a small endotherm at 153.5° C. and a sharp endotherm at 166.9° C. Purity was determined to be about 99.3%. For the Compound A methanesulfonic acid salt from acetone, the TGA thermogram showed no weight loss until sample degradation at about 180° C., and the DSC thermogram showed an endotherm at 144.5° C. due to sample melt. Purity was determined to be about 98.9%.

Example 6

Preparation of Amorphous Compound A

Figure 23:
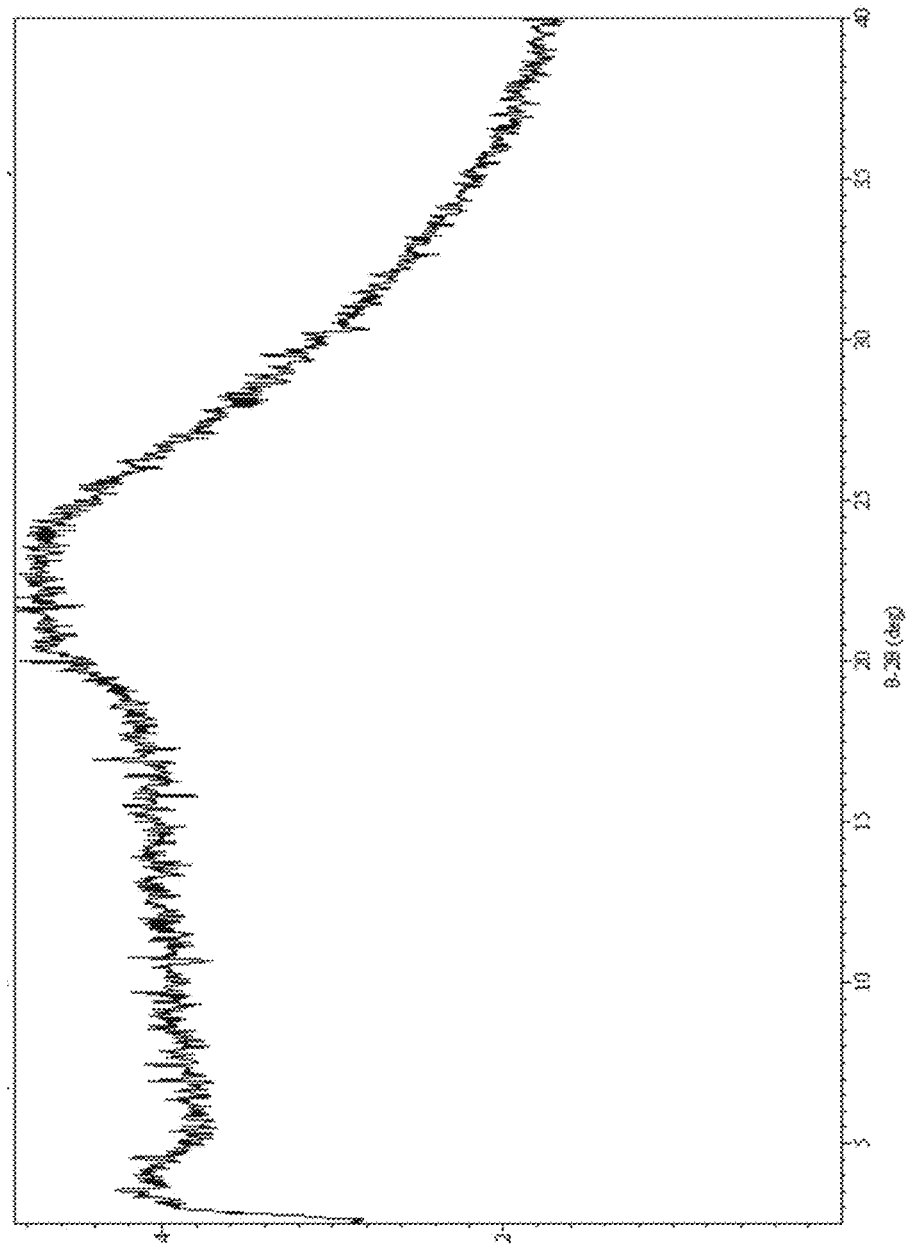
FIG. 23 is an X-ray powder diffraction pattern of amorphous Compound A.

Amorphous Compound A was obtained as follows. Crystalline Compound A Form A (500 mg) was dissolved in THF (1.5 mL) at room temperature. The solution was filtered to remove any residual crystalline material. The solvent was removed by fast evaporation in the rotary evaporator. An aliquot of the obtained solid was examined by XRPD. Alternatively, amorphous Compound A was obtained by lyophilization of Compound A Form A from a mixture of 1,4-dioxane:water (2:1 v/v) or by packing and sealing Compound A into a capillary tube, melting the sample on a Kofler hotbench at about 240° C. for one minute and cooling at ambient temperature. An XRPD of amorphous Compound A is shown in FIG. 23.

Example 7

Preparation of bis TEA Salt of Compound A

Method

The crystalline Compound A Form A (50 mg) was dissolved in acetone (50 vol) at 50° C. The solution was treated with 2.1 mol eq. of triethylamine (TEA). The temperature was maintained at 50° C. for 20 min then cooled to 0° C. at 0.1° C./min with stirring. After 72 at 0° C., the solids were filtered, air dried for 5 min and analysed by XRPD. The solutions were set for slow evaporation at ambient conditions.

Data

The XRPD pattern for Compound A bis TEA salt is shown in FIG. 31 and peaks and their related intensities in the XRPD pattern are shown in Table 18 below.

TABLE 18

Peaks in the XRPD Pattern for Compound A bis triethylamine salt

| Peak Position (°2θ) | Relative Intensity (%) |
|---|---|
| 5.5 | 4.2 |
| 9.2 | 5.0 |
| 10.1 | 29.4 |
| 11.7 | 13.2 |
| 13.3 | 8.0 |
| 13.7 | 17.3 |
| 14.5 | 42.5 |
| 14.7 | 52.1 |
| 15.2 | 9.3 |
| 15.7 | 14.3 |
| 16.3 | 16.0 |
| 17.0 | 36.9 |
| 18.4 | 11.9 |
| 19.4 | 31.5 |
| 20.4 | 21.7 |
| 20.7 | 27.3 |
| 22.6 | 100.0 |
| 22.9 | 23.9 |
| 23.9 | 29.9 |
| 24.8 | 14.6 |
| 25.5 | 38.5 |
| 26.3 | 16.7 |
| 27.2 | 37.1 |
| 28.1 | 62.2 |

The TGA thermogram and DSC thermogram are shown in FIG. 32. The TEA was isolated as a bis salt, however the salt started to dissociate to Form A after one week storage at 40° C./75% RH.

Example 8

Preparation of Hemi Calcium and Magnesium Salts

Method

The calcium and magnesium salts of Compound A were prepared by ion exchange from the sodium salt. Compound A (450 mg) was dissolved in acetone at 50° C. (50 vol, 22.5 ml). The solution was treated with 1.1 mol eq. of sodium hydroxide (1 M solution in water). A suspension was formed on addition then it was cooled to 0° C. at 0.1° C./min. After 48 h at 0° C., the solid was filtered, air dried for 10 min and analysed by XRPD. The sodium salt (50 mg) was dissolved in MeOH (20 vol, 1 ml) at room temperature. The solution was heated to 50° C. and then treated with the corresponding counter ion (1 M solutions in MeOH). The mixtures were cooled to 0° C. at 0.1° C./min. After 24 h at 0° C., the solids were filtered, air dried for 5 min and analyzed by XRPD (first crop). The liquors were kept and set for slow evaporation at ambient conditions to provide a second crop. The materials isolated from the $Ca^{+2}$ and $Mg^{+2}$ hemi salt experiments crystallized after one week incubation at 40° C./75% RH.

Data

The XRPD patterns for the Compound A hemi calcium and magnesium salts are shown in FIG. 33 and FIG. 35, respectively. The peaks and their related intensities in the XRPD patterns are shown in Tables 19 and 20 below.

TABLE 19

Peaks in the XRPD Pattern for Compound A hemi calcium salt

| Peak Position (°2θ) | Relative Intensity (%) |
|---|---|
| 5.7 | 8.8 |
| 6.6 | 10.5 |
| 8.6 | 10.2 |
| 9.7 | 8.1 |
| 10.9 | 24.0 |
| 11.5 | 63.5 |
| 12.9 | 36.4 |
| 13.4 | 20.5 |
| 14.4 | 32.8 |
| 14.6 | 34.0 |
| 15.3 | 20.8 |
| 17.0 | 27.6 |
| 17.7 | 19.6 |
| 20.0 | 29.0 |
| 21.6 | 31.0 |
| 23.1 | 51.9 |
| 23.8 | 39.2 |
| 24.4 | 52.4 |
| 25.9 | 100.0 |
| 27.0 | 88.1 |
| 28.1 | 40.3 |
| 29.3 | 25.7 |

TABLE 20

Peaks in the XRPD Pattern for Compound A hemi magnesium salt

| Peak Position (°2θ) | Relative Intensity (%) |
|---|---|
| 5.0 | 12.7 |
| 7.1 | 37.2 |
| 7.5 | 24.9 |
| 8.0 | 30.0 |
| 10.0 | 30.2 |
| 11.4 | 35.4 |
| 11.9 | 37.5 |
| 12.6 | 33.9 |
| '12.9 | 37.5 |
| 15.9 | 45.4 |
| 17.8 | 50.4 |
| 18.9 | 44.4 |
| 20.1 | 67.6 |
| 21.0 | 59.0 |
| 21.7 | 67.9 |
| 22.8 | 100.0 |

The DSC thermograms for the Compound A hemi calcium and magnesium salts are shown in FIG. 34 and FIG. 36, respectively.

Example 9

Single Crystal of Compound A Form A

Single crystals were grown from acetone with sufficient quality for structure determination by single crystal X-ray diffraction.

The structure solution was obtained by direct methods, full-matrix least-squares refinement on $F^2$ with weighting $w^{-1}=\sigma 2(F_o^2)+(0.0697P)^2+(0.3149P)$, where $P=(F_o^2+2F_c^2)/3$, anisotropic displacement parameters, empirical absorption correction using spherical harmonics, implemented in SCALE3 ABSPACK scaling algorithm. Final $wR^2=\{\Sigma[w(F_o^2-2F_c^2)^2]/\Sigma[w(F_o^2)^2]^{1/2}\}=0.1376$ for all data, conventional $R_1=0.0467$ on F values of 2496 reflections with $F_o>4\sigma(F_o)$, S=1.045 for all data and 248 parameters. Final $\Delta/\sigma(max)$ 0.000, $\Delta/\sigma(mean)$, 0.000. Final difference map between +0.211 and −0.318 e Å$^{-3}$.

FIG. 37 shows a view of a molecule of Compound A Form A from the crystal structure showing the numbering scheme employed. Anisotropic atomic displacement ellipsoids for the non-hydrogen atoms are shown at the 50% probability level. Hydrogen atoms are displayed with an arbitrarily small radius.

TABLE 21

Samples Submitted for Single Crystal X-Ray Diffraction Studies

| | | | |
|---|---|---|---|
| Molecular Formula | $C_{19}H_{16}N_2O_5$ | | |
| Molecular Weight | 352.34 | | |
| Crystal system | Triclinic | | |
| Space group P-1 | a | 8.5208(13) Å, α | 98.415(11)°, |
| | b | 9.2233(13) Å, β | 108.788(12)°, |
| | c | 11.1859(14) Å, γ | 102.841(12)° |
| V | 788.50(19) Å$^3$ | | |
| Z | 2 | | |
| $D_c$ | 1.484 g · cm$^{-1}$ | | |
| μ | 0.909 mm$^{-1}$ | | |
| Source, λ | Cu—Kα, 1.54178 Å | | |
| F(000) | 368 | | |
| T | 100(2) K | | |
| crystal | Colorless prism, 0.11 × 0.05 × 0.02 mm | | |
| data truncated to | 0.80 Å | | |
| $\theta_{max}$ | 77.18° | | |
| Completeness | 98.2% | | |
| Reflections | 12441 | | |
| Unique reflections | 3282 | | |
| $R_{int}$ | 0.0406 | | |

Example 10

Preparation of Compound A a) 5-Phenoxyphthalide

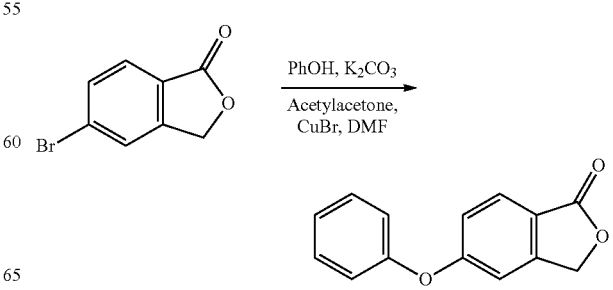

A reactor was charged with DMF (68 Kg), and stirring was initiated. The reactor was then charged with phenol (51 Kg), acetylacetone (8 Kg), 5-bromophthalide (85 Kg), copper bromide (9 Kg), and potassium carbonate (77 Kg). The mixture was heated above 85° C. and maintained until reaction completion and then cooled. Water was added. Solid was filtered and washed with water. Solid was dissolved in dichloromethane, and washed with aqueous HCl and then with water. Solvent was removed under pressure and methanol was added. The mixture was stirred and filtered. Solid was washed with methanol and dried in an oven giving 5-phenoxyphthalide (Yield: 72%. HPLC: 99.6%).

b) 2-Chloromethyl-4-phenoxybenzoic acid methyl ester

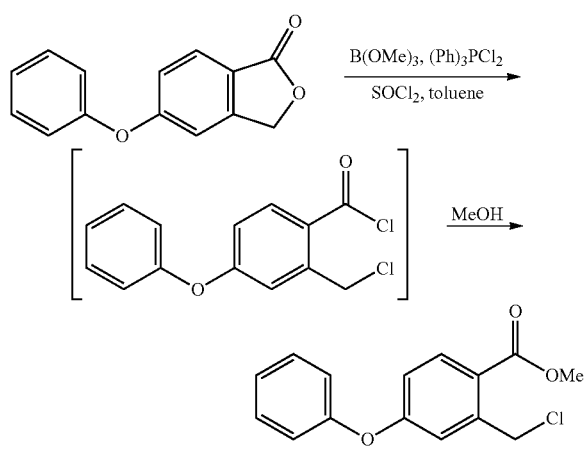

A reactor was charged with toluene (24 Kg), and stirring was initiated. The reactor was then charged with 5-phenoxyphthalide (56 Kg), thionyl chloride (41 Kg), trimethyl borate (1 Kg), dichlorotriphenylphosphorane (2.5 Kg), and potassium carbonate (77 Kg). The mixture was heated to reflux until reaction completion and solvent was removed leaving 2-chloromethyl-4-phenoxybenzoyl chloride. Methanol was charged and the mixture was heated above 50° C. until reaction completion. Solvent was removed and replaced with DMF. This solution of the product methyl 2-chloromethyl-4-phenoxybenzoic acid methyl ester in DMF was used directly in the next step (HPLC: 85%).

c) 4-Hydroxy-7-phenoxyisoquinoline-3-carboxylic acid methyl ester (1a)

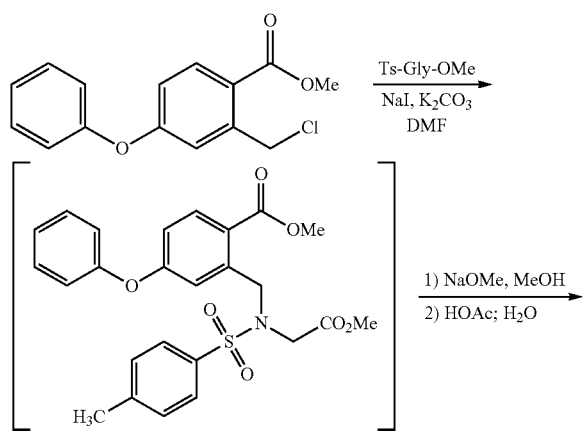

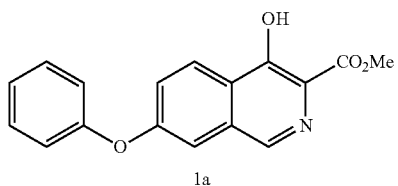

A reactor was charged with a solution of 2-chloromethyl-4-phenoxybenzoic acid methyl ester (~68 Kg) in DMF, and stirring was initiated. The reactor was then charged with p-toluenesulfonylglycine methyl ester (66 Kg), potassium carbonate (60 Kg), and sodium iodide (4 Kg). The mixture was heated to at least 50° C. until reaction completion. The mixture was cooled. Sodium methoxide in methanol was charged and the mixture was stirred until reaction completion. Acetic acid and water were added, and the mixture was stirred, filtered and washed with water. Solid was purified by acetone trituration and dried in an oven giving 1a (Yield from step b): 58%; HPLC: 99.4%). $^1$H NMR (200 MHz, DMSO-d6) δ 11.60 (s, 1 H), 8.74 (s, 1H), 8.32 (d, J=9.0 Hz, 1 H), 7.60 (dd, J=2.3 & 9.0 Hz, 1H), 7.49 (m, 3 H), 7.24 (m, 3 H), 3.96 (s, 3 H); MS-(+)-ion M+1=296.09 d) Methyl 1-((dimethylamino)methyl)-4-hydroxy-7-phenoxyisoquinoline-3-carboxylate (1b)

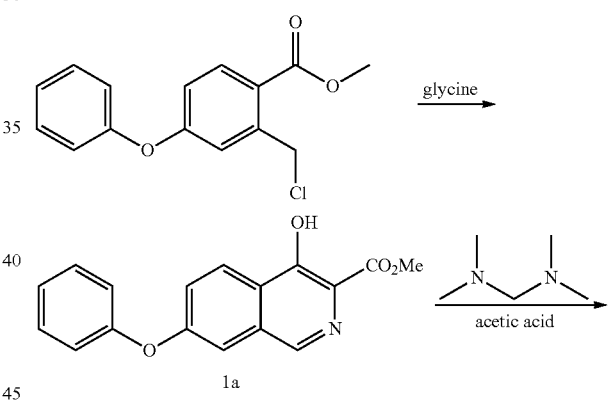

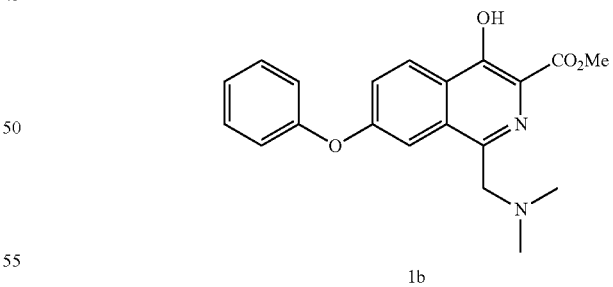

A flask was charged with 1a (29.5 g) and acetic acid (44.3 g±5%), and then stirred. Bis-dimethylaminomethane (12.8 g±2%) was slowly added. The mixture was heated to 55±5° C. and maintained until reaction completion. The reaction product was evaluated by MS, HPLC and $^1$H NMR. $^1$H NMR (200 MHz, DMSO-d6) δ 11.7 (s, 1 H), 8.38 (d. J=9.0 Hz, 1 H), 7.61 (dd, J=9.0, 2.7 Hz, 1 H), 7.49 (m, 3 H), 7.21 (m, 3 H), 5.34 (s, 2 H), 3.97 (s, 3 H), 1.98 (s, 3 H); MS-(+)-ion M+1=368.12.

e) Methyl 1-((acetoxy)methyl)-4-hydroxy-7-phe-
noxyisoquinoline-3-carboxylate (1c)

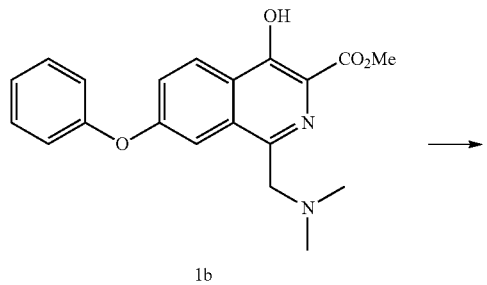

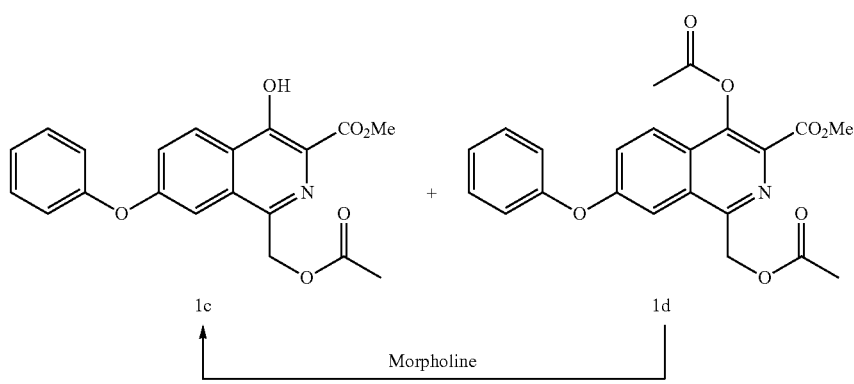

The solution of 1b from a) above was cooled below 25° C., at which time acetic anhydride (28.6 g±3.5%) was added to maintain temperature below 50° C. The resulting mixture was heated to 100±5° C. until reaction completion.

The solution of 1c and 1d from above was cooled to less than 65±5° C. Water (250 mL) was slowly added. The mixture was then cooled to below 20±5° C. and filtered. The wet cake was washed with water (3×50 mL) and added to a new flask. Dichloromethane (90 mL) and water (30 mL) were added, and the resulting mixture was stirred. The dichloromethane layer was separated and evaluated by HPLC.

The organic layer was added to a flask and cooled 5±5° C. Morpholine was added and the mixture was stirred until reaction completion. Solvent was replaced with acetone/methanol mixture. After cooling, compound 1c precipitated and was filtered, washed and dried in an oven (Yield: 81%, HPLC: >99.7%). $^1$H NMR (200 MHz, DMSO-d6) δ 11.6 (S, 1 H), 8.31 (d, J=9.0 Hz, 1 H), 7.87 (d, J=2.3 Hz, 1 H), 7.49 (m, 3 H), 7.24 (m, 3 H), 3.95 (s, 3 H), 3.68 (s, 2H), 2.08 (s, 6 H); MS-(+)-ion M+1=357.17.

f) Methyl 4-hydroxy-1-methyl-7-phenoxyisoquino-
line-3-carboxylate (1e)

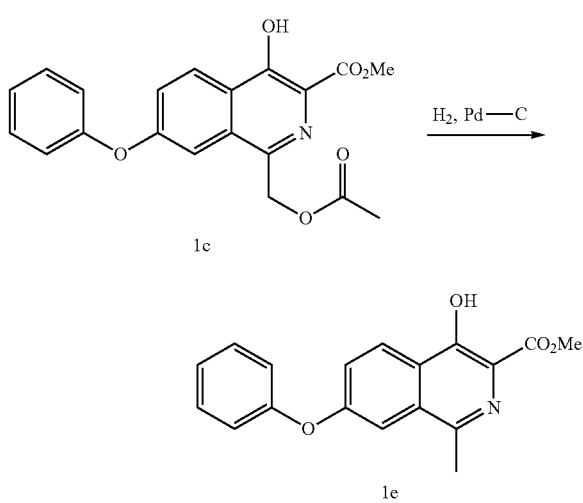

A reactor was charged with 1c (16.0 g), Pd/C (2.08 g), anhydrous $Na_2CO_3$ (2.56 g) and ethyl acetate (120 mL). The flask was vacuum-purged with nitrogen (3×) and vacuum-purged with hydrogen (3×). The flask was then pressurized with hydrogen and stirred at about 60° C. until completion of reaction. The flask was cooled to 20-25° C., the pressure released to ambient, the head space purged with nitrogen three times and mixture was filtered. The filtrate was concentrated. Methanol was added. The mixture was stirred and then cooled. Product precipitated and was filtered and dried in an oven (Yield: 90%, HPLC: 99.7%).

g) [(4-Hydroxy-1-methyl-7-phenoxy-isoquinoline-3-carbonyl)-amino]-acetic acid (Compound A)

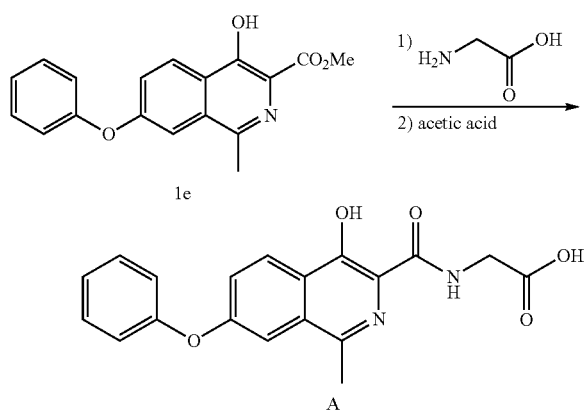

A pressure flask was charged with 1e (30.92 g), glycine (22.52 g), methanol (155 mL), sodium methoxide solution (64.81 g) and sealed (as an alternative, sodium glycinate was used in place of glycine and sodium methoxide). The reaction was heated to about 110° C. until reaction was complete. The mixture was cooled, filtered, washed with methanol, dried under vacuum, dissolved in water and washed with ethyl acetate. The ethyl acetate was removed and to the resulting aqueous layer an acetic acid (18.0 g) solution was added. The suspension was stirred at room temperature, filtered, and the solid washed with water (3×30 mL), cold acetone (5-10° C., 2×20 mL), and dried under vacuum to obtain Compound A (Yield: 86.1%, HPLC: 99.8%).

Example 11

Biological Testing

The solid forms provided herein can be used for inhibiting HIF hydroxylase activity, thereby increasing the stability and/or activity of hypoxia inducible factor (HIF), and can be used to treat and prevent HIF-associated conditions and disorders (see, e.g., U.S. Pat. No. 7,323,475, U.S. Patent Application Publication No. 2007/0004627, U.S. Patent Application Publication No. 2006/0276477, and U.S. Patent Application Publication No. 2007/0259960, incorporated by reference herein).

The biological activity of the solid forms provided herein may be assessed using any conventionally known method. In particular embodiments, cells derived from animal tissues, preferably human tissues, capable of expressing erythropoietin when stimulated by compounds of the invention are cultured for the in vitro production of endogenous proteins. Cells contemplated for use in such methods include, but are not limited to, cells derived from hepatic, hematopoietic, renal, and neural tissues.

Cell culture techniques are generally available in the art and include any method that maintains cell viability and facilitates expression of endogenous proteins. Cells are typically cultured in a growth medium optimized for cell growth, viability, and protein production. Cells may be in suspension or attached to a substrate, and medium may be supplied in batch feed or continuous flow-through regimens. Compounds of the invention are added to the culture medium at levels that stimulate erythropoietin production without compromising cell viability. Erythropoictin produced by the cells is secreted into the culture medium. The medium is then collected and the erythropoietin is purified using methods known to those of skill in the art. (See, e.g., Lai et al. (1987) U.S. Pat. No. 4,667,016; and Egrie (1985) U.S. Pat. No. 4,558,006.)

Suitable assay methods are well known in the art. The following are presented only as examples and are not intended to be limiting.

Cell-based HIFα Stabilization Assay

Human cells (e.g., Hep3B cells from hepatocellular tissue) derived from various tissues were separately seeded into 35 mm culture dishes, and grown at 37° C., 20% $O_2$, 5% $CO_2$ in standard culture medium, e.g., DMEM (Dulbecco's modification of Eagle's medium), 10% FBS (fetal bovine serum). When cell layers reach confluence, the media was replaced with OPTI-MEM media (Invitrogen Life Technologies, Carlsbad Calif.), and cell layers were incubated for approximately 24 hours in 20% $O_2$, 5% $CO_2$ at 37° C. Compound A or 0.013% DMSO (dimethyl sulfoxide) was then added to existing medium and incubation was continued overnight.

Following incubation, the media was removed, centrifuged, and stored for analysis (see Cell-based VEGF and EPO assays below). The cells were washed two times in cold phosphate buffered saline (PBS) and then lysed in 1 mL, of 10 mM Tris (pH 7.4), 1 mM EDTA, 150 mM NaCl, 0.5% IGEPAL (Sigma-Aldrich, St. Louis Mo.), and a protease inhibitor mix (Roche Molecular Biochemicals) for 15 minutes on ice. Cell lysates were centrifuged at 3,000×g for 5 minutes at 4° C., and the cytosolic fractions (supernatant) were collected. The nuclei (pellet) were resuspended and lysed in 100 μL of 20 mM HEPES (pH 7.2), 400 mM NaCl, 1 mM EDTA, 1 mM dithiothreitol, and a protease mix (Roche Molecular Biochemicals), centrifuged at 13,000×g for 5 minutes at 4° C., and the nuclear protein fractions (supernatant) were collected.

The Nuclear protein fractions collected were analyzed for HIF-1α using a QUANTIKINE immunoassay (R&D Systems, Inc., Minneapolis Minn.) according to the manufacturer's instructions.

Cell-based EPO Assay

Hep3B cells (human hepatocellular carcinoma cells from ATCC, cat #HB-8064) were plated at 25,000 cells per well 96 well plates. The next day, the cells were washed once with DMEM (Cellgro, cat #10-013-CM)+0.5% fetal bovine serum (Cellgro, cat #35-010-CV) and incubated with various concentrations of compound or vehicle control (0.15% DMSO) in DMEM+0.5% fetal bovine serum for 72 hours. Cell free culture supernatants were generated by transfer to a conical bottom 96 well plate and centrifugation for 5 minutes at 2000 rpm. The supernatant was quantitated for EPO using a human EPO ELISA kit (R&D Systems, cat #DEP 00).

The EPO values for the compounds reported herein (e.g., Table 22) are the measured value for cells plus compound minus the value for the vehicle control for the same cell preparation. The EPO values for the vehicle control for the cell preparations varied from 0-12.5 mIU/mL.

HIF-PH Assay

Ketoglutaric acid α-[1-$^{14}$C]-sodium salt, alpha-ketoglutaric acid sodium salt, and HPLC purified peptide were obtained from commercial sources, e.g., Perkin-Elmer (Wellesley Mass.), Sigma-Aldrich, and SynPep Corp. (Dublin Calif.), respectively. Peptides for use in the assay were fragments of HIFα as described above or as disclosed in International Publication WO 2005/118836, incorporated by reference herein. For example, a HIF peptide for use in the HIF-PH assay was [methoxycoumarin]-DLDLEALAPYI-PADDDFQL-amide. HIF-PH, e.g., HIF-PH2 (also known as EGLN1 or PHD2), was expressed in, e.g., insect Hi5 cells, and partially purified, e.g., through a SP ion exchange chromatography column. Enzyme activity was determined by capturing $^{14}CO_2$ using an assay described by Kivirikko and Myllyla (1982, *Methods Enzymol*, 82:245-304). Assay reactions contained 50 mM HEPES (pH 7.4), 100 μM α-ketoglutaric acid sodium salt, 0.30 μCi/mL α-ketoglutaric acid α-[1-$^{14}$C]-sodium salt, 40 μM $FeSO_4$, 1 mM ascorbate, 1541.8 units/mL Catalase, with or without 50 μM peptide substrate and various concentrations of compound of the invention. Reactions were initiated by addition of HIF-PH enzyme.

The peptide-dependent percent turnover was calculated by subtracting percent turnover in the absence of peptide from percent turnover in the presence of substrate peptide. Percent inhibition and $IC_{50}$ were calculated using peptide-dependent percent turnover at given inhibitor concentrations. Calculation of $IC_{50}$ values for each inhibitor was conducted using GraFit software (Erithacus Software Ltd., Surrey UK). The results are summarized in Table 22.

Table 21 below was intended to demonstrate the pharmacological utility of Compound A. By inhibiting HIF prolyl hydroxylase enzymes (for example PHD2, also known as EGLN1), Compound A stabilizes HIFα, which then combines with HIFβ to form an active transcription factor that increases expression of numerous genes involved in response to hypoxic and ischemic conditions, including erythropoietin (EPO). Therefore Compound A can be used for the prevention, pretreatment, or treatment of conditions associated with HIF and or EPO including anemic, ischemic and hypoxic conditions.

TABLE 22

| | $IC_{50}$ PHD2 (μM) | Cell EPO* (mIU/mL) |
|---|---|---|
| Compound A Form A | 2.1 | 182 |

*Cell EPO measured at 30 μM compound in DMSO compared to DMSO only control

The invention claimed is:

1. A composition comprising crystalline [(4-hydroxy-1-methyl-7-phenoxy-isoquinoline-3-carbonyl)-amino]-acetic acid (Compound A Form A), wherein at least about 85% of Compound A is in Form A.

2. The composition of claim 1, wherein the Compound A Form A is characterized by a differential scanning calorimetry (DSC) curve that comprises an endotherm at about 223° C.

3. The composition of claim 2, wherein the DSC curve is substantially as shown in FIG. 2.

4. The composition of claim 1, wherein the Compound A Form A is characterized by an X-ray powder diffractogram comprising a peak at 8.5 °2θ±0.2°2θ.

5. The composition of claim 1, wherein the Compound A Form A is characterized by an X-ray powder diffractogram comprising a peak at 16.2 °2θ±0.2°2θ.

6. The composition of claim 1, wherein the Compound A Form A is characterized by an X-ray powder diffractogram comprising a peak at 27.4 °2θ±0.2°2θ.

* * * * *